(12) United States Patent
Lagrange et al.

(10) Patent No.: US 7,655,052 B2
(45) Date of Patent: Feb. 2, 2010

(54) COMPOSITION FOR THE COLORING OF KERATINOUS FIBERS COMPRISING A HALOCHROMIC COMPOUND, THE DYE CORRESPONDING TO THIS COMPOUND, AND METHODS OF USE THEREOF

(75) Inventors: Alain Lagrange, Coupvray (FR); Frédéric Guerin, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/076,565

(22) Filed: Mar. 20, 2008

(65) Prior Publication Data

US 2008/0235883 A1 Oct. 2, 2008

Related U.S. Application Data

(60) Provisional application No. 60/907,391, filed on Mar. 30, 2007.

(30) Foreign Application Priority Data

Mar. 20, 2007 (FR) .................................. 07 53924

(51) Int. Cl.
*A61Q 5/10* (2006.01)
(52) U.S. Cl. ........................ 8/405; 8/406; 8/407; 8/435; 8/462; 8/565; 8/567; 8/568; 8/570; 8/571; 8/572; 8/573; 8/574; 8/575; 8/576
(58) Field of Classification Search ................ 8/405, 8/406, 407, 435, 462, 565, 566, 567, 568, 8/570, 571, 572, 573, 574, 575, 576
See application file for complete search history.

(56) References Cited

U.S. PATENT DOCUMENTS

| | | | | |
|---|---|---|---|---|
| 4,132,436 A | * | 1/1979 | Ishige et al. ................. | 503/218 |
| 4,506,073 A | | 3/1985 | Balli et al. | |
| 4,562,449 A | * | 12/1985 | Balli et al. ................... | 503/218 |
| 4,754,034 A | | 6/1988 | Berneth et al. | |
| 4,968,797 A | * | 11/1990 | Berneth et al. ............... | 544/284 |
| 2004/0163186 A1 | * | 8/2004 | Simonet et al. ................ | 8/405 |

FOREIGN PATENT DOCUMENTS

| EP | 0 091 402 A2 | 10/1983 |
|---|---|---|
| EP | 1 532 970 A2 * | 5/2005 |
| FR | 2 862 530 | 5/2005 |
| FR | 2 862 531 | 5/2005 |
| FR | 2 862 532 | 5/2005 |
| JP | 54-126114 | 10/1979 |

OTHER PUBLICATIONS

STIC Search Report dated Aug. 21, 2008.*
English Abstract of EP 1532 970 A2 (2005).*
French Search Report, dated Nov. 21, 2007, 2 pages.
English Language Abstract for FR 2 862 530, (2005).
English Language Abstract for FR 2 862 531, (2005).
English Language Abstract for FR 2 862 532, (2005).
English Language Abstract for JP 54-126114, (1979).
English Language Abstract for journal article by Zal'kind, Ys et al, (1954).
European Search Report, dated Aug. 28, 2008, 2 pages.
Gabbutt, CD et al. "Oxidation and ring cleavage reactions of 3-benzhyhrylchromones. Generation of triarylmethine cations from methylidenechroman-4-ones and benzopyrano[4,3-c]pyrazoles," *Tetrahedron*, 62: 10945-10953 (2006).
Zal'kind, YS et al. "Condensation of tetraphenylbutynediol with phenol," *Zhurnal Obshchei Khimii*, 15: 488-498 (1945), English Abstract.

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

Disclosed herein is the use, in the coloring of keratinous fibers, for example human keratinous fibers, such as the hair, of a composition comprising at least one compound chosen from the compounds of formula (I) comprising a cyclic group G including a ring H capable of opening, the dyes corresponding to the compounds of formula (I) wherein the ring H is open and the addition salts thereof:

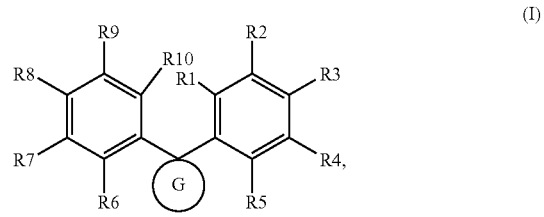

and a method for treating keratinous fibers employing this composition.

23 Claims, No Drawings

COMPOSITION FOR THE COLORING OF KERATINOUS FIBERS COMPRISING A HALOCHROMIC COMPOUND, THE DYE CORRESPONDING TO THIS COMPOUND, AND METHODS OF USE THEREOF

This application claims benefit of U.S. Provisional Application No. 60/907,391, filed Mar. 30, 2007, the contents of which are incorporated herein by reference. This application also claims benefit of priority under 35 U.S.C. § 119 to French Patent Application No. FR 0753924, filed Mar. 20, 2007, the contents of which are also incorporated herein by reference.

The present disclosure relates to the use, in the coloring of keratinous fibers, for example human keratinous fibers, such as the hair, of a composition comprising at least one suitably selected halochromic compound and/or the dye corresponding to this compound.

Within the art of dyeing keratinous fibers, for example human keratinous fibers, such as the hair, it is known practice to dye the hair with dyeing compositions comprising oxidation dye precursors, generally known as oxidation bases, such as ortho- or para-phenylenediamines, ortho- or para-aminophenols and heterocyclic compounds, such as diaminopyrazole derivatives. These oxidation bases can be colorless or weakly colored compounds which, in combination with oxidizing products, can give rise, by an oxidative coupling process, to colored compounds.

It is also known that it is possible to vary the shades obtained with these oxidation bases by combining them with couplers or coloring modifiers, the latter being chosen, for example from aromatic meta-diamines, meta-aminophenols, meta-diphenols and certain heterocyclic compounds, such as indole compounds.

The variety of compounds used as oxidation bases and couplers can make it possible to obtain a rich palette of colors.

The "permanent" coloring obtained by these oxidation dyes furthermore should satisfy a certain number of requirements. The oxidation dyes must be toxicologically safe. It should be possible to obtain shades with a desired intensity and the oxidation dyes should behave well in the face of external agents, such as light, bad weather, washing, permanent waving, perspiration and rubbing.

The dyes should also be able to cover white hair and be as non-selective as possible, i.e. make it possible to obtain the smallest possible differences in coloring along the same keratinous fiber, which is generally differently sensitized (i.e., damaged) between its tip and its root.

It is also known practice to dye keratinous fibers, for instance human keratinous fibers, such as the hair, with dyeing compositions comprising direct dyes. These dyes are colored and are coloring molecules that have an affinity for keratinous fibers. They are applied to keratinous fibers for a time necessary for the desired coloring to be obtained and are then rinsed off.

The conventional dyes which can be used include, for example, nitrobenzene, anthraquinone, nitropyridine, azo, cationic azo, xanthene, acridine, azine and triarylmethane dyes or natural dyes.

Direct dyes are very widely used as they sometimes exhibit certain advantages in comparison with oxidation dye precursors, such as a reduction in potential risks of allergy, the absence of sensitizing of the individual hair due to the oxidation process and shorter development times.

However, the colorations obtained are temporary or semi-permanent as the nature of the interactions which bind the direct dyes to the keratinous fiber and their desorption from the surface and/or from the core of this fiber are believed to be responsible for their low dyeing power and for their poor resistance to washing operations, to bad weather or to perspiration. In addition, these direct dyes are generally sensitive to light due to the poor resistance of the chromophore with regard to photochemical attacks, which may result over time in dulling of the coloring of the hair.

The user can choose the method of coloring which allows him to obtain shades suited to his requirements in terms of highlights and persistence. However, in order to erase the colors thus obtained, it is necessary to use bleaching compositions comprising at least one oxidizing agent and/or at least one reducing agent of reductone, thiol or sulfite type. Non-limiting mention may be made, among oxidizing agents conventionally used, of hydrogen peroxide or compounds capable of producing hydrogen peroxide by hydrolysis, such as, urea hydrogen peroxide, and persalts, such as perborates, persulfates and percarbonates. The use of these oxidizing agents may result in significant damage to keratinous fibers and detrimental effects to their cosmetic properties. The hair may have a tendency to become rough, more difficult to disentangle and more brittle. Reducing agents, for example reductone, thiol and sulfite may exhibit the disadvantage of not being suitable for all types of dyes. Although reducing agents may make it possible to efficiently erase azo dyes without damaging the keratinous fiber, they are ineffective with dyes derived from anthraquinones.

Furthermore, the use in the coloring of keratinous fibers of specific halochromic compounds is known, for example, from French Application Publication No. FR 2 862 530, which describes compounds comprising a ring which can undergo opening with the formation of an acid group, and French Application Publication No. FR 2 862 531, which describes compounds comprising a lactone ring, and French Application Publication No. FR 2 862 532, which describes dimers of compounds comprising a lactone ring. These compounds make it possible to obtain compositions for the dyeing of keratinous fibers which may partially overcome the disadvantages indicated above but which are still insufficiently effective.

Thus, one aspect of the present disclosure is novel halochromic compounds for the dyeing of keratinous fibers which may make it possible to obtain improved compositions for the dyeing of keratinous fibers that overcome at least one of the disadvantages mentioned above. Further, another aspect of the present disclosure is novel halochromic compounds for the dyeing of keratinous fibers which may make it possible to obtain colorings rapidly with intensive and persistent highlights which can be erased using an external agent, for example a pH agent or heat, which does not detrimentally affect the keratinous fibers.

Still another aspect of the present disclosure is a composition and the use thereof, in the coloring of keratinous fibers, for example, human keratinous fibers, such as the hair comprising, in a medium appropriate for dyeing, at least one compound chosen from the compounds of formula (I) comprising a cyclic group G including a ring H capable of opening, the dyes corresponding to the compounds of formula (I) wherein the ring H is open, and the addition salts thereof:

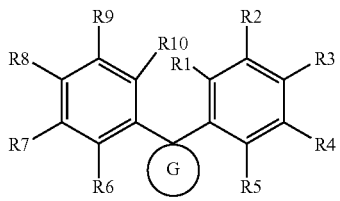

(I)

wherein:

$R_1$, $R_2$, $R_3$, $R_4$, $R_5$, $R_6$, $R_7$, $R_8$, $R_9$ and $R_{10}$ are each independently chosen from:

hydrogen atoms;

halogen atoms;

hydroxyl radicals;

nitro radicals;

amino radicals;

carboxyl radicals;

aminocarbonyl radicals;

cyano radicals; and radicals resulting from a hydrocarbon chain comprising from 1 to 100 carbon atoms, for example from 1 to 50, which is linear or branched, saturated or unsaturated and acyclic or monocyclic, wherein the ring is aromatic or nonaromatic, or polycyclic, wherein the rings are fused or unfused and aromatic or nonaromatic, which can be interrupted or terminated at one of its ends by at least one heteroatom chosen from oxygen and sulfur atoms or by at least one group chosen from carbonyl, SO, $SO_2$ and NH groups and which can be terminated at its other end by a hydrocarbonyl group or by a group comprising at least one heteroatom chosen from nitrogen, oxygen and sulfur atoms, it being possible for the hydrocarbon chain to be substituted by at least one group chosen from the following radicals: hydroxyl, halo, carboxyl, carboxy ($C_1$-$C_9$)alkyl, cyano, amino, amino substituted by one or two $C_1$-$C_4$ alkyl groups, $C_1$-$C_6$ alkoxy, $C_6$-$C_{18}$ aryl, aryloxy, the aryl group of which is a $C_6$-$C_{18}$ group, and $C_2$-$C_9$ acyloxy;

it being possible for two of the $R_1$, $R_2$, $R_3$, $R_4$, $R_5$, $R_6$, $R_7$, $R_8$, $R_9$ and $R_{10}$ radicals carried by two adjacent carbon atoms to form, together with the carbon atoms to which they are attached, a monocarbocyclic group wherein the ring is aromatic or nonaromatic or a polycarbocyclic group wherein the rings are fused or unfused and aromatic or nonaromatic, comprising from 5 to 20 ring members, it being possible for at least one carbon atom to be replaced by an oxygen, nitrogen, sulfur or phosphorus atom, the mono- or polycarbocyclic group being unsubstituted or substituted by at least one substituent chosen from a halogen atom, a hydroxyl radical, an amino radical, a carboxyl radical, a $C_6$-$C_{18}$ aryl radical, a cyano radical, a $C_1$-$C_9$ alkyl radical, a $C_1$-$C_9$ alkoxy radical, a ($C_1$-$C_9$)alkoxycarbonyl($C_1$-$C_9$)alkylamino radical and an α-naphthylalkylamino radical;

G is a divalent radical chosen from one of the formulae $G_1$ to $G_5$:

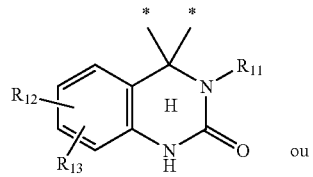

($G_1$)

ou

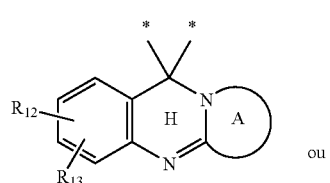

($G_2$)

ou

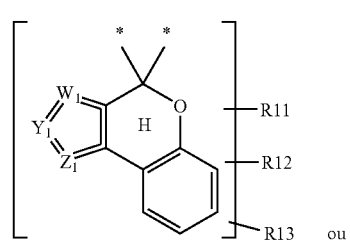

($G_3$)

ou

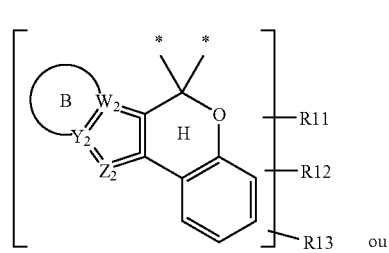

($G_4$)

ou

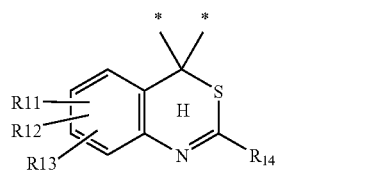

($G_5$)

wherein:

$Y_1$, $W_1$ and $Z_1$, on the one hand, and $Y_2$, $W_2$ and $Z_2$, on the other hand, are each independently chosen from sulfur atoms, carbon atoms, nitrogen atoms and divalent groups $CR_{15}$ or $NR_{15}$;

$R_{11}$, $R_{12}$, $R_{13}$ and $R_{15}$ have the same definitions as the $R_1$ to $R_{10}$ radicals;

$R_{14}$ is chosen from:

hydrogen atoms;

$C_1$-$C_9$ alkyl radicals;

amino radicals;

$C_1$-$C_9$ alkoxy radicals;

($C_1$-$C_9$)alkylthio radicals;

$C_6$-$C_{18}$ aryl radicals optionally substituted by at least one group chosen from hydroxyl, $C_1$-$C_9$ alkyl, halo, carboxyl, cyano and amino radicals;

furanyl radicals; and thienyl radicals;

it being possible for two of the $R_{11}$, $R_{12}$ and $R_{13}$ radicals carried by two adjacent carbon atoms to form, together with the carbon atoms to which they are attached, a monocarbocyclic group wherein the ring is aromatic or nonaromatic or a polycarbocyclic group wherein the rings are fused or unfused and aromatic or nonaromatic, comprising from 5 to 20 ring members, it being possible for at least one carbon atom to be replaced by an oxygen, nitrogen, sulfur or phosphorus atom, the mono- or polycarbocyclic group being unsubstituted or substituted by at least one substituent chosen from halogen atoms, hydroxyl radicals, amino radicals, carboxyl radicals, $C_6$-$C_{18}$ aryl radicals, cyano radicals, $C_1$-$C_9$ alkyl radicals and $C_1$-$C_9$ alkoxy radicals;

A is a saturated or unsaturated, substituted or unsubstituted, heterocyclic group comprising from 5 to 12 ring members;

B is chosen from $C_6$-$C_{18}$ aryl groups and heterocyclic groups comprising from 5 to 12 ring members which is saturated or unsaturated and substituted or unsubstituted; the amino radicals optionally substituted by one or two identical or different radicals chosen from $C_1$-$C_9$ alkyl radicals; $C_1$-$C_9$ hydroxyalkyl radicals; $C_2$-$C_9$ alkenyl radicals; $C_5$-$C_{12}$ cycloalkyl radicals; ($C_6$-$C_{18}$)arylcarbonyl radicals; cyclo($C_5$-$C_{12}$)alkyl($C_1$-$C_9$)alkyl radicals; ($C_1$-$C_9$)alkylcarbonyl radicals; ($C_1$-$C_9$) alkoxycarbonyl($C_1$-$C_9$)alkyl radicals; α-naphthylalkyl radicals; $C_1$-$C_9$ haloalkyl radicals; ($C_1$-$C_9$)alkylcarbonyloxy($C_1$-$C_9$)alkyl radicals; $C_1$-$C_9$ cyanoalkyl radicals; $C_2$-$C_{15}$ acyl radicals; ($C_1$-$C_6$)alkoxycarbonyl radicals; ($C_6$-$C_{18}$)aryl-oxycarbonyl radicals; ($C_6$-$C_{18}$)aryloxy ($C_1$-$C_9$)alkylcarbonyl radicals; ($C_6$-$C_{18}$)aryl($C_1$-$C_9$) alkoxycarbonyl radicals; ($C_1$-$C_9$)alkoxy($C_6$-$C_{18}$)arylcarbonyl radicals; di($C_1$-$C_9$)alkylaminocarbonyl radicals; di($C_1$-$C_9$)alkylaminosulfonyl radicals; ($C_1$-$C_9$) alkyl($C_6$-$C_{18}$)arylsulfonyl radicals; ($C_1$-$C_9$)alkylsulfonyl radicals; di($C_1$-$C_9$)alkylamino($C_1$-$C_9$)alkyl radicals; ($C_1$-$C_9$)alkoxy($C_1$-$C_9$)alkyl radicals; $C_6$-$C_{18}$ aryl radicals and ($C_6$-$C_{18}$)aryl($C_1$-$C_9$)alkyl radicals optionally substituted on the aryl nucleus by at least one substituent chosen from halogen atoms, $C_1$-$C_6$ alkyl radicals, nitro radicals, di($C_1$-$C_9$)alkylamino radicals and $C_1$-$C_9$ alkoxy radicals; it being possible for the two radicals to form, together with the nitrogen atom of the amino group, a 5- to 12-membered ring optionally carrying another heteroatom, it being possible for the said ring to be substituted by a $C_1$-$C_9$ alkyl radical.

Still another aspect of the present disclosure also relates to a method for the treatment of keratinous fibers, for example human keratinous fibers, such as the hair, comprising applying the composition to the fibers as disclosed herein.

The present disclosure may make it possible to rapidly obtain a coloring of keratinous fibres, with intense and persistent highlights which can be erased and then reformed just as rapidly. The method for erasing and reforming the color can be repeated at least once without substantial loss of color using a pH agent or by varying the temperature.

The compounds of formula (I) comprise a ring H, which can undergo opening with the formation of an acid group in the presence of protons. These compounds are colorless or weakly colored and the compounds corresponding to the opening of the ring H are colored and coloring entities. In an aqueous medium, an equilibrium is established between the colored entities and the colorless entities which depends on the pH and temperature.

When the composition comprises several compounds chosen from the compounds of formula (I), the dyes corresponding to the compounds of formula (I) wherein the ring H is open, and the addition salts thereof, the coloring of the keratinous fibers can also be modified using a pH agent or by varying the temperature.

As disclosed herein, the symbols * in the formulae ($G_1$) to ($G_5$) indicate the bonds via which the divalent radical G is attached to the aromatic nuclei substituted by the $R_1$ to $R_{10}$ radicals in the formula (I).

As used herein, "alkyl (alk) radical" is understood to mean a linear or branched radical, for example a methyl, ethyl, n-propyl, isopropyl, n-butyl or tert-butyl radical. As disclosed herein, an "alkoxy radical" is an alk-O— radical, an "alkylthio radical" is an alk-S— radical, a "mono- or dialkylamino radical" is an —N(alk)$_n$ radical with n=1 or 2, an "alkylcarbonyl radical" or an "acyl radical" is an alk-CO— radical, an "alkoxycarbonyl radical" is an alk-O—CO— radical, an "alkylcarbonylalkyl radical" is an alk-CO-alk-radical and an "alkylcarbonylamino radical" is an alk-CO—NH— radical, the alkyl radical being, in each of these definitions, as defined above.

As used herein, "alkenyl radical" is understood to mean an alkyl comprising from 2 to 10 carbon atoms and comprising at least one conjugated or nonconjugated double and/or triple bond.

As used herein, "cycloalkyl radical" is understood to mean an alkyl radical wherein the carbon atoms form a ring, for example a cyclohexyl radical. A "mono- or dicycloalkylamino radical" is an amino radical substituted by one or two cycloalkyl radicals.

As used herein, "aryl (ar) radical" is understood to mean a carbon-comprising radical derived from fused or unfused benzene compounds, for example phenyl, anthracenyl or naphthyl. As used herein, "mono- or diarylamino radical" is an amino radical substituted by one or two aryl radicals. A "mono- or di(arylalkyl)amino radical" is an amino radical substituted by one or two arylalkyl radicals. An "arylalkyl radical" is an alkyl radical substituted by an aryl radical. An "arylalkoxy radical" is an alkoxy radical substituted by an aryl radical and an "arylcarbonyl radical" is an ar-CO— radical wherein ar is as defined above.

As used herein, "heteroaryl radical" is understood to mean an aryl radical comprising at least one heteroatom, for example a pyridine ring.

As disclosed herein, a "halo radical" denotes a halogen atom chosen from chlorine, bromine, iodine and fluorine.

As used herein, "fused" means at least two rings placed side by side which exhibit at least two atoms in common.

Non-limiting examples of aromatic or nonaromatic, fused or unfused, mono- or polyheterocyclic groups comprising from 5 to 50 ring members include: thiophene, benzofuran, benzothiophene, indole, bispyridine, benzopyran, quinoline, pyrazole, pyridine, pyrrole, furan, imidazole and benzimidazole ring.

Examples of fused or unfused aromatic mono- or polycarbocyclic groups comprising from 5 to 50 ring members, wherein it being possible for one or more carbon atoms to be replaced by an oxygen, nitrogen, sulfur or phosphorus atom, include, but are not limited to benzene, naphthalene, anthracene, pyridine, quinoline, thiophene and pyrimidine rings.

As used herein, "imino radical" is an HN=C radical.

As used herein, "arylimino radical" can, by way of non-limiting example, be a phenylimino radical.

As used herein "alkoxycarbonylalkylamino radical" is an amino radical substituted by an alkoxycarbonylalkyl radical.

Also as used herein, "α-naphthylalkylamino radical" is an amino radical substituted by an α-naphthylalkyl radical, which is an alkyl radical substituted by an α-naphthyl radical.

According to at least one embodiment of the present disclosure, when A and B are substituted, then they are substituted by at least one identical or different radical $R_{16}$ having the same definition as the $R_1$ to $R_{10}$ radicals.

According to another embodiment of the present disclosure, the at least one compound of formula (I) is such that:

$R_5$ is a hydrogen atom;

$R_1$ is chosen from:

hydrogen atoms;

halogen atoms;

$C_1$-$C_9$ alkyl radicals;

$C_1$-$C_9$ alkoxy radicals;

nitro radicals;

amino radicals;

($C_1$-$C_9$)alkylthio radicals; and ($C_2$-$C_9$)acyloxy($C_1$-$C_9$)alkoxy radicals;

$R_2$ is chosen from hydrogen atoms; $C_1$-$C_9$ alkyl radicals; $C_1$-$C_9$ alkoxy radicals; halogen atoms; and amino radicals;

$R_3$ is chosen from hydrogen atoms; amino radicals; halogen atoms; ($C_6$-$C_{18}$)aryloxy($C_1$-$C_9$)alkoxy radicals; nitro radicals; and $C_1$-$C_9$ alkoxy radicals;

$R_4$ is chosen from hydrogen atoms; halogen atoms; $C_1$-$C_9$ alkyl radicals; $C_1$-$C_9$ alkoxy radicals; and ($C_1$-$C_9$)alkylthio radicals;

$R_6$ is chosen from hydrogen atoms; halogen atoms; $C_1$-$C_9$ alkyl radicals; $C_1$-$C_9$ alkoxy radicals; nitro radicals; amino radicals; and ($C_2$-$C_9$)acyloxy($C_1$-$C_9$)alkoxy radicals;

$R_7$ is chosen from hydrogen atoms; halogen atoms; $C_1$-$C_9$ alkyl radicals; and $C_1$-$C_9$ alkoxy radicals;

$R_8$ is chosen from hydrogen atoms; halogen atoms; $C_1$-$C_9$ alkyl radicals; $C_1$-$C_9$ alkoxy radicals; nitro radicals; and amino radicals;

$R_9$ is chosen from hydrogen atoms; $C_1$-$C_9$ alkyl radicals; and $C_1$-$C_9$ alkoxy radicals;

$R_{10}$ is chosen from hydrogen atoms and $C_1$-$C_9$ alkoxy radicals;

$R_{11}$ is chosen from hydrogen atoms; halogen atoms; $C_1$-$C_9$ alkyl radicals; $C_1$-$C_9$ alkoxy radicals; $C_6$-$C_{18}$ aryl radicals; amino radicals; $C_2$-$C_{18}$ acyl radicals; and ($C_6$-$C_{18}$)arylsulfonyl radicals;

$R_{12}$ is chosen from hydrogen atoms; $C_1$-$C_9$ alkyl radicals; $C_1$-$C_9$ alkoxy radicals; and amino radicals;

$R_{13}$ is a hydrogen atom; and $R_{14}$ is chosen from hydrogen atoms; amino radicals; $C_6$-$C_{18}$ aryl radicals; ($C_1$-$C_9$)alkylthio radicals; and $C_1$-$C_9$ alkoxy radicals;

it being possible for $R_1$ and $R_2$ and/or $R_2$ and $R_3$ and/or $R_6$ and $R_7$ and/or $R_7$ and $R_8$ to form, together with the carbon atoms to which they are attached, a monocarbocyclic or polycarbocyclic group wherein the rings are aromatic and fused or unfused, which comprises from 5 to 20 ring members, it being possible for at least one carbon atom to be replaced by an oxygen, nitrogen, sulfur or phosphorus atom, and which is unsubstituted or substituted, the substituents being chosen from, for example, halogen atoms and hydroxyl, amino, carboxyl, ($C_1$-$C_9$)alkoxycarbonyl($C_1$-$C_9$)alkylamino and α-napthylalkylamino radicals.

According to at least one embodiment of the present disclosure, the at least one compound of formula (I) is chosen from the compounds of formula ($I_1$):

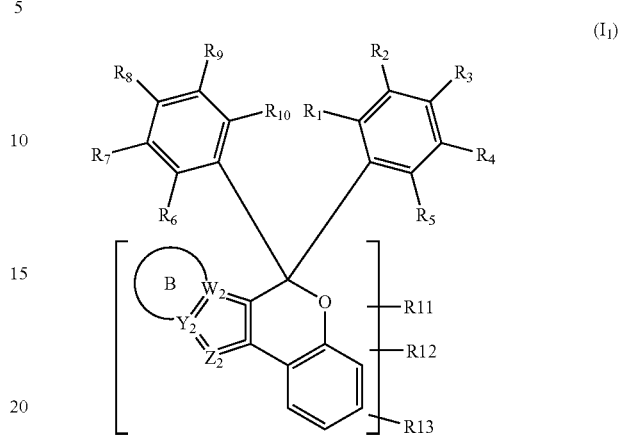

wherein:

$Y_2$, $W_2$ and $Z_2$ are each independently of one another, chosen from carbon atoms, nitrogen atoms, sulfur atoms and divalent groups $CR_{15}$ or $NR_{15}$;

B is chosen from $C_6$-$C_{18}$ aryl groups and 5- to 12-membered heterocyclic groups which are optionally saturated and optionally substituted;

$R_1$ is chosen from hydrogen atoms; halogen atoms; $C_1$-$C_9$ alkoxy radicals; $C_1$-$C_9$ alkyl radicals; nitro radicals; and ($C_1$-$C_9$)alkylthio radicals;

$R_2$ is chosen from hydrogen atoms; halogen atoms; $C_1$-$C_9$ alkyl radicals; and $C_1$-$C_9$ alkoxy radicals;

$R_3$ is chosen from hydrogen atoms; halogen atoms; nitro radicals; amino radicals; and $C_1$-$C_9$ alkoxy radicals;

$R_4$ is chosen from hydrogen atoms; $C_1$-$C_9$ alkoxy radicals; $C_1$-$C_9$ alkyl radicals; and ($C_1$-$C_9$)alkylthio radicals;

$R_5$, $R_{10}$ and $R_{13}$ are hydrogen atoms;

$R_6$ is chosen from hydrogen atoms; halogen atoms; nitro radicals; $C_1$-$C_9$ alkoxy radicals; $C_1$-$C_9$ alkyl radicals; amino radicals; and ($C_2$-$C_9$)acyloxy($C_1$-$C_9$)alkoxy radicals;

$R_7$ is chosen from hydrogen atoms and $C_1$-$C_9$ alkoxy radicals;

$R_8$ is chosen from hydrogen atoms; halogen atoms; $C_1$-$C_9$ alkoxy radicals; $C_1$-$C_9$ alkyl radicals; and amino radicals;

$R_9$ is chosen from hydrogen atoms; $C_1$-$C_9$ alkoxy radicals; and $C_1$-$C_9$ alkyl radicals;

$R_{11}$ is chosen from hydrogen atoms; halogen atoms; amino radicals; $C_1$-$C_9$ alkyl radicals; di($C_1$-$C_9$)alkylaminocarbonyl radicals; ($C_6$-$C_{18}$)arylcarbonyl radicals; ($C_6$-$C_{18}$)arylsulfonyl radicals; and $C_2$-$C_9$ acyl radicals; and $R_{12}$ is chosen from hydrogen atoms; $C_1$-$C_9$ alkyl radicals; ($C_6$-$C_{18}$)arylaminocarbonyl radicals; $C_2$-$C_{20}$ acyl radicals; and ($C_1$-$C_9$)alkoxycarbonyl radicals;

it being possible for $R_1$ and $R_2$, on the one hand, and $R_6$ and $R_7$, on the other hand, to form, together with the carbon atoms to which they are attached, an aromatic $C_6$-$C_{18}$ ring.

In at least one embodiment, $W_2$ is chosen from carbon atoms, nitrogen atoms and sulfur atoms, $Y_2$ is chosen from carbon atoms, nitrogen atoms and divalent groups $CR_{15}$, and $Z_2$ is chosen from nitrogen atoms and divalent groups $CR_{15}$ and $NR_{15}$.

According to another embodiment of the present disclosure, the at least one compound of formula (I) is chosen from the formulae $(I_2)$ to $(I_6)$:

ou

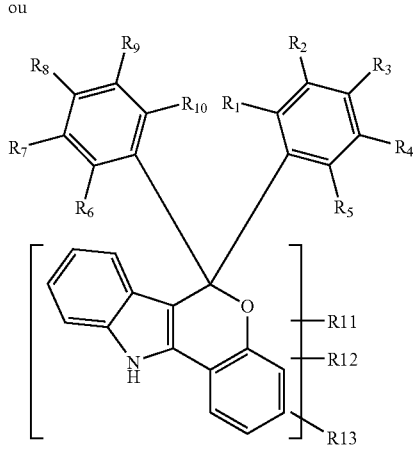

(I$_2$)

ou

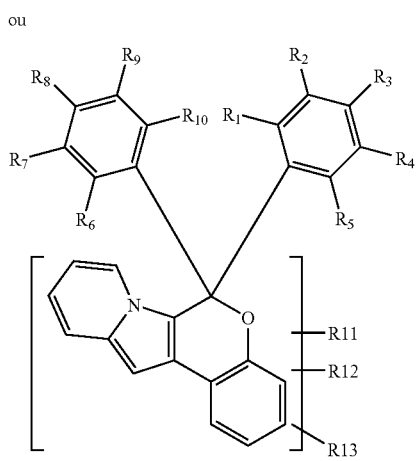

(I$_3$)

ou

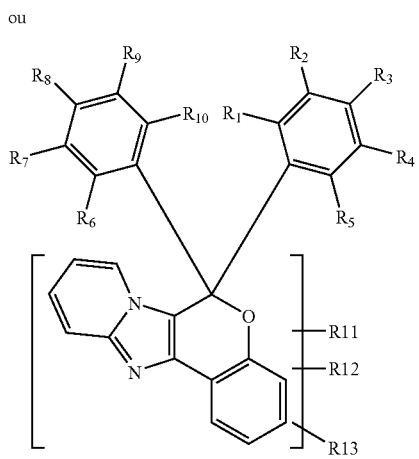

(I$_4$)

ou

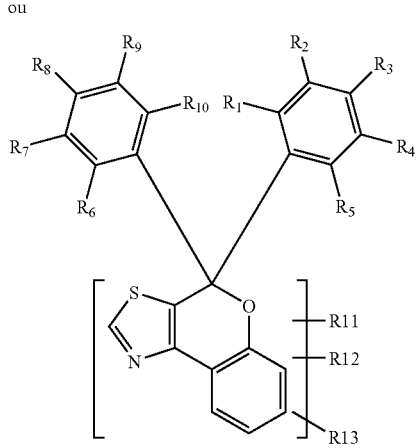

(I$_5$)

ou

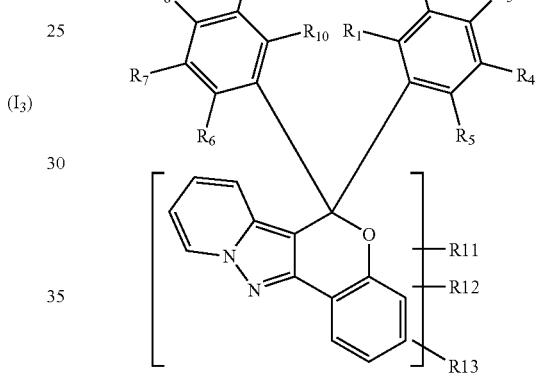

(I$_6$)

wherein:
R$_1$ is chosen from hydrogen atoms; halogen atoms; C$_1$-C$_9$ alkoxy radicals; C$_1$-C$_9$ alkyl radicals; nitro radicals; and (C$_1$-C$_9$)alkylthio radicals;

R$_2$ is chosen from hydrogen atoms; halogen atoms; C$_1$-C$_9$ alkyl radicals; and C$_1$-C$_9$ alkoxy radicals;

R$_3$ is chosen from hydrogen atoms; halogen atoms; nitro radicals; amino radicals; and C$_1$-C$_9$ alkoxy radicals;

R$_4$ is chosen from hydrogen atoms; C$_1$-C$_9$ alkoxy radicals; C$_1$-C$_9$ alkyl radicals; and (C$_1$-C$_9$)alkylthio radicals;

R$_5$, R$_{10}$ and R$_{13}$ are hydrogen atoms;

R$_6$ is chosen from hydrogen atoms; halogen atoms; nitro radicals; C$_1$-C$_9$ alkoxy radicals; C$_1$-C$_9$ alkyl radicals; amino radicals; and (C$_2$-C$_9$)acyloxy(C$_1$-C$_9$)alkoxy radicals;

R$_7$ is chosen from hydrogen atoms and C$_1$-C$_9$ alkoxy radicals;

R$_8$ is chosen from hydrogen atoms; halogen atoms; C$_1$-C$_9$ alkoxy radicals; C$_1$-C$_9$ alkyl radicals; and amino radicals;

R$_9$ is chosen from hydrogen atoms; C$_1$-C$_9$ alkoxy radicals; and C$_1$-C$_9$ alkyl radicals;

R$_{11}$ is chosen from hydrogen atoms; halogen atoms; amino radicals; C$_1$-C$_9$ alkyl radicals; di(C$_1$-C$_9$)alkylaminocarbonyl radicals; (C$_6$-C$_{18}$)arylcarbonyl radicals; (C$_6$-C$_{18}$)arylsulfonyl radicals; and C$_2$-C$_9$ acyl radicals; and $R_{12}$ is chosen from hydrogen atoms; $C_1$-$C_9$ alkyl radicals; ($C_6$-$C_{18}$)arylaminocarbonyl radicals; $C_2$-$C_{20}$ acyl radicals; and ($C_1$-$C_9$)alkoxycarbonyl radicals;

it being possible for $R_1$ and $R_2$, on the one hand, and $R_6$ and $R_7$, on the other hand, to form, together with the carbon atoms to which they are attached, an aromatic $C_6$-$C_{18}$ ring.

According to yet another embodiment of the present disclosure, the at least one compound of formula (I) is chosen from the compounds of formula ($I_7$):

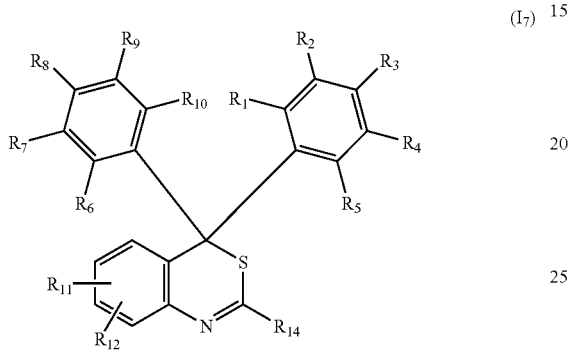

(I₇)

wherein:

- $R_1$ is chosen from hydrogen atoms; halogen atoms; and $C_1$-$C_9$ alkoxy radicals;
- $R_2$ is chosen from hydrogen atoms; halogen atoms; $C_1$-$C_9$ alkyl radicals; and $C_1$-$C_9$ alkoxy radicals;
- $R_3$ is chosen from hydrogen atoms and amino radicals;
- $R_4$, $R_5$, $R_9$ and $R_{10}$ are hydrogen atoms;
- $R_6$ is chosen from hydrogen atoms; halogen atoms; and $C_1$-$C_9$ alkoxy radicals;
- $R_7$ is chosen from hydrogen atoms; halogen atoms; $C_1$-$C_9$ alkyl radicals; and $C_1$-$C_9$ alkoxy radicals;
- $R_8$ is chosen from hydrogen atoms and amino radicals;
- $R_{11}$ is chosen from hydrogen atoms; $C_1$-$C_9$ alkyl radicals; $C_1$-$C_9$ alkoxy radicals; amino radicals; and $C_6$-$C_{18}$ aryl radicals;
- $R_{12}$ is chosen from hydrogen atoms; $C_1$-$C_9$ alkyl radicals; and $C_1$-$C_9$ alkoxy radicals; and
- $R_{14}$ is chosen from hydrogen atoms; amino radicals; $C_6$-$C_{18}$ aryl radicals; ($C_1$-$C_9$)alkylthio radicals; and $C_1$-$C_9$ alkoxy radicals;

it being possible for $R_1$ and $R_2$ and/or $R_2$ and $R_3$ and/or $R_7$ and $R_8$ and/or $R_{11}$ and $R_{12}$ to form, together with the carbon atoms to which they are attached, a $C_6$-$C_{18}$ aromatic ring or a heterocycle comprising from 5 to 12 ring members.

According to yet another embodiment of the present disclosure, the at least one compound of formula (I) is chosen from the compounds of formula ($I_8$):

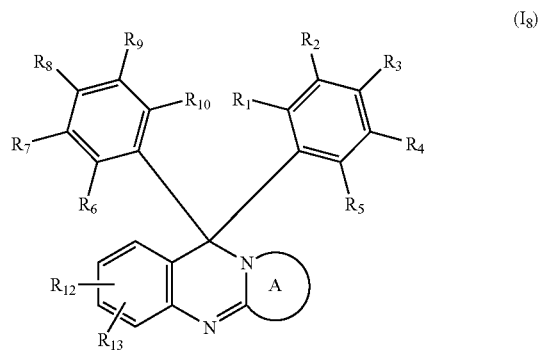

(I₈)

wherein:

A is chosen from $C_6$-$C_{18}$ aryl groups and saturated or unsaturated, substituted or unsubstituted, 5- to 12-membered heterocyclic groups comprising at least two heteroatoms, including the nitrogen atom belonging to the condensed ring;

$R_1$, $R_2$, $R_4$, $R_5$, $R_6$, $R_7$, $R_9$, $R_{10}$ and $R_{13}$ are hydrogen atoms; and $R_3$, $R_8$ and $R_{12}$ are each independently of one another, chosen from hydrogen atoms and amino radicals.

In at least one embodiment of the present disclosure, the formula ($G_2$) is chosen from either of the following formulae:

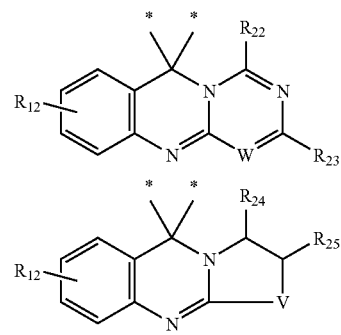

wherein:

$R_{22}$ and $R_{23}$ are each independently of one another, chosen from amino radicals; $C_1$-$C_9$ alkyl radicals; and $C_1$-$C_9$ alkoxy radicals;

W is chosen from nitrogen atoms and $CR_{26}$ groups;

V is chosen from sulfur atoms and oxygen atoms;

$R_{24}$ and $R_{25}$ are hydrogen atoms or form, with one another and with the carbon atoms to which they are attached, a benzene ring;

$R_{12}$ is chosen from hydrogen atoms; $C_1$-$C_9$ alkyl radicals; $C_1$-$C_9$ alkoxy radicals; and amino radicals; and $R_{26}$ is a hydrogen atom or can form, with $R_{23}$ and the carbon atoms to which they are attached, a benzene ring.

According to yet another embodiment of the present disclosure, the at least one compound of formula (I) is chosen from the compounds of formula (I$_9$):

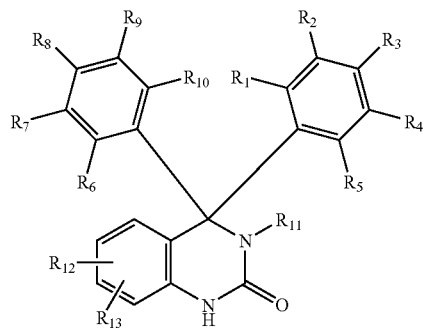

wherein:
$R_1$, $R_2$, $R_4$, $R_5$, $R_6$, $R_7$, $R_9$ and $R_{10}$ are hydrogen atoms;
$R_3$ is chosen from hydrogen atoms and amino radicals;
$R_8$ is chosen from hydrogen atoms; $C_1$-$C_9$ alkoxy radicals; and amino radicals;
$R_{11}$ is chosen from hydrogen atoms; $C_2$-$C_{18}$ acyl radicals; ($C_6$-$C_{18}$)arylsulfonyl radicals; and ($C_6$-$C_{18}$)arylcarbonyl radicals;
$R_{12}$ is chosen from hydrogen atoms; $C_1$-$C_9$ alkoxy radicals; and amino radicals; and
$R_{13}$ is chosen from hydrogen atoms and $C_1$-$C_9$ alkyl radicals.

For the formulae (I$_1$) to (I$_9$), "amino radical" is understood to mean an amino radical which is unsubstituted or substituted by one or two identical or different radicals chosen from $C_1$-$C_9$ alkyl radicals; $C_1$-$C_9$ hydroxyalkyl radicals; $C_2$-$C_9$ alkenyl radicals; $C_5$-$C_{12}$ cycloalkyl radicals; ($C_6$-$C_{18}$)arylcarbonyl radicals; cyclo($C_5$-$C_{12}$)alkyl($C_1$-$C_9$)alkyl radicals; ($C_1$-$C_9$)alkylcarbonyl radicals; ($C_1$-$C_9$)alkoxycarbonyl($C_1$-$C_9$) alkyl radicals; α-naphthylalkyl radicals; $C_1$-$C_9$ haloalkyl radicals; ($C_1$-$C_9$)alkylcarbonyloxy($C_1$-$C_9$)alkyl radicals; $C_1$-$C_9$ cyanoalkyl radicals; $C_2$-$C_{15}$ acyl radicals; ($C_1$-$C_9$) alkoxycarbonyl radicals; ($C_6$-$C_{18}$)aryloxycarbonyl radicals; ($C_6$-$C_{18}$)aryloxy($C_1$-$C_9$)alkylcarbonyl radicals; ($C_6$-$C_{18}$)aryl($C_1$-$C_9$)alkoxycarbonyl radicals; ($C_1$-$C_9$)alkoxy($C_6$-$C_{18}$) arylcarbonyl radicals; di($C_1$-$C_9$)alkylaminocarbonyl radicals; di($C_1$-$C_9$)alkylaminosulfonyl radicals; ($C_1$-$C_9$)alkyl ($C_6$-$C_{18}$)arylsulfonyl radicals; ($C_1$-$C_9$)alkylsulfonyl radicals; di($C_1$-$C_9$)alkylamino($C_1$-$C_9$)alkyl radicals; ($C_1$-$C_9$)alkoxy ($C_1$-$C_9$)alkyl radicals; $C_6$-$C_{18}$ aryl radicals and ($C_6$-$C_{18}$)aryl ($C_1$-$C_9$)alkyl radicals optionally substituted on the aryl nucleus by at least one substituent chosen from halogen atoms, $C_1$-$C_9$ alkyl radicals, nitro radicals, di($C_1$-$C_9$)alkylamino radicals and $C_1$-$C_9$ alkoxy radicals; it being possible for the two radicals to form, together with the nitrogen atom of the amino group, a 5- to 12-membered ring optionally carrying another heteroatom, it being possible for the ring to be substituted by a $C_1$-$C_9$ alkyl radical.

For the formulae (I$_1$) to (I$_9$), "aryl radical" is understood to mean an aryl radical which is unsubstituted or substituted by at least one group chosen from hydroxyl, $C_1$-$C_9$ alkyl, halo, carboxyl, cyano and amino radicals.

For the formulae (I$_1$) to (I$_9$), "alkyl radical" is understood to mean an alkyl radical which is unsubstituted or substituted by a halogen atom, a hydroxyl radical, an amino radical, an amino radical substituted by one or two $C_1$-$C_4$ alkyl groups, carboxyl radicals, $C_6$-$C_{18}$ aryl radicals, cyano radicals, $C_1$-$C_9$ alkoxy radicals, aryloxy radicals, the aryl group of which is a $C_6$-$C_{18}$ group, and $C_2$-$C_9$ acyloxy radicals.

Non-limiting mention may be made, as examples of the at least one compound of formula (I), of the following compounds:

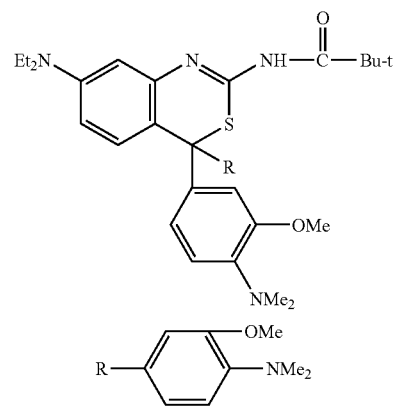

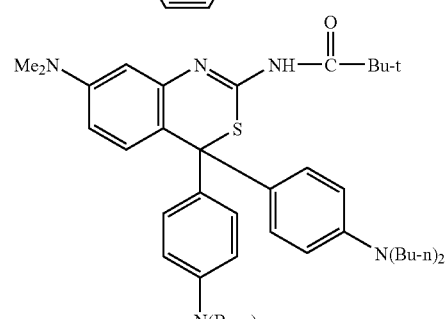

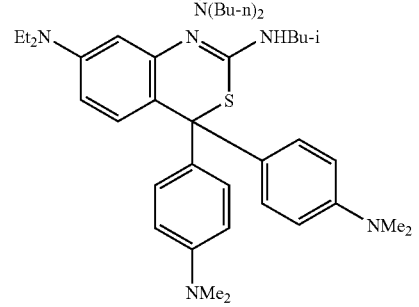

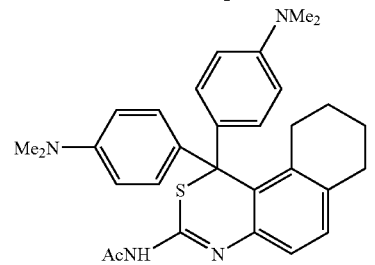

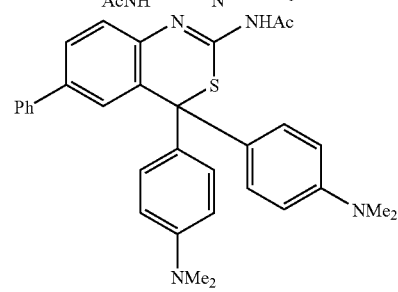

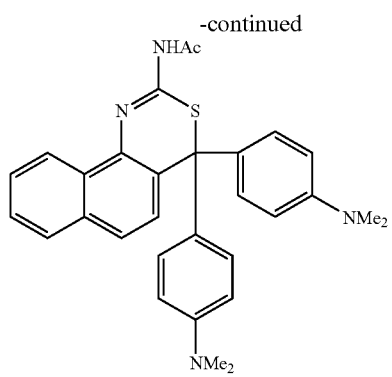
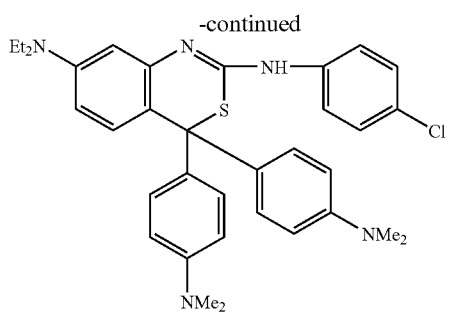
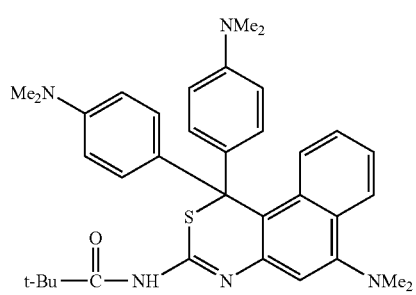
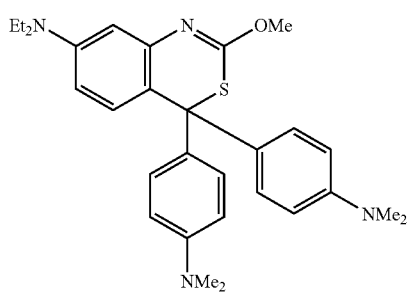
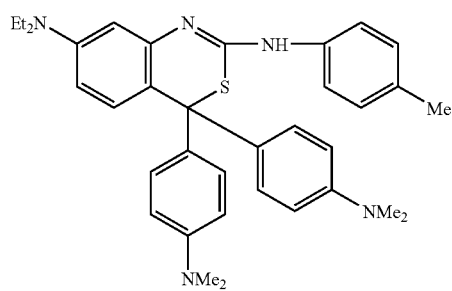
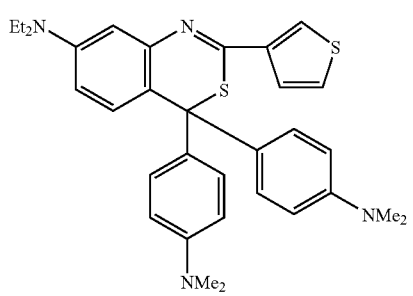
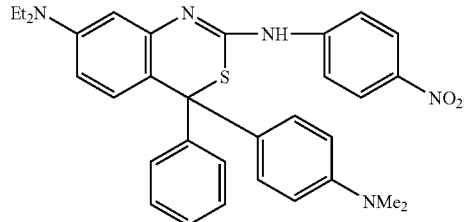
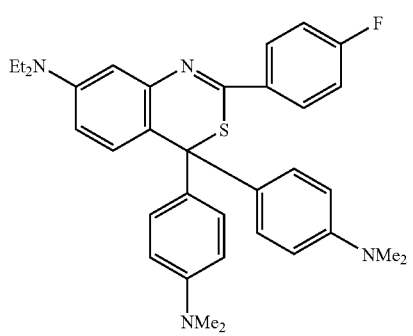
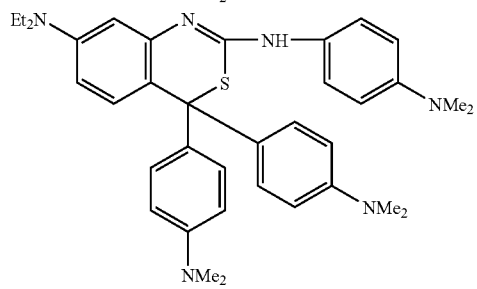
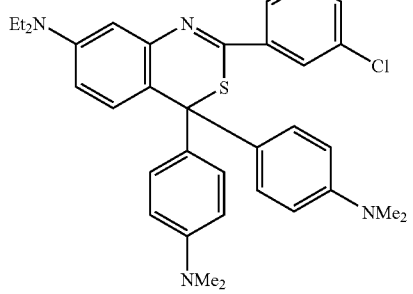

-continued
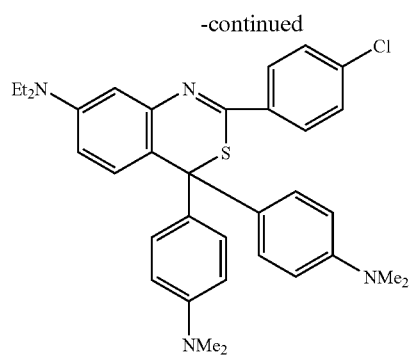
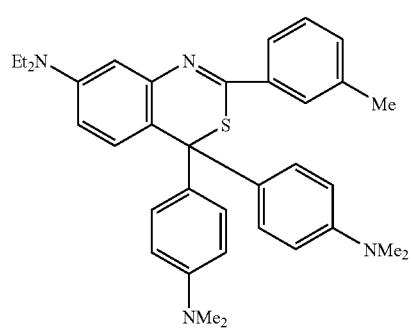
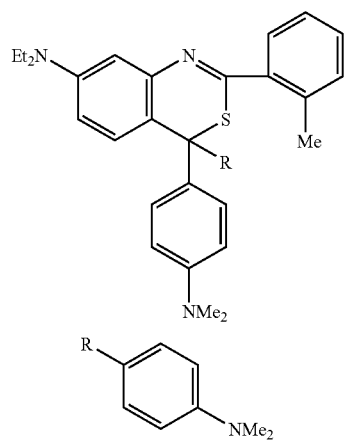
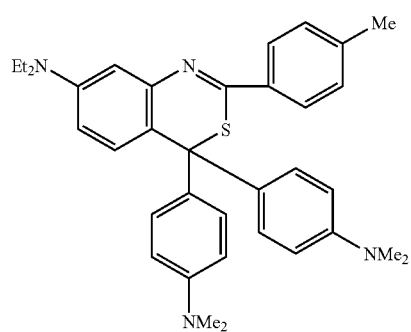
-continued
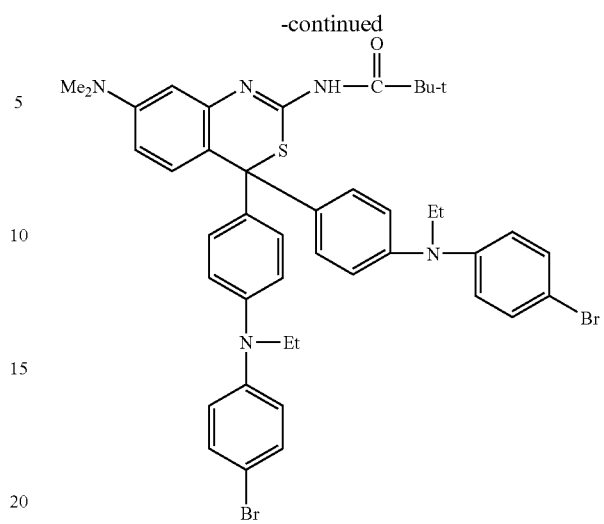
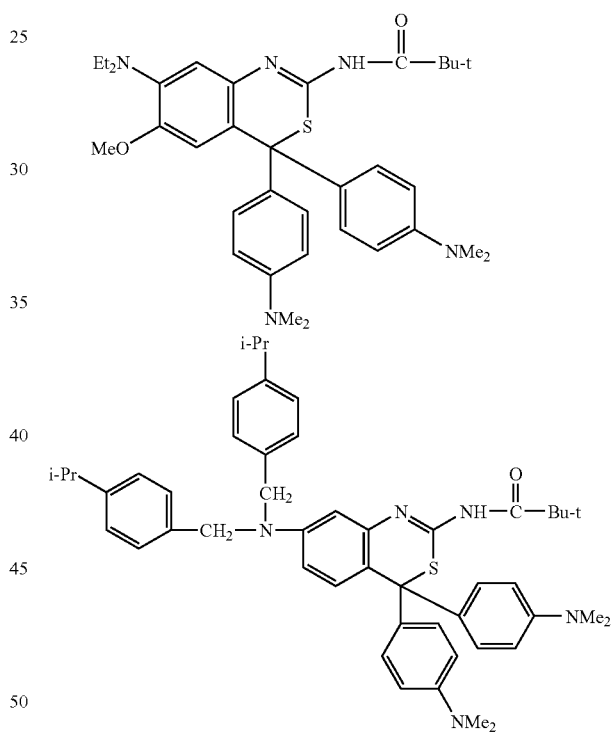
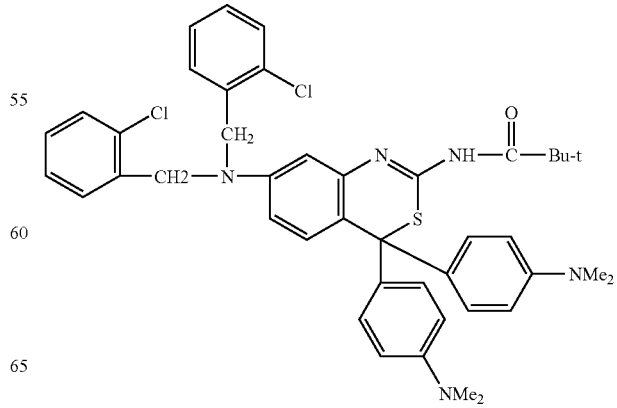

-continued
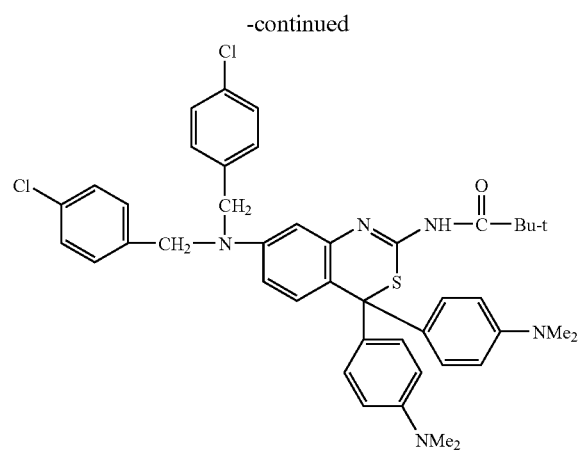
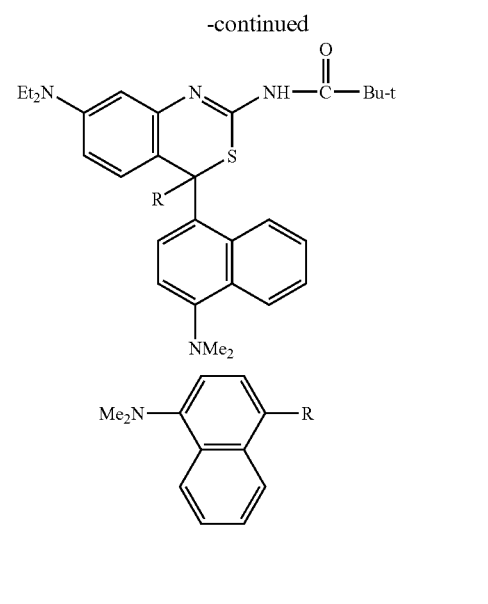
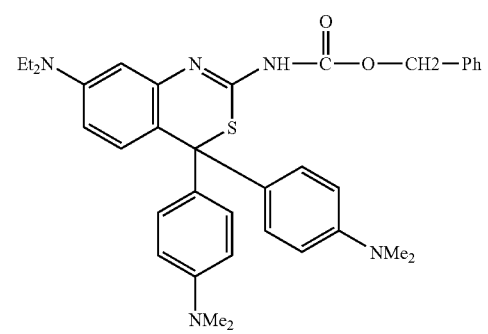
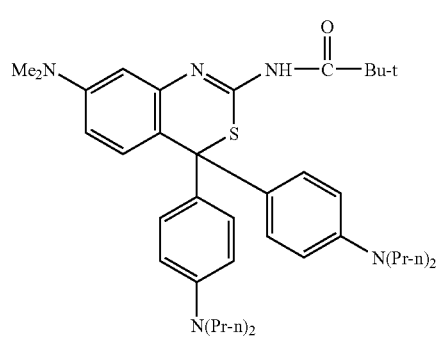
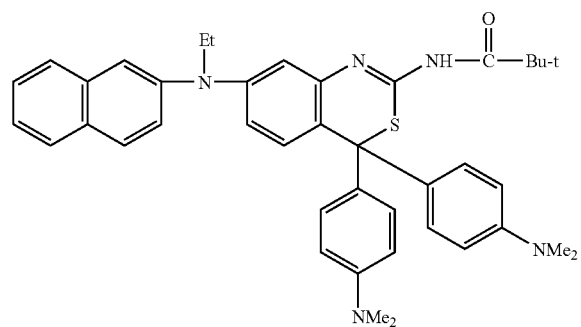
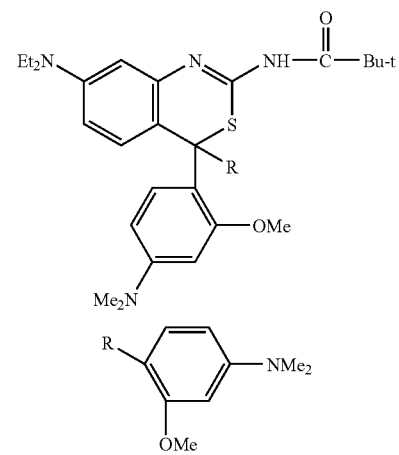

-continued
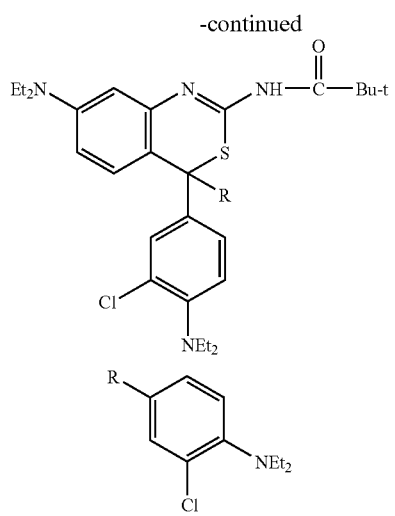
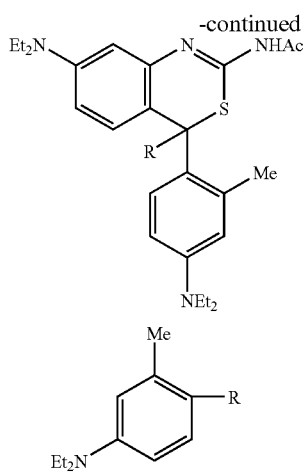
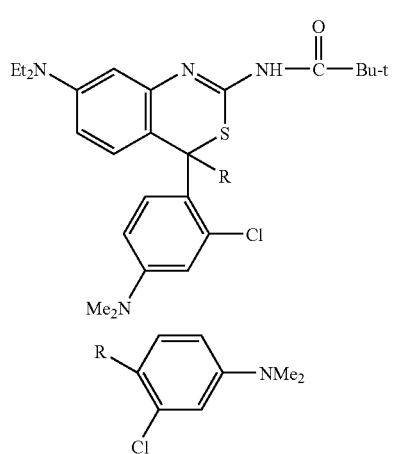
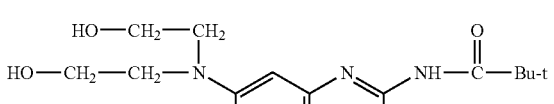
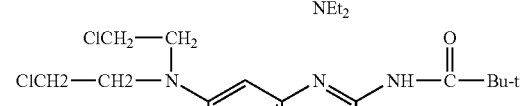
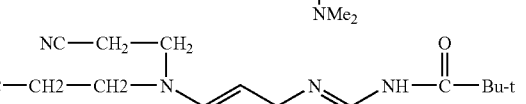
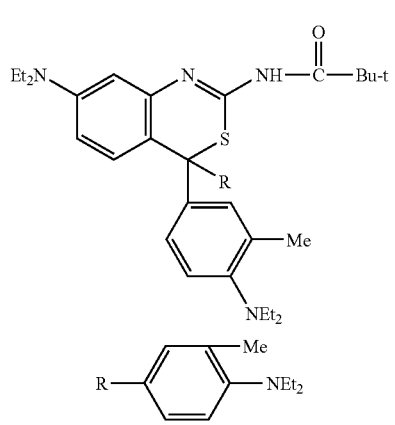
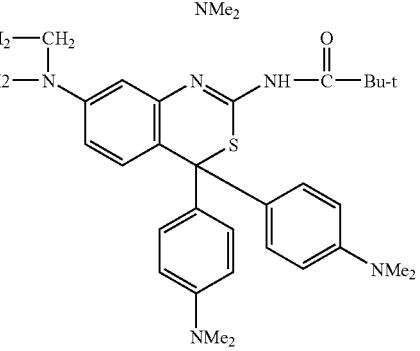

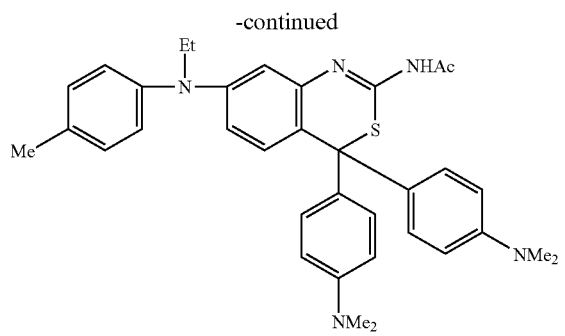
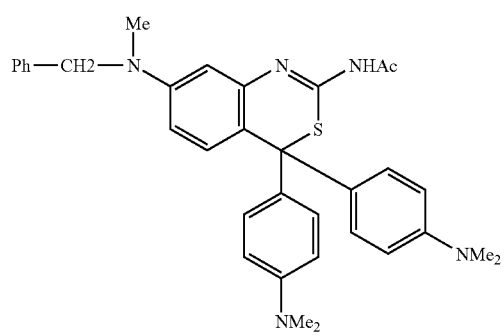
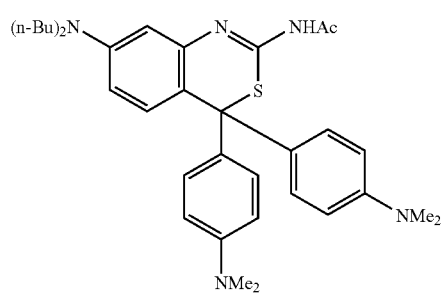
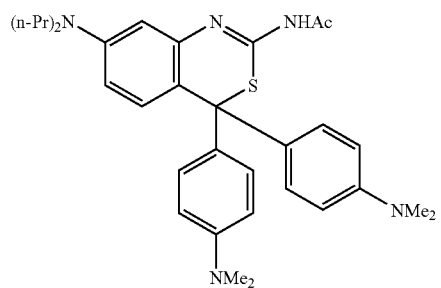
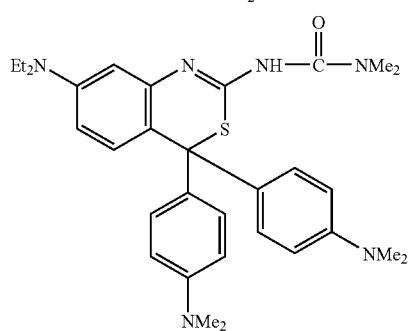
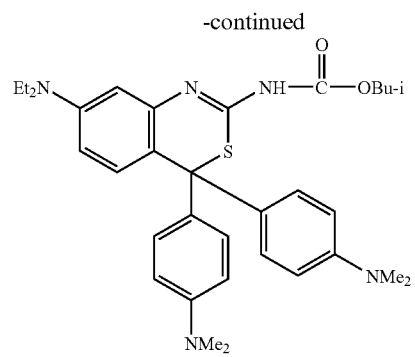
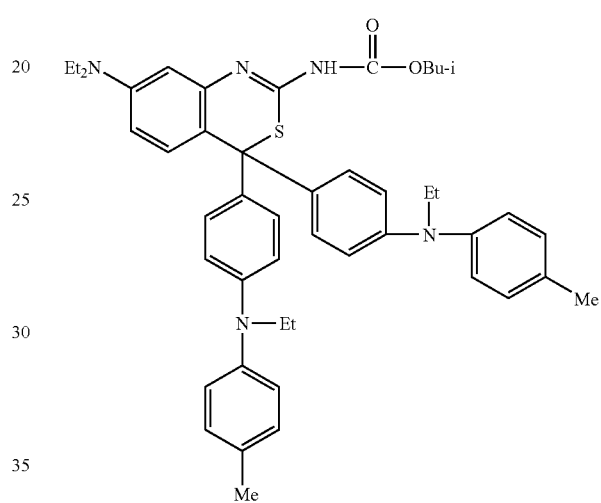
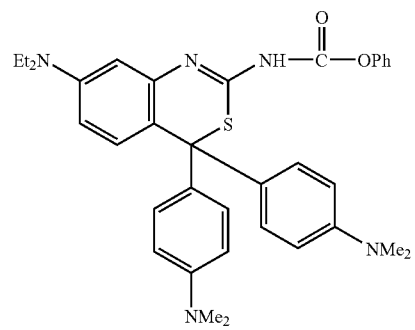
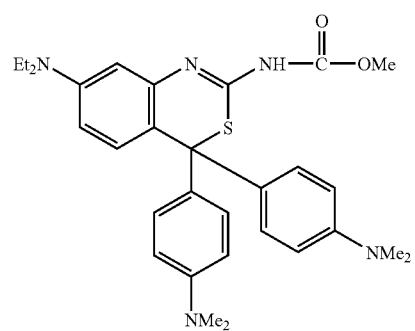

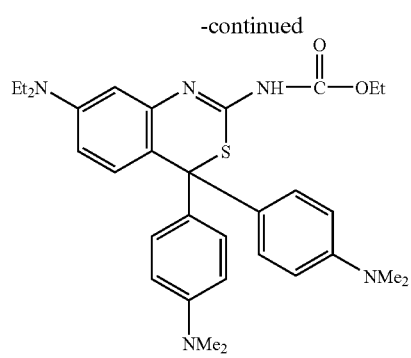
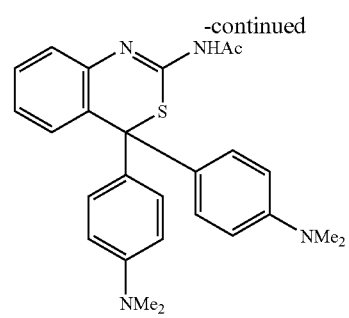
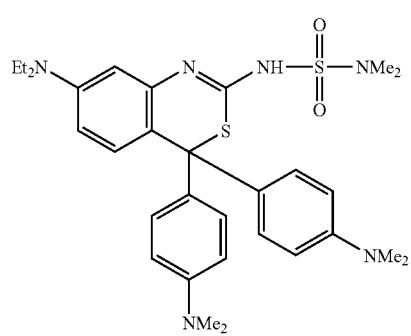
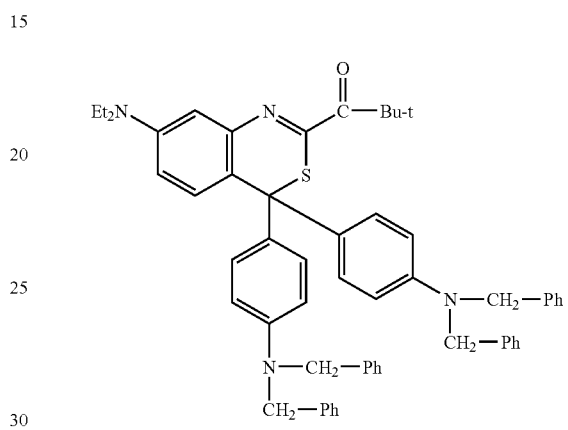
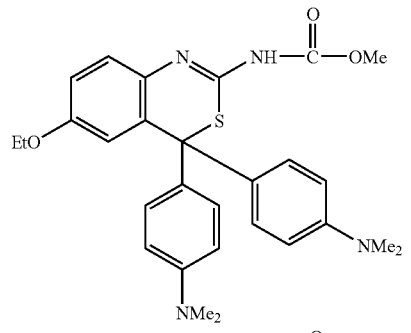
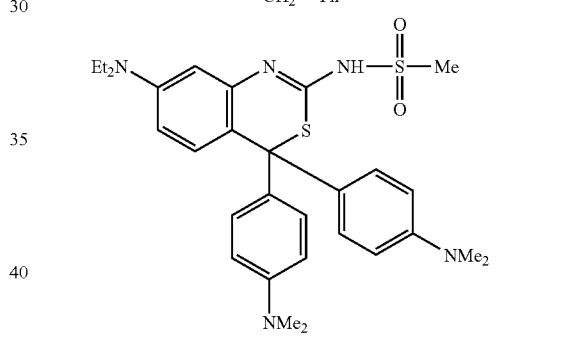
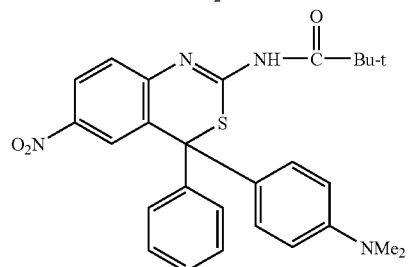
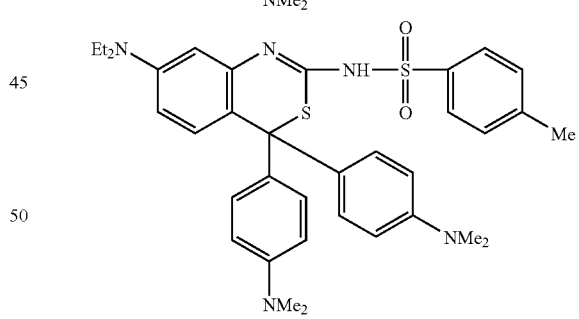
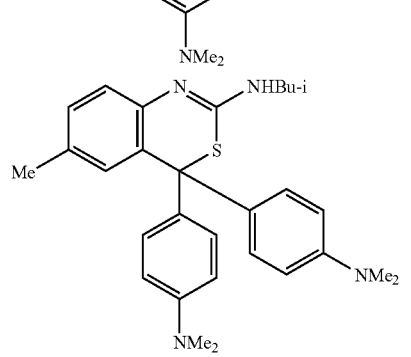
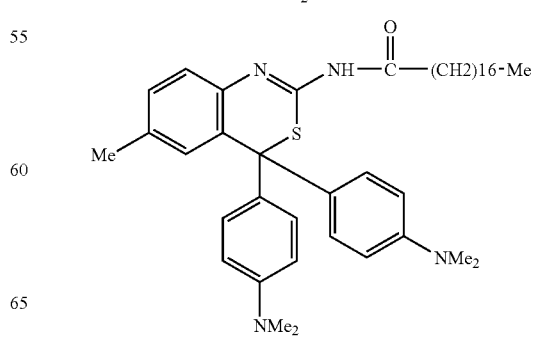

-continued
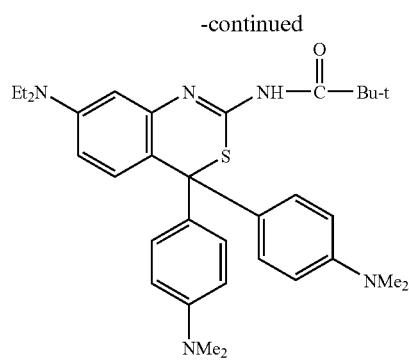
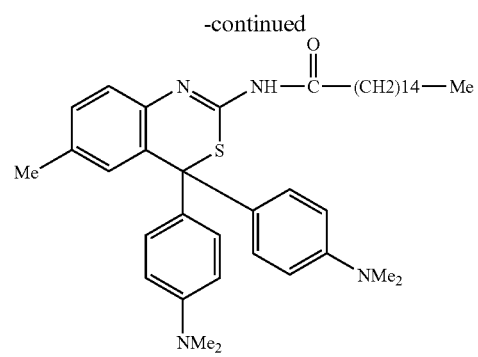
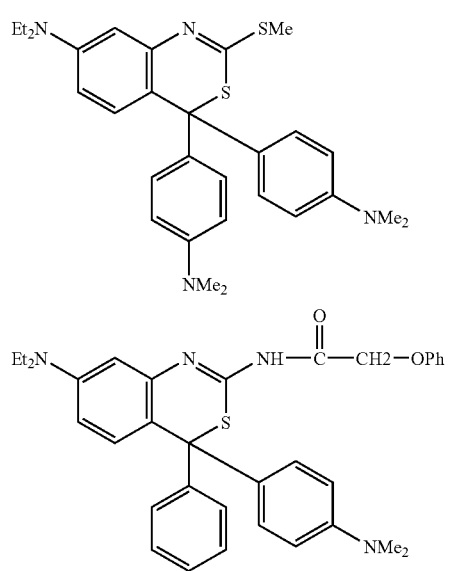
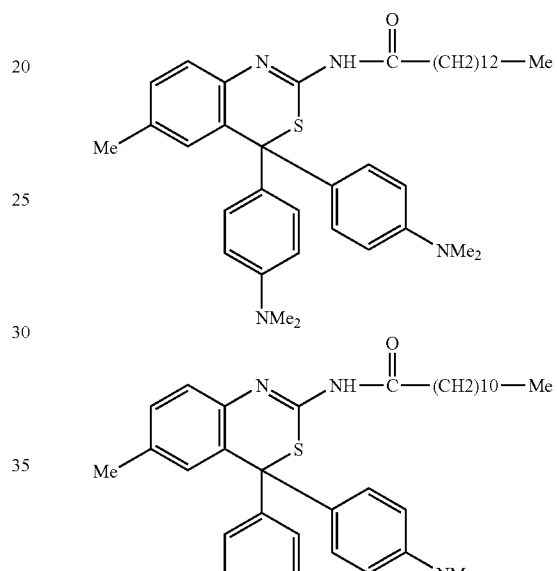
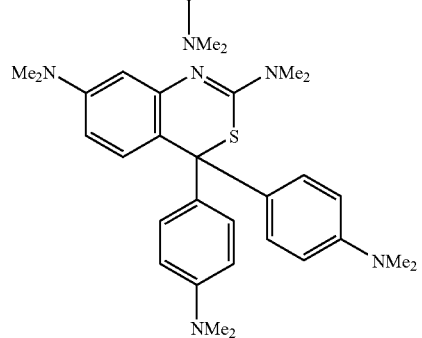
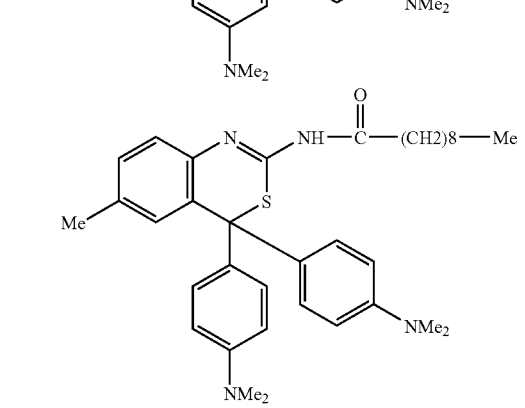
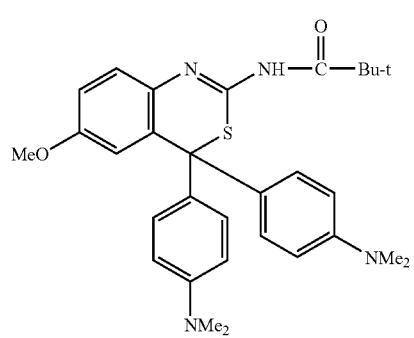
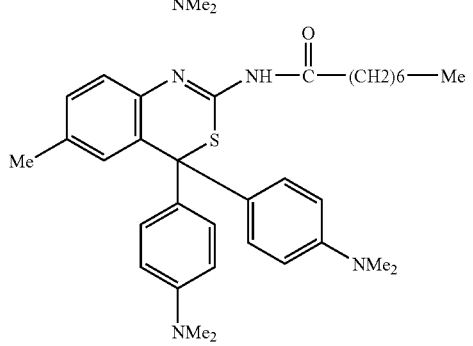

-continued
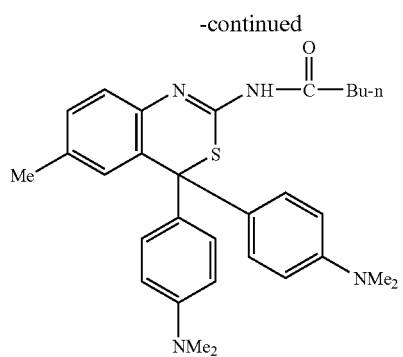
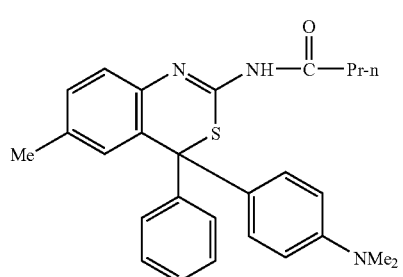
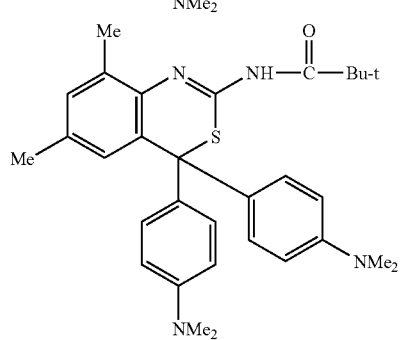
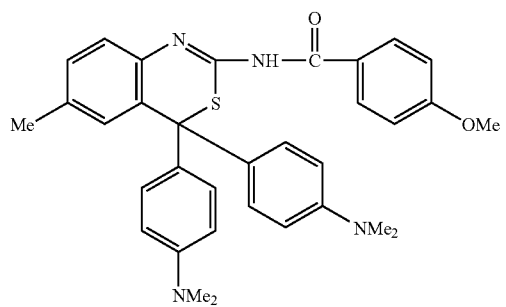
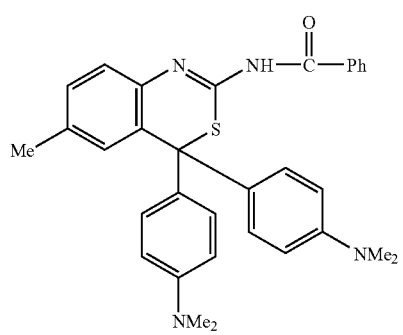
-continued
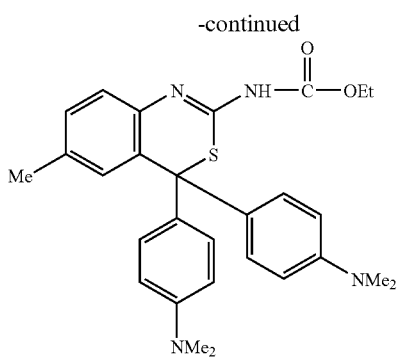
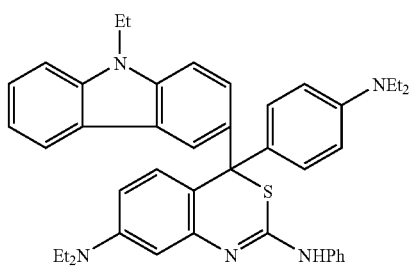
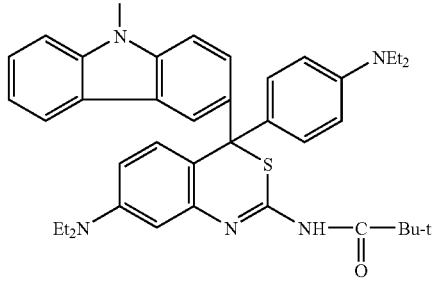
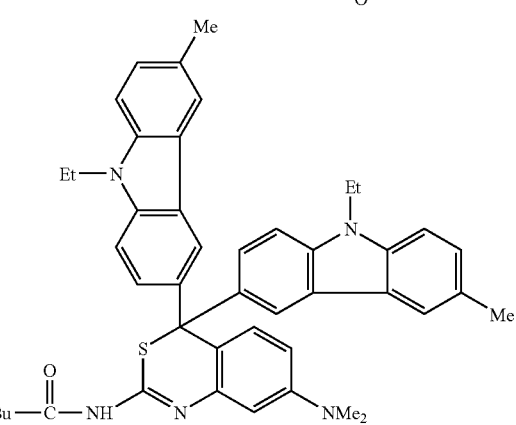
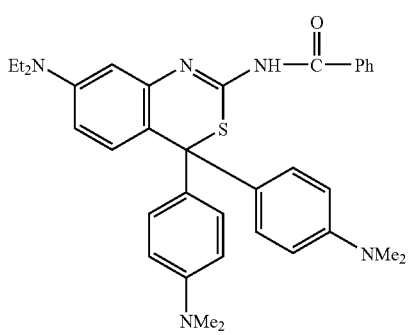

-continued
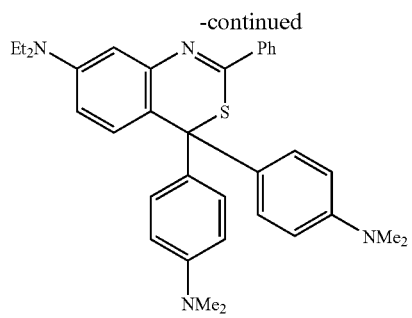
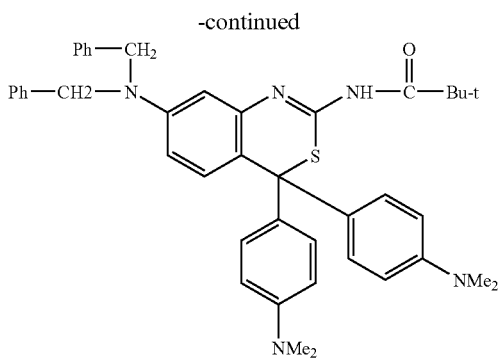
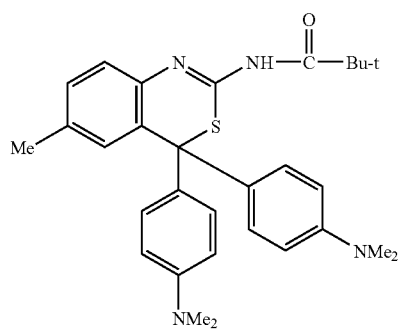
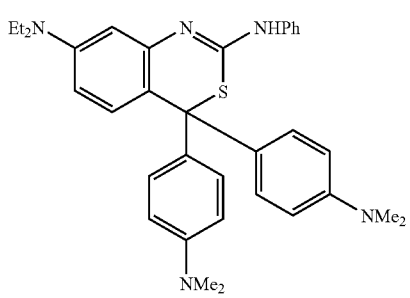
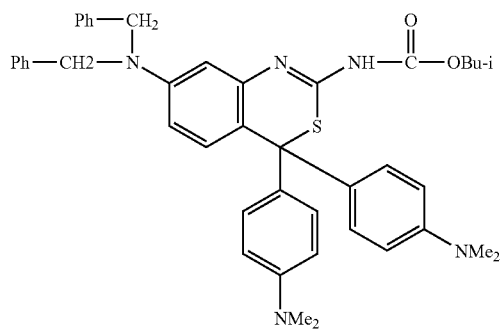
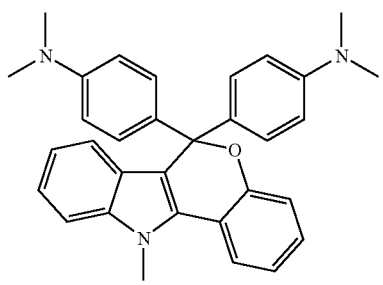
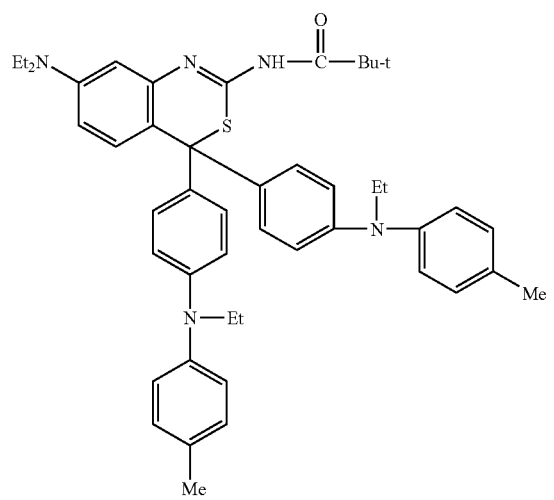
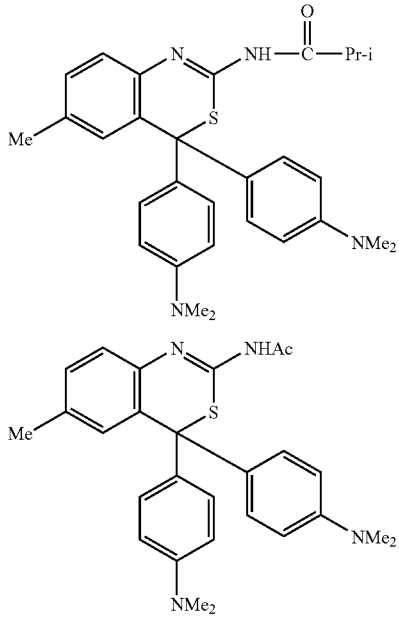

33
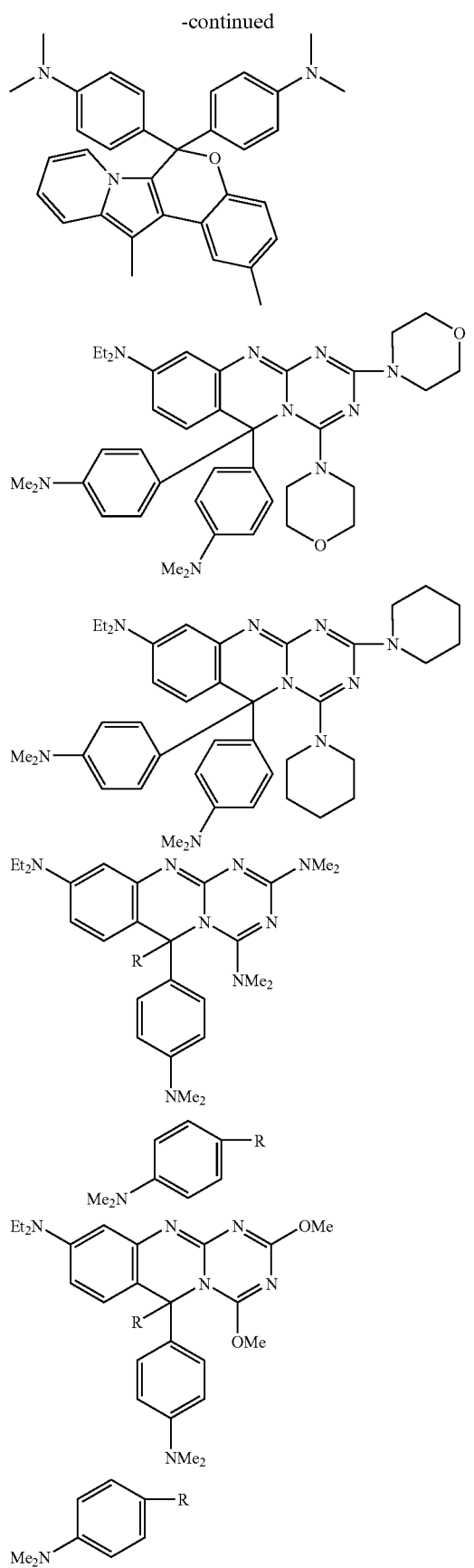
34
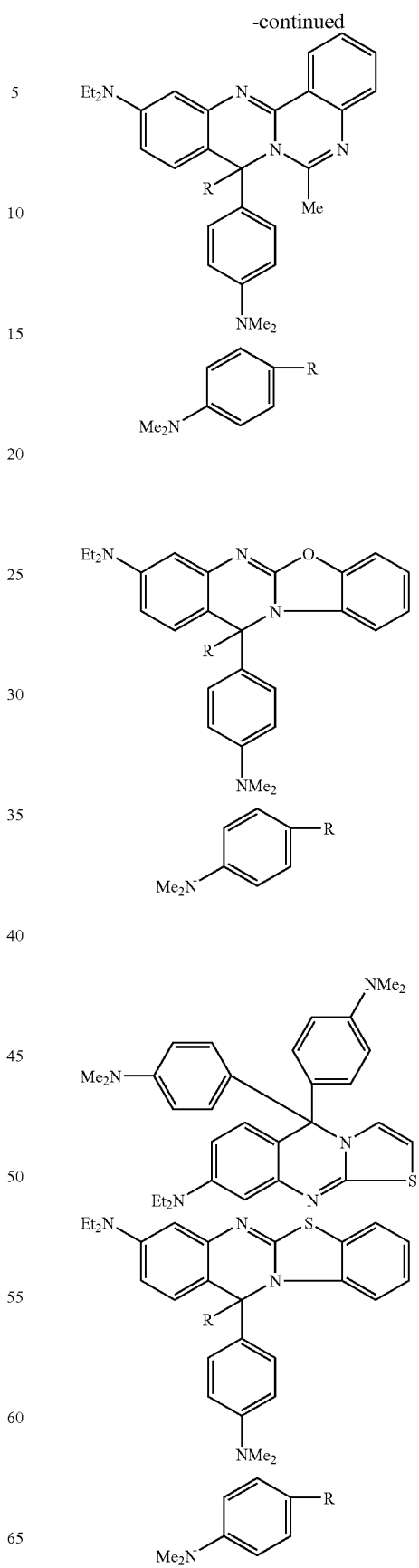

-continued
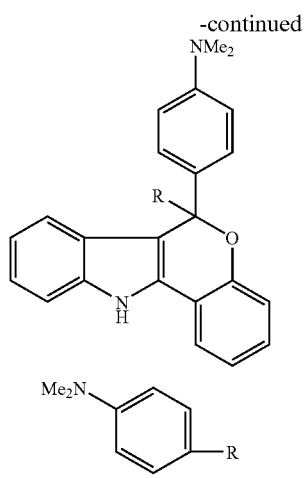
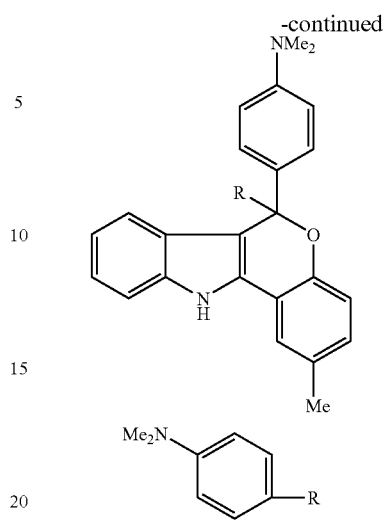
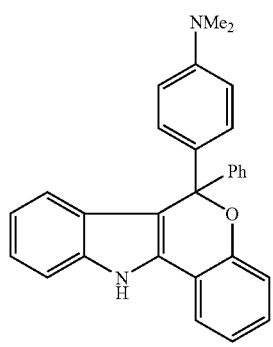
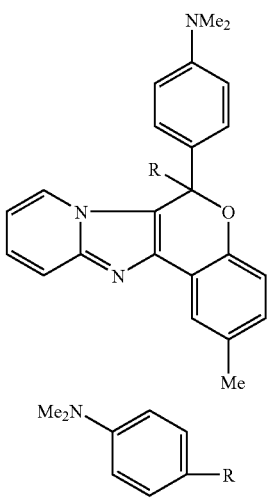
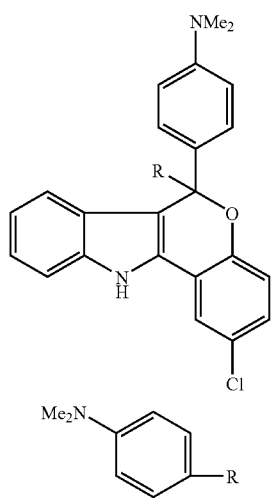
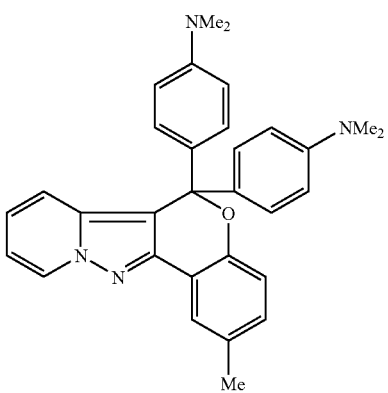

-continued
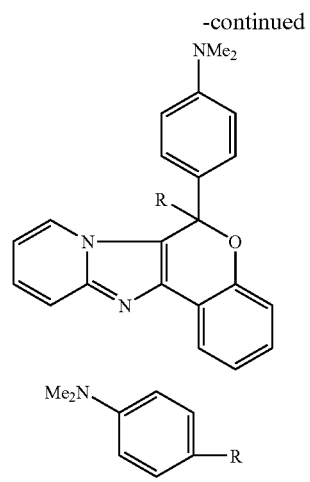
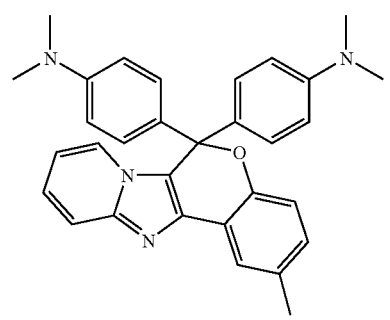
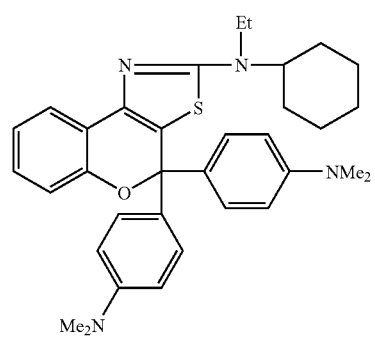
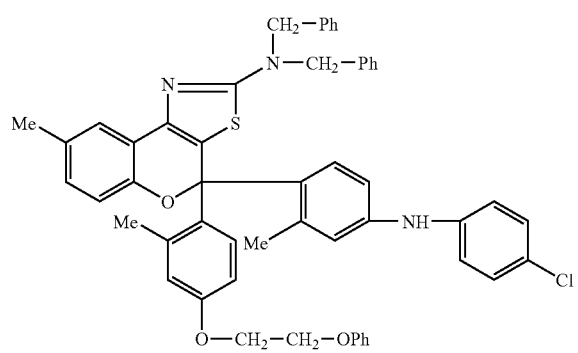
-continued
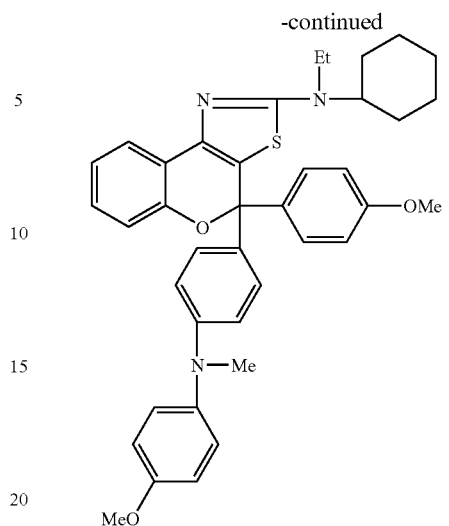
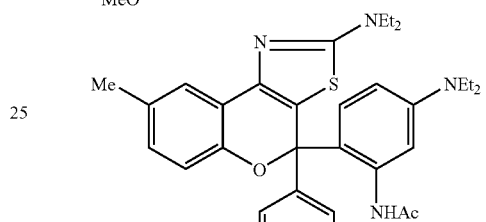
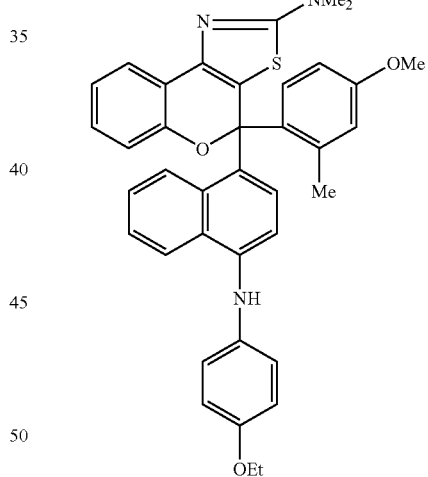
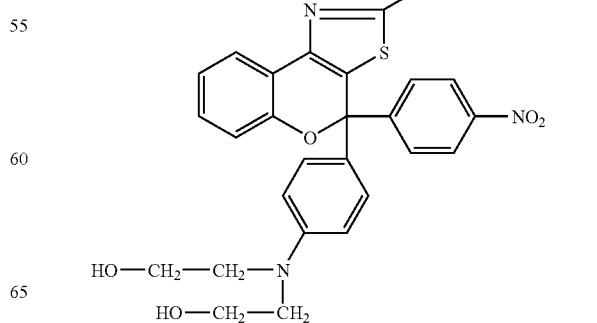

-continued
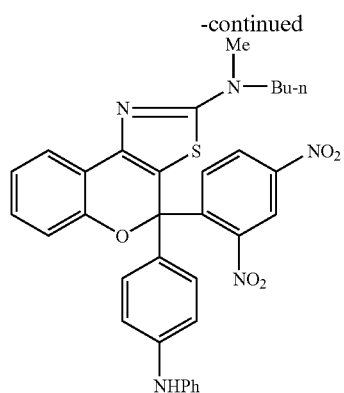
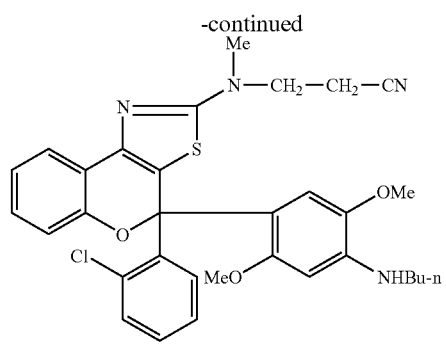
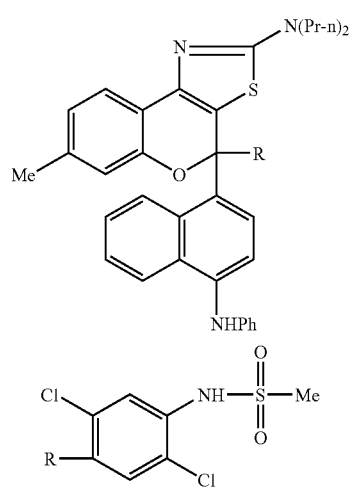
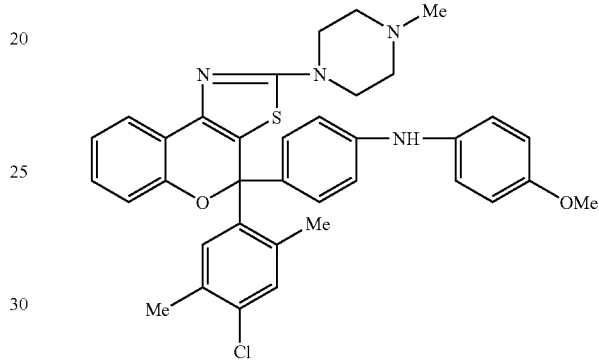
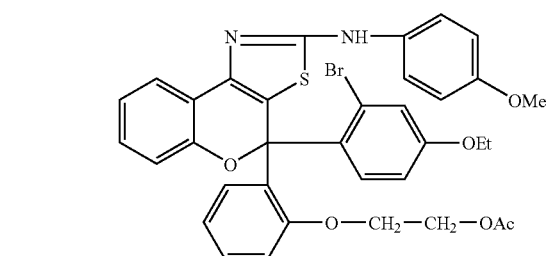
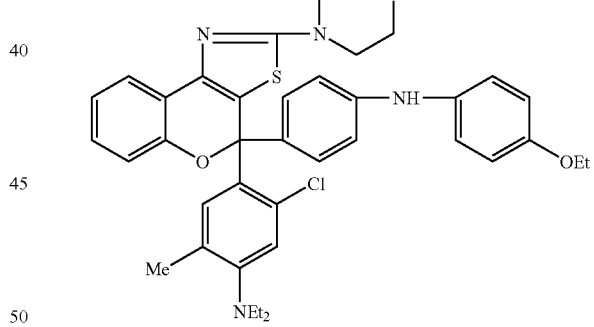
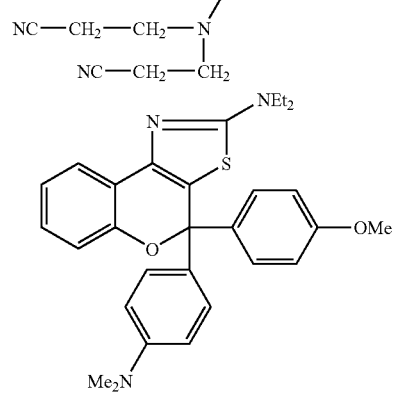
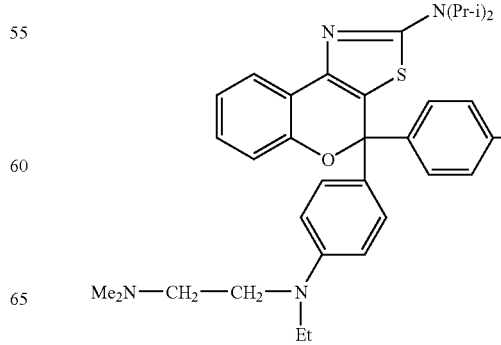

-continued
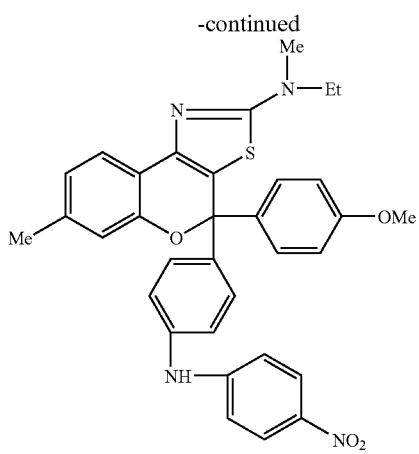
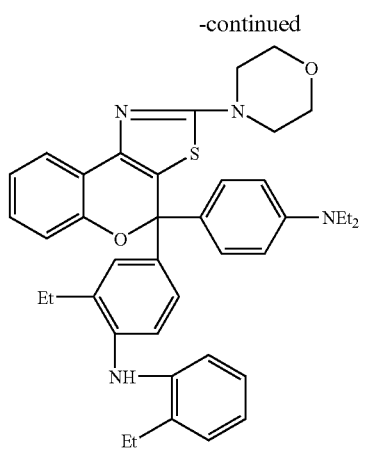
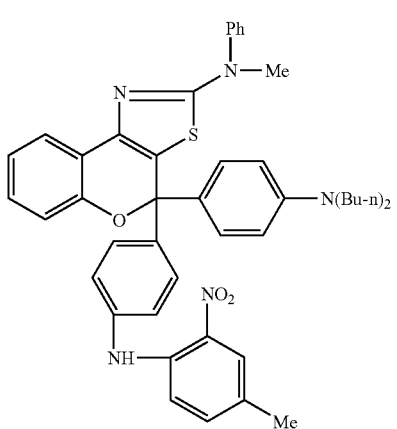
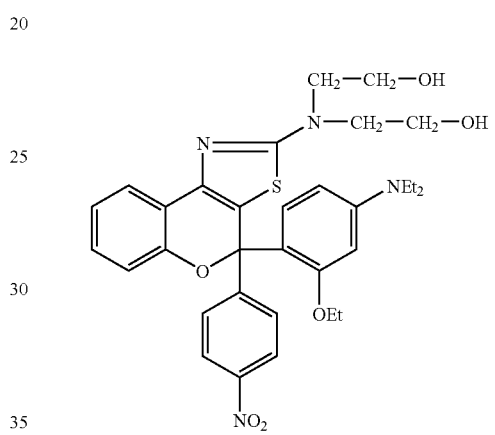
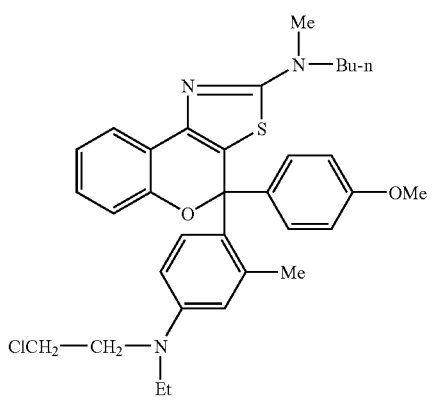
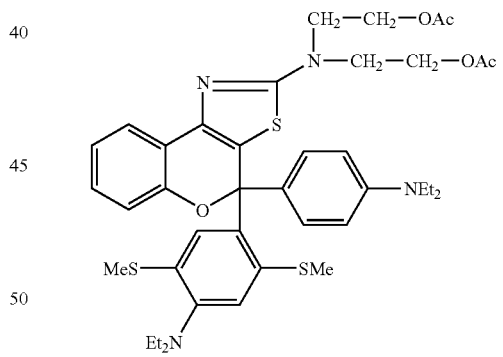
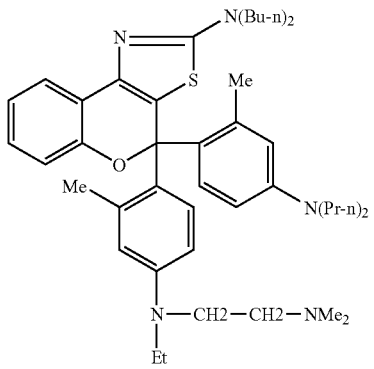
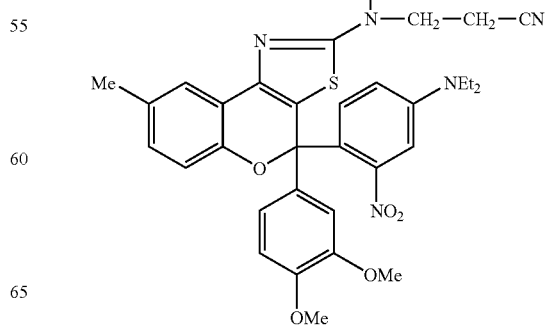

-continued
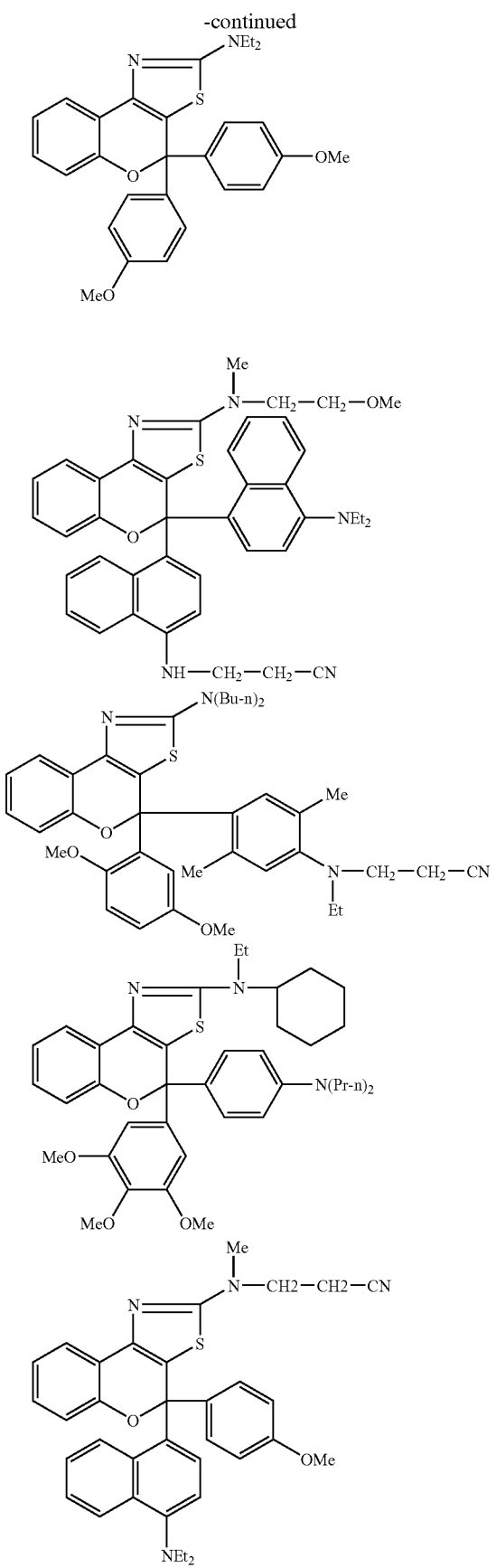
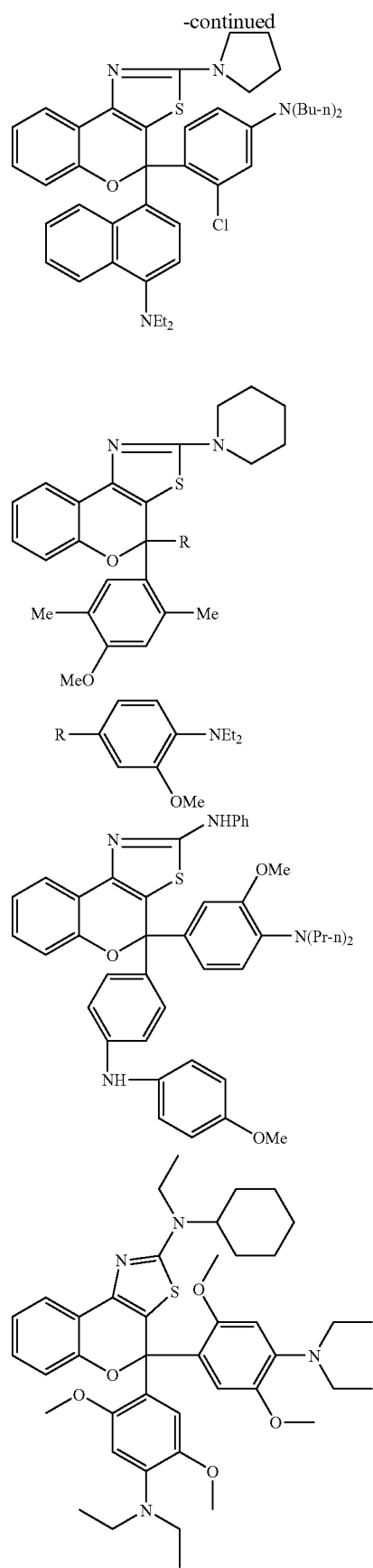

-continued
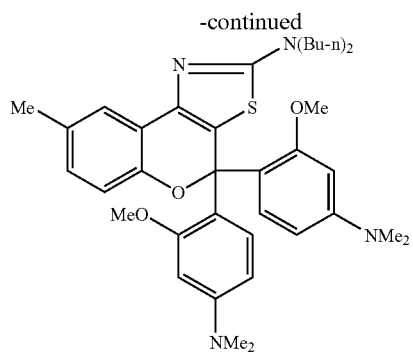
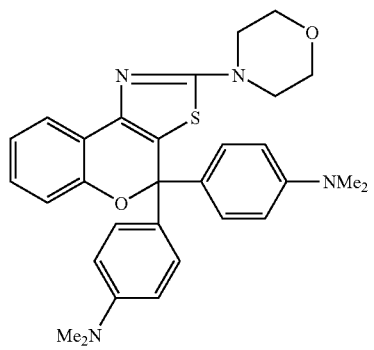
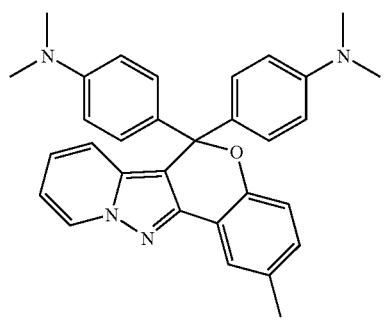
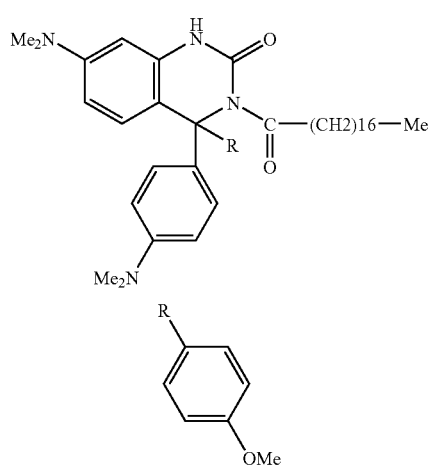
-continued
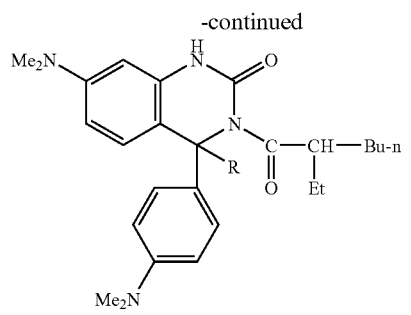
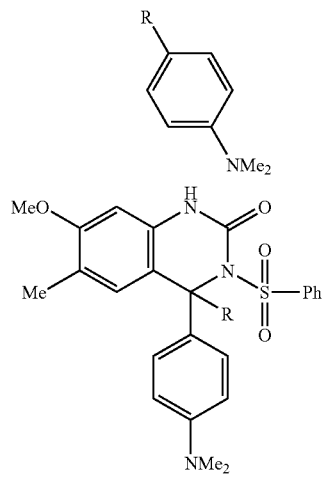
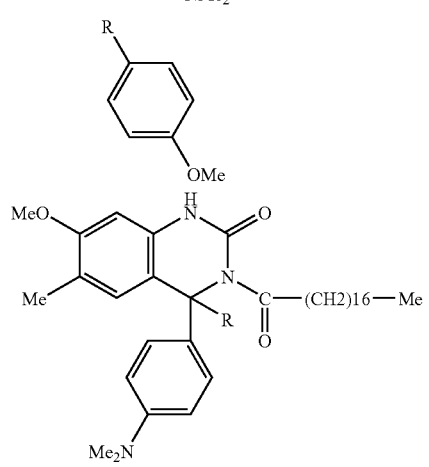
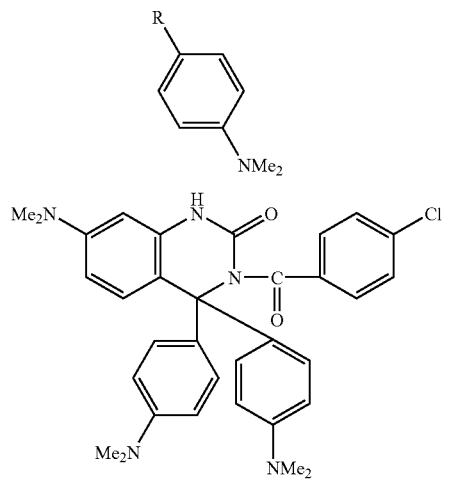

-continued
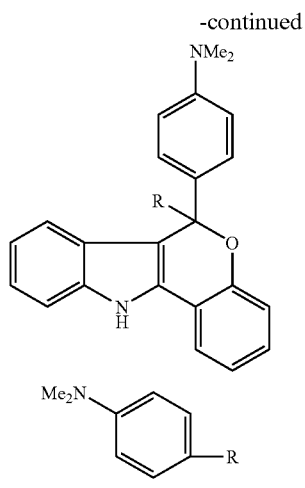
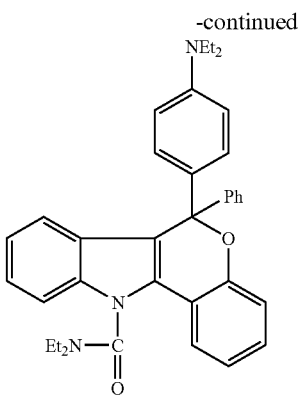
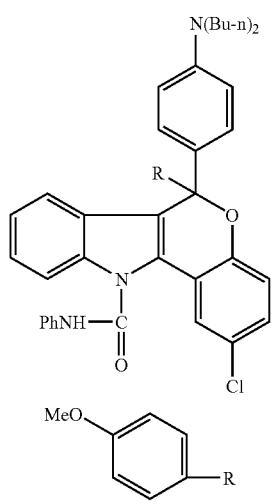
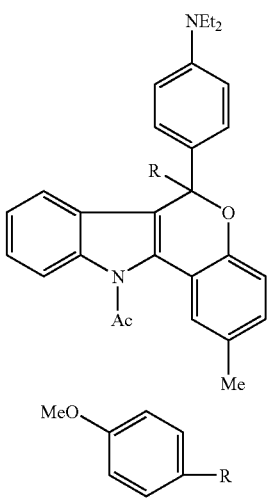
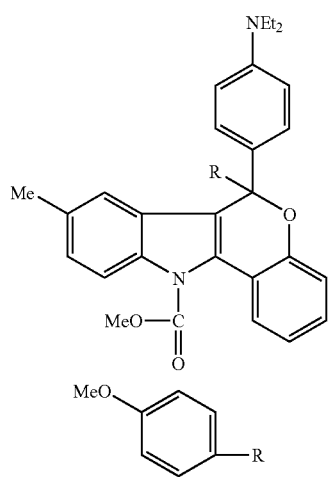
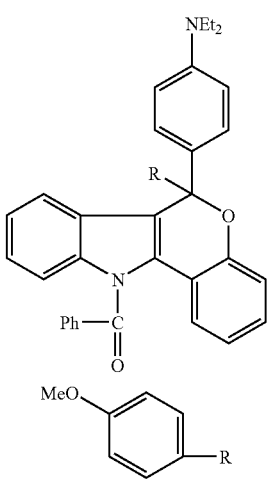

-continued
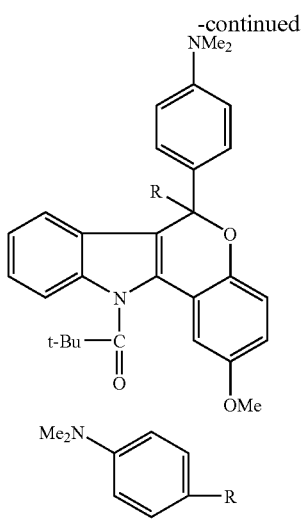
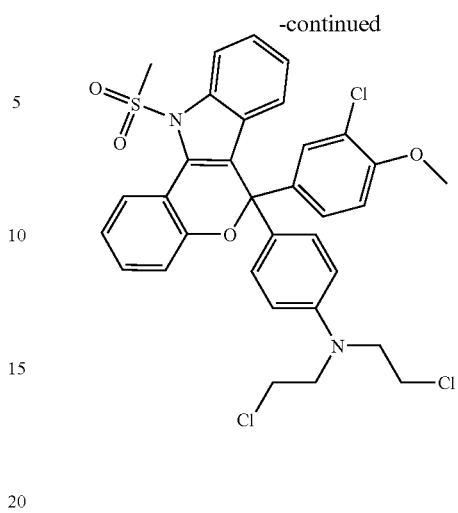
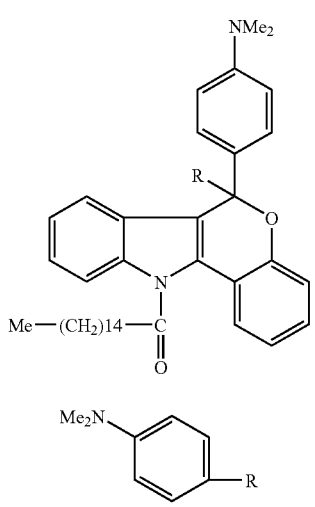
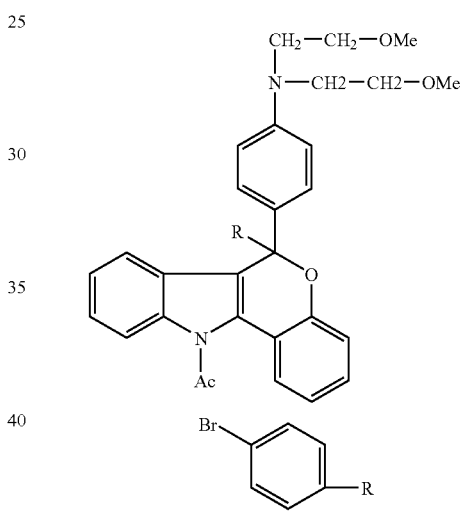
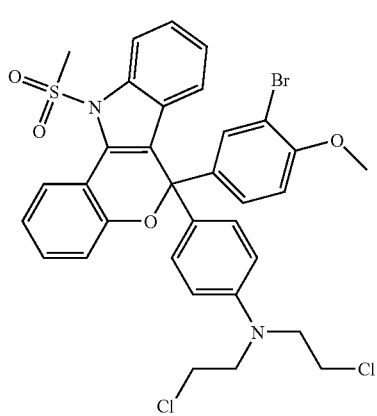
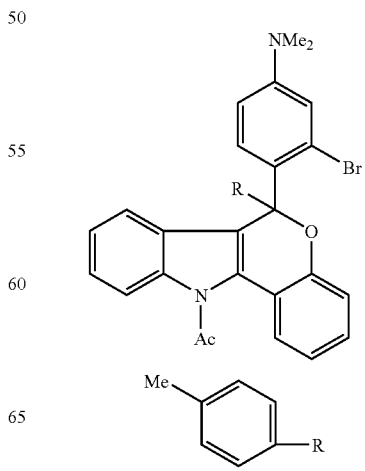

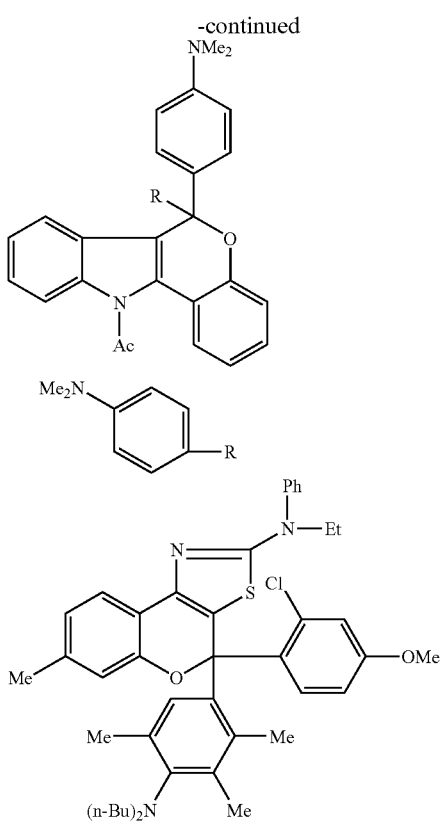

The at least one compound chosen from the compounds of formula (I), the dyes corresponding to the compounds of formula (I) wherein the ring H is open, and the addition salts thereof is present in an amount ranging from 0.001 to 10% by weight, relative to the total weight of the dyeing composition, for example ranging from 0.005 to 5% by weight.

The addition salts of the at least one compound chosen from the compounds of formula (I) and the dyes corresponding to the compounds of formula (I) wherein the ring H is open are chosen for example from the addition salts with an acid, such as hydrochlorides, hydrobromides, sulfates, methosulfates, gluconates, citrates, succinates, tartrates, lactates, tosylates, benzenesulfonates, phosphates and acetates, and the addition salts with a base, such as sodium hydroxide, potassium hydroxide, ammonia, and amines or alkanolamines.

The composition as disclosed herein can additionally comprise at least one direct dye which can, for example be chosen from nitrobenzene dyes, azo direct dyes, methine direct dyes and natural dyes. These direct dyes can be non-ionic, anionic or cationic in nature.

When at least one additional direct dye is present in the composition as disclosed herein, it is generally present in an amount ranging from 0.001 to 20% by weight, relative to the total weight of the dyeing composition, for example from 0.01 to 10% by weight.

The composition of the present disclosure can additionally comprise at least one oxidation dye chosen from oxidation bases and couplers conventionally used in oxidation dyeing.

When at least one oxidation dye is present in the composition as disclosed herein, it is generally present in an amount ranging from 0.001 to 20% by weight, relative to the total weight of the dyeing composition, for instance from 0.01 to 10% by weight.

The medium appropriate for dyeing, also known as dyeing vehicle, generally comprises water, or at least one organic solvent, or a mixture of water and of at least one organic solvent. Non-limiting mention may be made, as organic solvent, for example, of ketones, such as acetone; $C_1$-$C_4$ alkanols, such as ethanol and isopropanol; polyols, such as propylene glycol, glycerol or hexylene glycol; and polyol ethers, such as 2-butoxyethanol, propylene glycol monomethyl ether, diethylene glycol monoethyl ether and diethylene glycol monomethyl ether; and mixtures thereof.

The at least one solvent is generally present in an amount ranging from 1 to 40% by weight relative to the total weight of the dyeing composition, for example from 5 to 30% by weight.

The at least one compound chosen from the compounds of formula (I), the dyes corresponding to the compounds of formula (I) wherein the ring H is open, and the addition salts thereof are either soluble or in dispersion in the dyeing vehicle.

The composition in accordance with the present disclosure, can also include at least one adjuvant conventionally used in hair dyeing compositions, such as anionic, cationic, non-ionic, amphoteric or zwitterionic surfactants or their mixtures, anionic, cationic, non-ionic, amphoteric or zwitterionic polymers or their mixtures, inorganic or organic thickening agents, for example, anionic, cationic or non-ionic and amphoteric polymeric associative thickeners, antioxidants, penetration agents, sequestering agents, fragrances, dispersing agents, conditioning agents, such as, for example, cationic or amphoteric polymers, cations, volatile or non-volatile and modified or unmodified silicones, chitosans or chitosan derivatives, film-forming agents, ceramides, preservatives or opacifying agents.

When present in the composition, the at least one adjuvant is generally present in an amount for each adjuvant, ranging from 0.01 to 20% by weight, relative to the total weight of the composition.

Of course, a person skilled in the art will take care to choose the at least one optional additional compound so that the beneficial properties intrinsically associated with the dyeing composition in accordance with the disclosure are not, or not substantially, detrimentally affected by the envisaged addition or additions.

When the composition comprises water or a mixture of water and at least one organic solvent, the pH of the dyeing composition, in accordance with the disclosure, ranges from 3 to 12, for example from 4 to 11, and further for example from 6 to 8.5. It can be adjusted to the desired value by means of acidifying or basifying agents commonly used in the dyeing of keratinous fibers or else using conventional buffering systems.

Mention may be made, among acidifying agents, by way of non-limiting example, of inorganic acids, such as hydrochloric acid, nitric acid or sulfuric acid, or organic acids, such as compounds comprising at least one carboxylic acid functional group, such as acetic acid, tartaric acid, citric acid or and lactic acid, one sulfonic acid functional group, one phosphonic acid functional group or one phosphoric acid functional group.

Basifying agents include but are not limited to:

basic amino acids;

alkali metal or alkaline earth metal carbonates or bicarbonates;

silicates or metasilicates; and compounds of formula (II):

$$X(OH)_n \quad \text{(II)}$$

wherein:

X is chosen from potassium, lithium, sodium, and ammonium $N^+R_{17}R_{18}R_{19}R_{20}$ ions wherein $R_{17}$, $R_{18}$, $R_{19}$ and $R_{20}$, which are identical or different, are $C_2$-$C_4$ alkyl radicals, when n is equal to 1;

X is chosen from magnesium and calcium atoms, when n is equal to 2;

compounds of formula (III):

(III)

wherein:

$R_{21}$ is chosen from hydrogen atoms, $C_1$-$C_6$ alkyl radicals, $C_1$-$C_6$ monohydroxyalkyl radicals and $C_2$-$C_6$ polyhydroxyalkyl radicals;

$R_{22}$ and $R_{23}$, which are identical or different, are chosen from hydrogen atoms, $C_1$-$C_6$ alkyl radicals, $C_1$-$C_6$ monohydroxyalkyl radicals and $C_2$-$C_6$ polyhydroxyalkyl radicals; and compounds of formula (IV):

(IV)

wherein:

W is a propylene residue optionally substituted by a hydroxyl group or a $C_1$-$C_4$ alkyl radical;

$R_{24}$, $R_{25}$, $R_{26}$ and $R_{27}$, which are identical or different, are chosen from hydrogen atoms, $C_1$-$C_4$ alkyl radicals and $C_1$-$C_4$ hydroxyalkyl radicals.

As used herein, "basic amino acid" is understood to mean either (i) an amino acid exhibiting an additional cationic (or basic) group in addition to the amine functional group positioned in the a position with respect to the carboxyl group; or (ii) an amino acid exhibiting a cationic (or basic) (hydrophilic) side chain; or (iii) an amino acid carrying a side chain composed of a nitrogenous base. These definitions are generally known and published in general biochemical works, such as J. H. Weil (1983), pages 5 et seq., Lubert Stryer (1995), page 22, A. Lehninger (1993), pages 115-116, and De Boeck-Wesmael (1994), pages 57-59.

According to at least one embodiment, the basic amino acids, in accordance with the present disclosure, are chosen from those of formula (D):

(D)

wherein $R_{28}$ is a group chosen from:

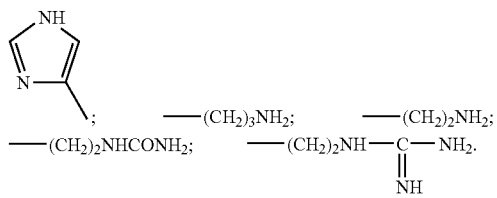

Non-limiting mention may be made, among the compounds of formula (D), by way of example, of histidine, lysine, ornithine, citrulline or arginine.

The composition according to the present disclosure, can be provided in various forms, such as in the form of liquids, creams or gels or in any other form appropriate for dyeing keratinous fibers such as human hair.

The method for treating keratinous fibers in accordance with the present disclosure, can make it possible to obtain an intense and persistent coloring, the highlights of which can vary according to the pH and the temperature, and which can be erased and reformed at least once without substantial loss of color. In at least one embodiment, the coloring is modified, erased or reformed by adjusting the pH using at least one acidifying agent or at least one basifying agent.

Within the meaning of the present disclosure, the coloring is "erased" when the keratinous fibers have returned to their original color. The coloring is "modified" when the coloring obtained is different from that obtained during the preceding stage. The coloring is "reformed" when the coloring obtained for the keratinous fibers is substantially the same as that which had been obtained during a preceding stage and which had subsequently been modified.

The coloring obtained depends on the at least one compound of formula (I) applied to the keratinous fibers. When all of the compounds of formula (I) have their ring H opened, the coloring may be intense. By varying the pH or the temperature, it is possible to erase this coloring by changing from a situation where all the compounds of formula (I) have the ring H open to a situation where all the compounds of formula (I) have the ring H closed and then to reform it by changing from a situation where all the compounds of formula (I) have the ring H closed to a situation where all the compounds of formula (I) have the ring H open. It is also possible to vary the ratio of the concentration of compounds of formula (I) in which the ring H is open to the concentration of compounds of formula (I) wherein the ring H is closed. The coloring is then modified in intensity or color according to whether the at least one compound of formula (I) has the ring H closed or the at least one compound of formula (I) was the ring H open has been applied to the keratinous fibers and according to the relative sensitivity to pH or to temperature thereof.

According to at least one embodiment, the method for treating keratinous fibers, for example, human keratinous fibers, such as the hair, comprises:

applying a dyeing composition according to the present disclosure to the keratinous fibers for a sufficient development time, the pH being adjusted using at least one first acidifying agent or at least one first basifying agent according to the coloring desired; and optionally modifying the coloring of the keratinous fibers using at least one second acidifying agent or at least one second basifying agent applied to the keratinous fibers.

The application of the dyeing composition according to the disclosure may or may not be followed by a rinsing operation.

According to at least one embodiment of the present disclosure, the at least one first acidifying agent or the at least one first basifying agent is mixed with the dyeing composition before applying to the keratinous fibers.

According to still another embodiment of the present disclosure, the at least one first acidifying agent or the at least one first basifying agent can be applied before or after the dyeing composition. It is possible to have a gap of 5 to 30 minutes between applying the at least one first acidifying agent or the at least one first basifying agent, and applying the dyeing composition. In yet another embodiment, the at least one first acidifying agent or the at least one first basifying agent is applied after the dyeing composition.

The development time of the composition in accordance with the present disclosure generally ranges from 3 to 60 minutes, for example from 5 and 40 minutes, such as from 10 and 20 minutes.

The application temperature generally ranges from ambient temperature to 250° C., such as from 25 to 55° C.

The keratinous fibers may or may not be rinsed after application of the at least one first or second acidifying agent or the at least one first or second basifying agent.

In one embodiment, the at least one acidifying or basifying agent is chosen from those which are described above.

Also disclosed herein is a multicompartment device or kit which makes it possible to carry out the method for coloring keratinous fibers described above.

The multicompartment device of the disclosure comprises, in at least one first compartment, at least one composition in accordance with the disclosure and, in at least one second compartment, at least one acidifying agent or at least one basifying agent. In another embodiment, the multicompartment device of the disclosure comprises, in the at least one second compartment, at least one acidifying agent and, in at least one third compartment, at least one basifying agent.

Also disclosed herein is a composition for dyeing keratinous fibers, for example human keratinous fibers, such as the hair, as defined above additionally comprising at least one surfactant and/or at least one polymer, for example an associative or non-associative thickening polymer.

The at least one surfactant can be chosen from anionic, cationic, non-ionic, amphoteric and zwitterionic surfactants.

As used herein, "associative polymer" is understood to mean any polymer comprising at least one $C_8$-$C_{30}$ fatty chain.

As used herein, "thickening polymer" is understood to mean any polymer which, when introduced into the polymer-free composition at 25° C., makes it possible to increase the viscosity thereof, for example any polymer which, when introduced into the polymer-free composition at 1% of active material, makes it possible to increase the viscosity thereof by at least 100 cPs at a temperature of 25° C. and at a shear rate of 1 s$^{-1}$. This viscosity can be measured, for example, using a viscosimeter of cone/plate type.

Non-limiting mention may be made of associative thickening polymers, of associative polyurethane derivatives, associative cellulose derivatives, associative polyvinyllactam derivatives and associative poly(unsaturated acid) derivatives.

Non-limiting mention may also be made of non-associative thickening polymers, of crosslinked acrylic acid homopolymers; crosslinked homopolymers of 2-acrylamido-2-methylpropanesulfonic acid and their crosslinked copolymers with acrylamide, partially or completely neutralized; homopolymers of ammonium acrylate or copolymers of ammonium acrylate and of acrylamide; homopolymers of dimethylaminoethyl methacrylate quaternized with methyl chloride or copolymers of dimethylaminoethyl methacrylate quaternized with methyl chloride and of acrylamide; non-ionic guar gums; biopolysaccharide gums of microbial origin, such as scleroglucan gum or xanthan gum; gums resulting from plant exudates, such as gum arabic, gum ghatti, gum karaya and gum tragacanth; hydroxypropyl or carboxymethyl celluloses; pectins; and alginates.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following example serves to illustrate the an embodiment of the present disclosure without, however, exhibiting a limiting nature.

EXAMPLE

Dye:

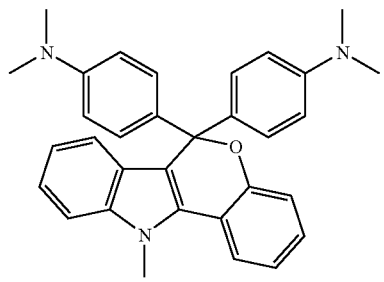

MW 473.61

Composition According to the Disclosure:

|  | Composition |
|---|---|
| Dye | 2 g |
| Benzyl alcohol | 4 g |
| Polyethylene glycol 6 EO | 6 g |
| Methanesulfonic acid | q.s. for pH3 |
| Demineralized water | q.s. for 100 g |

This composition was applied to locks of grey hair comprising 90% of natural and permed white hairs, in a proportion of 5 g per 1 g of hair, at ambient temperature for 30 minutes. At the end of the development time, the lock was dried.

The hair coloring was evaluated visually. The shade obtained was a blue shade.

The locks thus colored could have their coloring removed very rapidly by application of a 0.1M sodium hydroxide solution. The locks reencountered their original glints.

What is claimed is:

1. A composition for the coloring of human keratinous fibers comprising, in a medium appropriate for dyeing comprising water and/or at least one organic solvent, at least one thickening agent, and at least one compound chosen from the compounds of formula (I), the dyes corresponding to the compounds of formula (I) wherein the ring H is open, and the addition salts thereof:

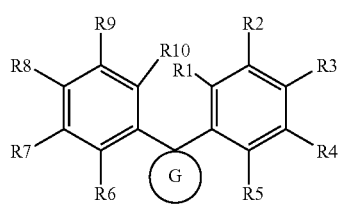

(I)

wherein:
$R_1$, $R_2$, $R_3$, $R_4$, $R_5$, $R_6$, $R_7$, $R_8$, $R_9$ and $R_{10}$ are each independently chosen from:
  hydrogen atoms;
  halogen atoms;
  hydroxyl radicals;
  nitro radicals;
  amino radicals;
  carboxyl radicals;
  aminocarbonyl radicals;
  cyano radicals; and
  radicals resulting from a hydrocarbon chain comprising from 1 to 100 carbon atoms, which is linear or branched, saturated or unsaturated and acyclic or monocyclic, wherein the ring is aromatic or nonaromatic, or polycyclic, wherein the rings are fused or unfused and aromatic or nonaromatic, which can be interrupted or terminated at one of its ends by at least one heteroatom chosen from oxygen and sulfur atoms or by at least one group chosen from carbonyl, SO, $SO_2$ and NH groups and which can be terminated at its other end by a hydrocarbonyl group or by a group comprising at least one heteroatom chosen from nitrogen, oxygen and sulfur atoms, it being possible for the hydrocarbon chain to be substituted by at least one group chosen from the following radicals: hydroxyl, halo, carboxyl, carboxy($C_1$-$C_9$)alkyl, cyano, amino, amino substituted by one or two $C_1$-$C_4$ alkyl groups, $C_1$-$C_6$ alkoxy, $C_6$-$C_{18}$ aryl, aryloxy, the aryl group of which is a $C_6$-$C_{18}$ group, and $C_2$-$C_9$ acyloxy radicals;

it being possible for two of the $R_1$, $R_2$, $R_3$, $R_4$, $R_5$, $R_6$, $R_7$, $R_8$, $R_9$ and $R_{10}$ radicals carried by two adjacent carbon atoms to form together with the carbon atoms to which they are attached, a monocarbocyclic group wherein the ring is aromatic or nonaromatic or a polycarbocyclic group wherein the rings are fused or unfused and aromatic or nonaromatic, comprising from 5 to 20 ring members, it being possible for at least one carbon atom to be replaced by an oxygen, nitrogen, sulfur or phosphorus atom, the mono- or polycarbocyclic group being unsubstituted or substituted by at least one substituent chosen from halogen atoms, hydroxyl radicals, amino radicals, carboxyl radicals, $C_6$-$C_{18}$ aryl radicals, cyano radicals, $C_1$-$C_9$ alkyl radicals, $C_1$-$C_9$ alkoxy radicals, ($C_1$-$C_9$)alkoxycarbonyl($C_1$-$C_9$)alkylamino radicals and α-naphthylalkylamino radicals;

G is a divalent radical chosen from the formulae $G_2$ to $G_5$:

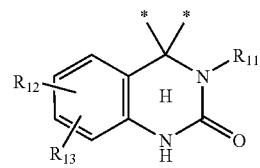

($G_1$)

ou

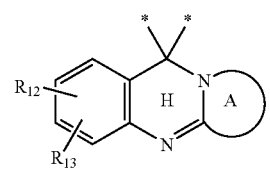

($G_2$)

ou

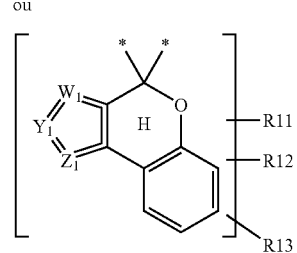

($G_3$)

ou

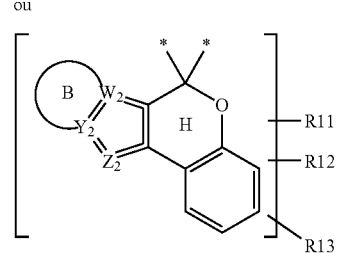

($G_4$)

-continued ou

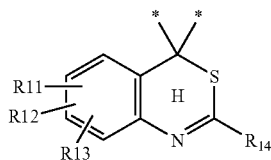
(G5)

wherein:

Y₁, W₁ and Z₁, on the one hand, and Y₂, W₂ and Z₂, on the other hand, are each independently chosen from sulfur atoms, carbon atoms, nitrogen atoms and divalent groups $CR_{15}$ and $NR_{15}$;

$R_{11}$, $R_{12}$, $R_{13}$ and $R_{15}$ have, independently of one another, the same definitions as the $R_1$ to $R_{10}$ radicals;

$R_{14}$ is chosen from:
- hydrogen atoms;
- $C_1$-$C_9$ alkyl radicals;
- amino radicals;
- $C_1$-$C_9$ alkoxy radicals;
- $(C_1$-$C_9)$alkylthio radicals;
- $C_6$-$C_{18}$ aryl radicals which are unsubstituted or substituted by at least one radical chosen from hydroxyl, $C_1$-$C_9$ alkyl, halo, carboxyl, cyano and amino radicals;
- furanyl radicals; and
- thienyl radicals;

it being possible for two of the $R_{11}$, $R_{12}$ and $R_{13}$ radicals carried by two adjacent carbon atoms to form together with the carbon atoms to which they are attached, a monocarbocyclic group wherein the ring is aromatic or nonaromatic or a polycarbocyclic group wherein the rings are fused or unfused and aromatic or nonaromatic, comprising from 5 to 20 ring members, it being possible for at least one carbon atom to be replaced by an entity chosen from oxygen, nitrogen, sulfur and phosphorus atoms, the mono- or polycarbocyclic group being unsubstituted or substituted by at least one substituent chosen from halogen atoms, hydroxyl radicals, amino radicals, carboxyl radicals, $C_6$-$C_{18}$ aryl radicals, cyano radicals, $C_1$-$C_9$ alkyl radicals and $C_1$-$C_9$ alkoxy radicals;

A is a saturated or unsaturated, substituted or unsubstituted, heterocyclic group comprising from 5 to 12 ring members;

B is chosen from $C_6$-$C_{18}$ a aryl groups and heterocyclic groups comprising from 5 to 12 ring members which are saturated or unsaturated and substituted or unsubstituted;

the amino radicals being unsubstituted or substituted by one or two identical or different radicals chosen from $C_1$-$C_9$ alkyl radicals; $C_1$-$C_9$ hydroxyalkyl radicals; $C_2$-$C_9$ alkenyl radicals; $C_5$-$C_{12}$ cycloalkyl radicals; $(C_6$-$C_{18})$arylcarbonyl radicals; cyclo($C_5$-$C_{12}$)alkyl($C_1$-$C_9$) alkyl radicals; $(C_1$-$C_9)$alkylcarbonyl radicals; $(C_1$-$C_9)$ alkoxy-carbonyl($C_1$-$C_9$)alkyl radicals; α-naphthylalkyl radicals; $C_1$-$C_9$ haloalkyl radicals; $(C_1$-$C_9)$alkylcarbonyloxy($C_1$-$C_9$)alkyl radicals; $C_1$-$C_9$ cyanoalkyl radicals; $C_2$-$C_{15}$ acyl radicals; $(C_1$-$C_9)$alkoxycarbonyl radicals; $(C_6$-$C_{18})$aryloxycarbonyl radicals; $(C_6$-$C_{18})$aryloxy($C_1$-$C_9)$alkylcarbonyl radicals; $(C_6$-$C_{18})$aryl($C_1$-$C_9$)alkoxy-carbonyl radicals; $(C_1$-$C_9)$alkoxy($C_6$-$C_{18}$)arylcarbonyl radicals; di($C_1$-$C_9$)alkylaminocarbonyl radicals; di($C_1$-$C_9$)alkyl-aminosulfonyl radicals; $(C_1$-$C_9)$alkyl($C_6$-$C_{18}$) arylsulfonyl radicals; $(C_1$-$C_9)$alkylsulfonyl radicals; di($C_1$-$C_9$)alkylamino($C_1$-$C_9$)alkyl radicals; $(C_1$-$C_9)$ alkoxy($C_1$-$C_9$)alkyl radicals; $C_6$-$C_{18}$ aryl radicals and $(C_6$-$C_{18})$aryl($C_1$-$C_9)$alkyl radicals optionally substituted on the aryl nucleus by at least one substituent chosen from halogen atoms, $C_1$-$C_9$ alkyl radicals, nitro radicals, di($C_1$-$C_9$)alkylamino radicals and $C_1$-$C_9$ alkoxy radicals; it being possible for the two radicals to form together with the nitrogen atom of the amino group, a 5- to 12-membered ring optionally carrying another heteroatom, it being possible for the ring to be substituted by a $C_1$-$C_9$ alkyl radical, and wherein the composition is appropriate for coloring human keratinous fibers.

2. The composition, according to claim 1,
wherein:
$R_5$ is a hydrogen atom;
$R_1$ is chosen from:
- hydrogen atoms;
- halogen atoms;
- $C_1$-$C_9$ alkyl radicals;
- $C_1$-$C_9$ alkoxy radicals;
- nitro radicals;
- amino radicals;
- $(C_1$-$C_9)$alkylthio radicals; and
- $(C_2$-$C_9)$acyloxy($C_1$-$C_9$)alkoxy radicals;

$R_2$ is chosen from hydrogen atoms; $C_1$-$C_9$ alkyl radicals; $C_1$-$C_9$ alkoxy radicals; halogen atoms; and amino radicals;

$R_3$ is chosen from hydrogen atoms; amino radicals; halogen atoms; $(C_6$-$C_{18})$aryloxy($C_1$-$C_9$)alkoxy radicals; nitro radicals; and $C_1$-$C_9$ alkoxy radicals;

$R_4$ is chosen from hydrogen atoms; halogen atoms; $C_1$-$C_9$ alkyl radicals; $C_1$-$C_9$ alkoxy radicals; and $(C_1$-$C_9)$alkylthio radicals;

$R_6$ is chosen from hydrogen atoms; halogen atoms; $C_1$-$C_9$ alkyl radicals; $C_1$-$C_9$ alkoxy radicals; nitro radicals; amino radicals; and $(C_2$-$C_9)$acyloxy($C_1$-$C_9$)alkoxy radicals;

$R_7$ is chosen from hydrogen atoms; halogen atoms; $C_1$-$C_9$ alkyl radicals; and $C_1$-$C_9$ alkoxy radicals;

$R_8$ is chosen from hydrogen atoms; halogen atoms; $C_1$-$C_9$ alkyl radicals; $C_1$-$C_9$ alkoxy radicals; nitro radicals; and amino radicals;

$R_9$ is chosen from hydrogen atoms; $C_1$-$C_9$ alkyl radicals; and $C_1$-$C_9$ alkoxy radicals;

$R_{10}$ is chosen from hydrogen atoms and $C_1$-$C_9$ alkoxy radicals;

$R_{11}$ is chosen from hydrogen atoms; halogen atoms; $C_1$-$C_9$ alkyl radicals; $C_1$-$C_9$ alkoxy radicals; $C_6$-$C_{18}$ aryl radicals; amino radicals; $C_2$-$C_{18}$ acyl radicals; and $(C_6$-$C_{18})$ arylsulfonyl radicals;

$R_{12}$ is chosen from hydrogen atoms; $C_1$-$C_9$ alkyl radicals; $C_1$-$C_9$ alkoxy radicals; and amino radicals;

$R_{13}$ is a hydrogen atom; and $R_{14}$ is chosen from hydrogen atoms; amino radicals; $C_6$-$C_{18}$ aryl radicals; $(C_1$-$C_9)$alkylthio radicals; and $C_1$-$C_9$ alkoxy radicals;

it being possible for $R_1$ and $R_2$ and/or $R_2$ and $R_3$ and/or $R_6$ and $R_7$ and/or $R_7$ and $R_8$ to form, together with the carbon atoms to which they are attached, a monocarbocyclic or polycarbocyclic group wherein the rings are aromatic and fused or unfused, which comprises from 5 to 20 ring members, it being possible for at least one carbon atom to be replaced by an entity chosen from oxygen, nitrogen, sulfur and phosphorus atoms, and which is unsubstituted or substituted.

3. The composition according to claim 1, wherein the at least one compound of formula (I) is chosen from the compounds of formula ($I_1$):

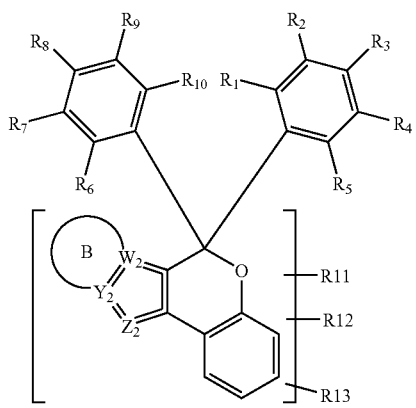

wherein:

$Y_2$, $W_2$ and $Z_2$ are each independently chosen from carbon atoms, nitrogen atoms, sulfur atoms and divalent groups $CR_{15}$ and $NR_{15}$;

B is chosen from $C_6$-$C_{18}$ aryl groups and 5- to 12-membered heterocyclic groups which are saturated or unsaturated and substituted or unsubstituted;

$R_1$ is chosen from hydrogen atoms; halogen atoms; $C_1$-$C_9$ alkoxy radicals; $C_1$-$C_9$ alkyl radicals; nitro radicals; and ($C_1$-$C_9$)alkylthio radicals;

$R_2$ is chosen from hydrogen atoms; halogen atoms; $C_1$-$C_9$ alkyl radicals; and $C_1$-$C_9$ alkoxy radicals;

$R_3$ is chosen from hydrogen atoms; halogen atoms; nitro radicals; amino radicals; and $C_1$-$C_9$ alkoxy radicals;

$R_4$ is chosen from hydrogen atoms; $C_1$-$C_9$ alkoxy radicals; $C_1$-$C_9$ alkyl radicals; and ($C_1$-$C_9$)alkylthio radicals;

$R_5$, $R_{10}$ and $R_{13}$ are hydrogen atoms;

$R_6$ is chosen from hydrogen atoms; halogen atoms; nitro radicals; $C_1$-$C_9$ alkoxy radicals; $C_1$-$C_9$ alkyl radicals; amino radicals; and ($C_2$-$C_9$)acyloxy($C_1$-$C_9$)alkoxy radicals;

$R_7$ is chosen from hydrogen atoms and $C_1$-$C_9$ alkoxy radicals;

$R_8$ is chosen from hydrogen atoms; halogen atoms; $C_1$-$C_9$ alkoxy radicals; $C_1$-$C_9$ alkyl radicals; and amino radicals;

$R_9$ is chosen from hydrogen atoms; $C_1$-$C_9$ alkoxy radicals; and $C_1$-$C_9$ alkyl radicals;

$R_{11}$ is chosen from hydrogen atoms; halogen atoms; amino radicals; $C_1$-$C_9$ alkyl radicals; di($C_1$-$C_9$)alkylaminocarbonyl radicals; ($C_6$-$C_{18}$)arylcarbonyl radicals; ($C_6$-$C_{18}$) arylsulfonyl radicals; and $C_2$-$C_9$ acyl radicals;

$R_{12}$ is chosen from hydrogen atoms; $C_1$-$C_9$ alkyl radicals; ($C_6$-$C_{18}$)arylaminocarbonyl radicals; $C_2$-$C_{20}$ acyl radicals; and ($C_1$-$C_9$)alkoxycarbonyl radicals;

it being possible for $R_1$ and $R_2$, on the one hand, and $R_6$ and $R_7$, on the other hand, to form, together with the carbon atoms to which they are attached, an aromatic $C_6$-$C_{18}$ ring.

4. The composition according to claim 1, wherein the at least one compound of formula (I) is chosen from the compounds of formulae ($I_2$) to ($I_6$):

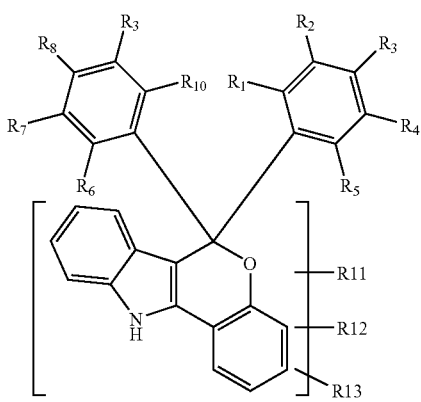

ou

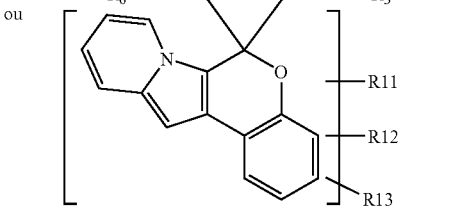

ou

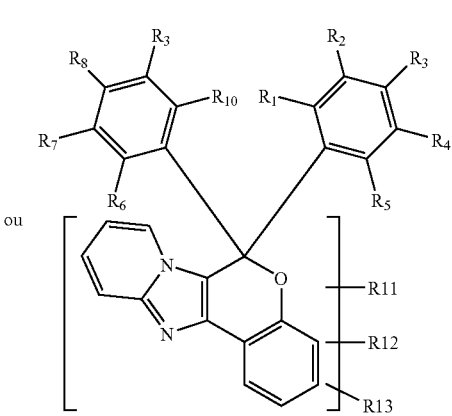

-continued

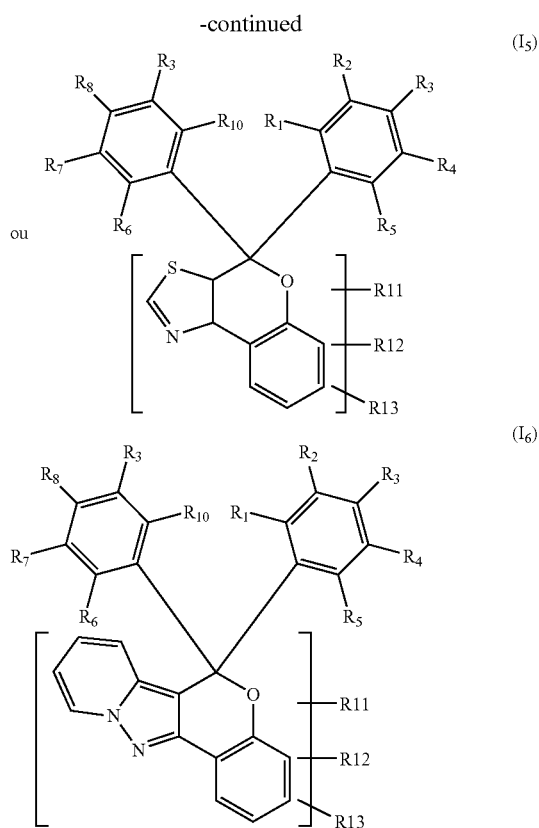

wherein:
- $R_1$ is chosen from hydrogen atoms; halogen atoms; $C_1$-$C_9$ alkoxy radicals; $C_1$-$C_9$ alkyl radicals; nitro radicals; and ($C_1$-$C_9$)alkylthio radicals;
- $R_2$ is chosen from hydrogen atoms; halogen atoms; $C_1$-$C_9$ alkyl radicals; and $C_1$-$C_9$ alkoxy radicals;
- $R_3$ is chosen from hydrogen atoms; halogen atoms; nitro radicals; amino radicals; and $C_1$-$C_9$ alkoxy radicals;
- $R_4$ is chosen from hydrogen atoms; $C_1$-$C_9$ alkoxy radicals; $C_1$-$C_9$ alkyl radicals; and ($C_1$-$C_9$)alkylthio radicals;
- $R_5$, $R_{10}$ and $R_{13}$ are hydrogen atoms;
- $R_6$ is chosen from hydrogen atoms; halogen atoms; nitro radicals; $C_1$-$C_9$ alkoxy radicals; $C_1$-$C_9$ alkyl radicals; amino radicals; and ($C_2$-$C_9$)acyloxy($C_1$-$C_9$)alkoxy radicals;
- $R_7$ is chosen from hydrogen atoms and $C_1$-$C_9$ alkoxy radicals;
- $R_8$ is chosen from hydrogen atoms; halogen atoms; $C_1$-$C_9$ alkoxy radicals; $C_1$-$C_9$ alkyl radicals; and amino radicals;
- $R_9$ is chosen from hydrogen atoms; $C_1$-$C_9$ alkoxy radicals; and $C_1$-$C_9$ alkyl radicals;
- $R_{11}$ is chosen from hydrogen atoms; halogen atoms; amino radicals; $C_1$-$C_9$ alkyl radicals; di($C_1$-$C_9$)alkylaminocarbonyl radicals; ($C_6$-$C_{18}$)arylcarbonyl radicals; ($C_6$-$C_{18}$) arylsulfonyl radicals; and $C_2$-$C_9$ acyl radicals;
- $R_{12}$ is chosen from hydrogen atoms; $C_1$-$C_9$ alkyl radicals; ($C_6$-$C_{18}$)arylaminocarbonyl radicals; $C_2$-$C_{20}$ acyl radicals; and ($C_1$-$C_9$)alkoxycarbonyl radicals;
- it being possible for $R_1$ and $R_2$, on the one hand, and $R_6$ and $R_7$, on the other hand, to form, together with the carbon atoms to which they are attached, an aromatic $C_6$-$C_{18}$ ring.

5. The composition according to claim 1, wherein the at least one compound of formula (I) is chosen from the compounds of formula ($I_7$):

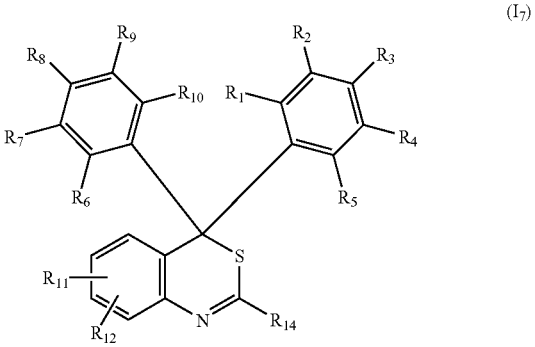

wherein:
- $R_1$ is chosen from hydrogen atoms; halogen atoms; and $C_1$-$C_9$ alkoxy radicals;
- $R_2$ is chosen from hydrogen atoms; halogen atoms; $C_1$-$C_9$ alkyl radicals; and $C_1$-$C_9$ alkoxy radicals;
- $R_3$ is chosen from hydrogen atoms and amino radicals;
- $R_4$, $R_5$, $R_9$ and $R_{10}$ are hydrogen atoms;
- $R_6$ is chosen from hydrogen atoms; halogen atoms; and $C_1$-$C_9$ alkoxy radicals;
- $R_7$ is chosen from hydrogen atoms; halogen atoms; $C_1$-$C_9$ alkyl radicals; and $C_1$-$C_9$ alkoxy radicals;
- $R_8$ is chosen from hydrogen atoms and amino radicals;
- $R_{11}$ is chosen from hydrogen atoms; $C_1$-$C_9$ alkyl radicals; $C_1$-$C_9$ alkoxy radicals; amino radicals; and $C_6$-$C_{18}$ aryl radicals;
- $R_{12}$ is chosen from hydrogen atoms; $C_1$-$C_9$ alkyl radicals; and $C_1$-$C_9$ alkoxy radicals;
- $R_{14}$ is chosen from hydrogen atoms; amino radicals; $C_6$-$C_{18}$ aryl radicals; ($C_1$-$C_9$)alkylthio radicals; and $C_1$-$C_9$ alkoxy radicals;
- it being possible for $R_1$ and $R_2$ and/or $R_2$ and $R_3$ and/or $R_7$ and $R_8$ and/or $R_{11}$ and $R_{12}$ to form, together with the carbon atoms to which they are attached, a $C_6$-$C_{18}$ aromatic ring or a heterocycle comprising from 5 to 12 ring members.

6. The composition according to claim 1, wherein the least one compound of formula (I) is chosen from the compounds of formula ($I_8$):

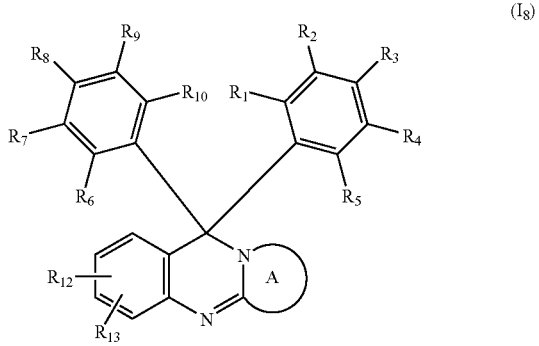

wherein:
- A is chosen from $C_6$-$C_{18}$ aryl groups and saturated or unsaturated, substituted or unsubstituted, 5- to 12-membered heterocyclic groups comprising at least two heteroatoms, including the nitrogen atom belonging to the condensed ring;

$R_1$, $R_2$, $R_4$, $R_5$, $R_6$, $R_7$, $R_9$, $R_{10}$ and $R_{13}$ are hydrogen atoms; and $R_3$, $R_8$ and $R_{12}$ are each independently chosen from hydrogen atoms and amino radicals.

7. The composition according to claim 1, wherein the formula ($G_2$) is chosen from either of the following formulae:

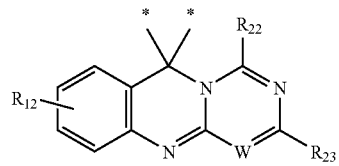

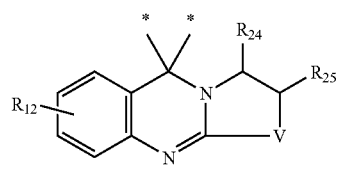

wherein:

$R_{22}$ and $R_{23}$ are each independently chosen from amino radicals; $C_1$-$C_9$ alkyl radicals; and $C_1$-$C_9$ alkoxy radicals;

W is chosen from nitrogen atoms and $CR_{26}$ groups;

V is chosen from sulfur atoms and oxygen atoms;

$R_{24}$ and $R_{25}$ are hydrogen atoms or form, with one another and with the carbon atoms to which they are attached, a benzene ring;

$R_{12}$ is chosen from hydrogen atoms; $C_1$-$C_9$ alkyl radicals; $C_1$-$C_9$ alkoxy radicals; and amino radicals;

$R_{26}$ is a hydrogen atom or can form, with $R_{23}$ and a carbon atom to which they are attached, a benzene ring.

8. The composition according to claim 1, wherein the at least one compound of formula (I) is chosen from the compounds:

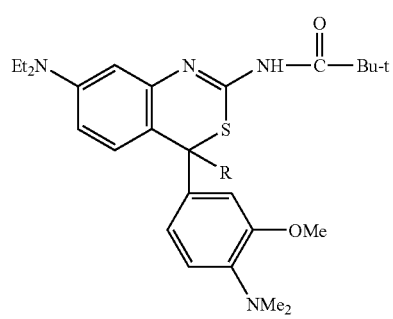

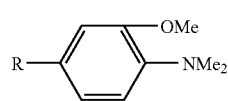

-continued

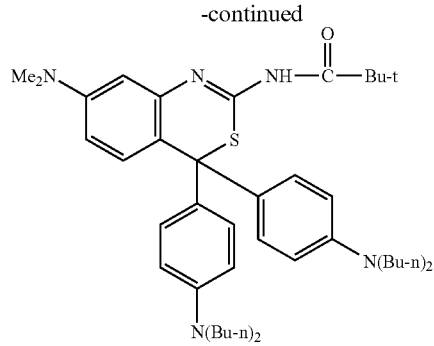

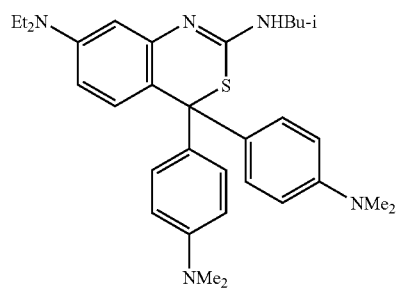

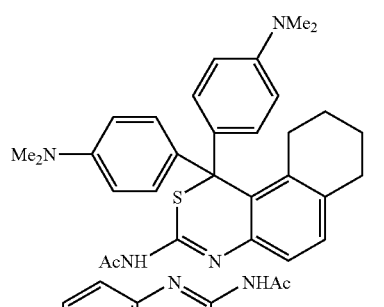

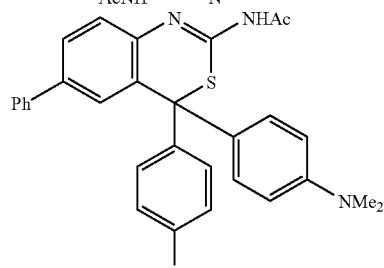

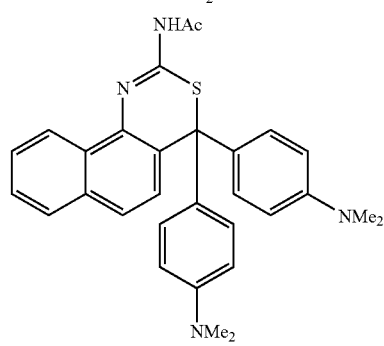

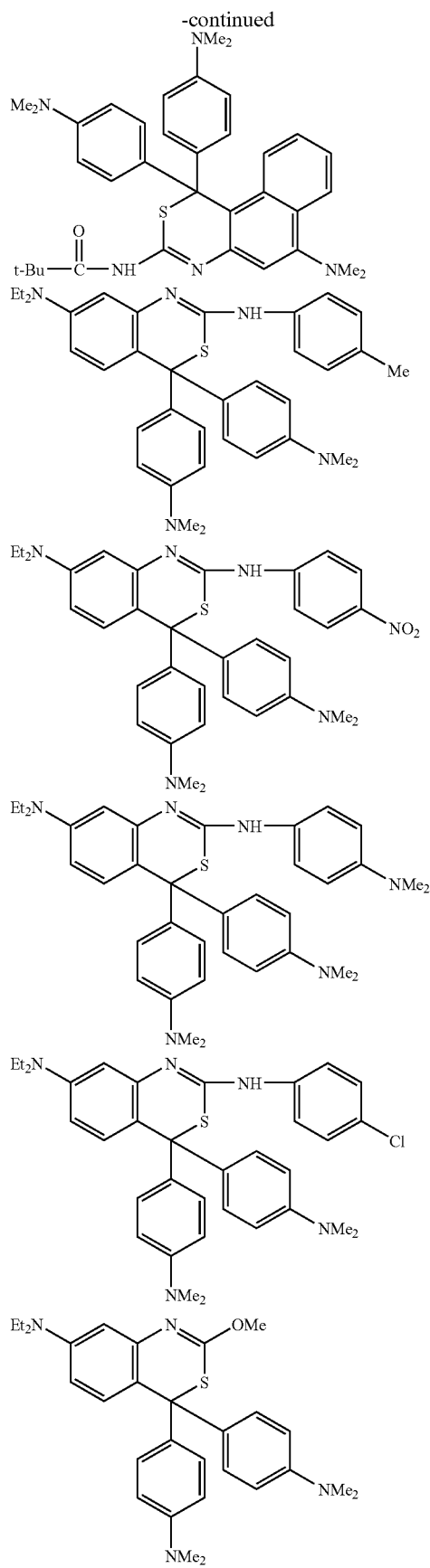
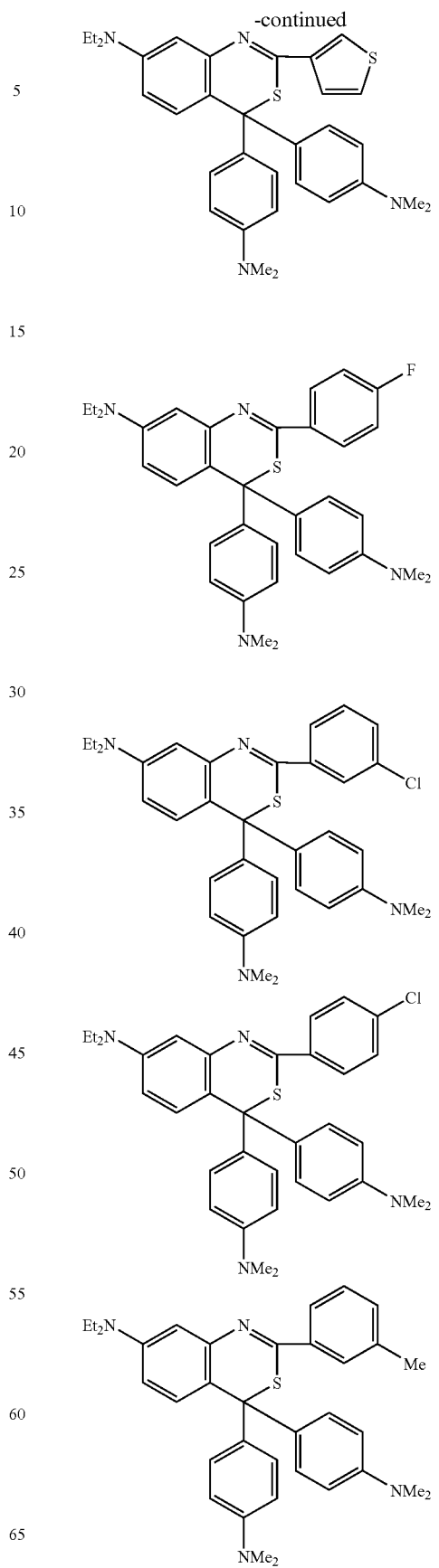

-continued
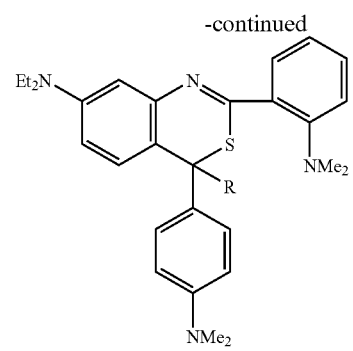
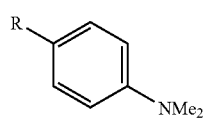
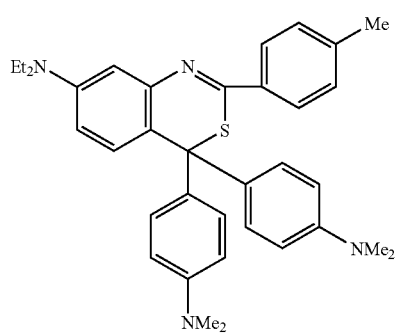
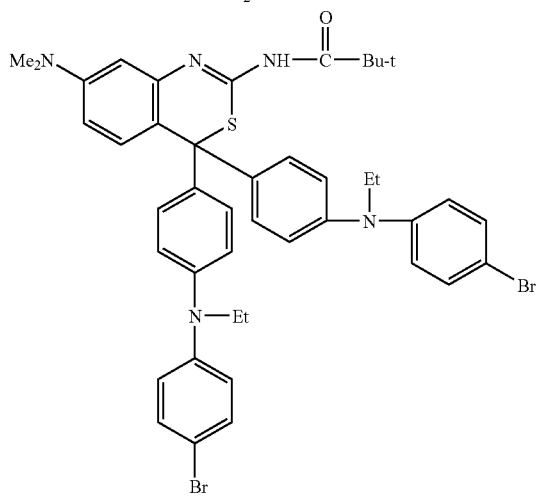
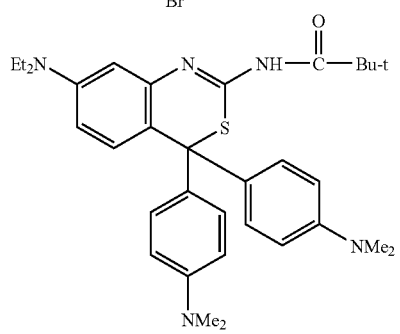
-continued
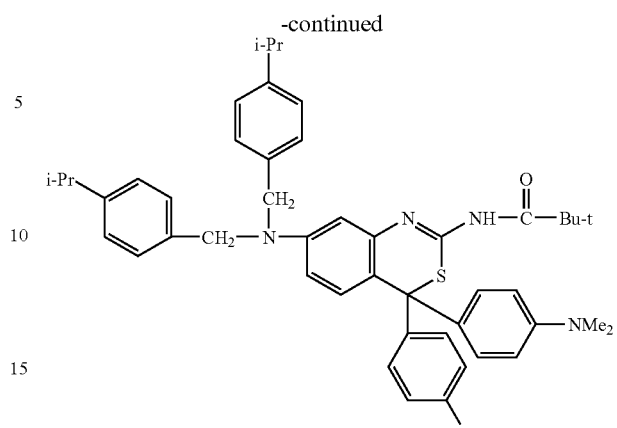
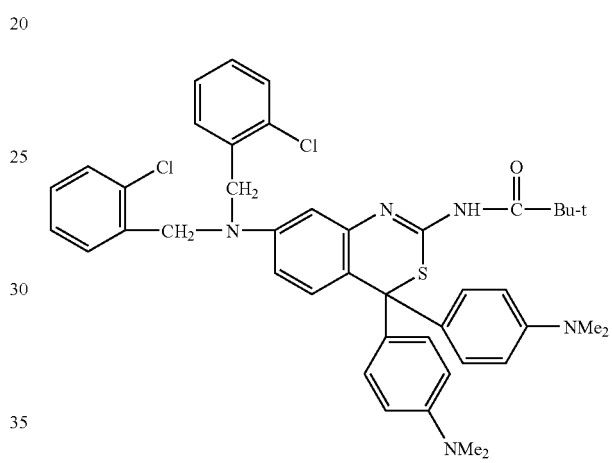
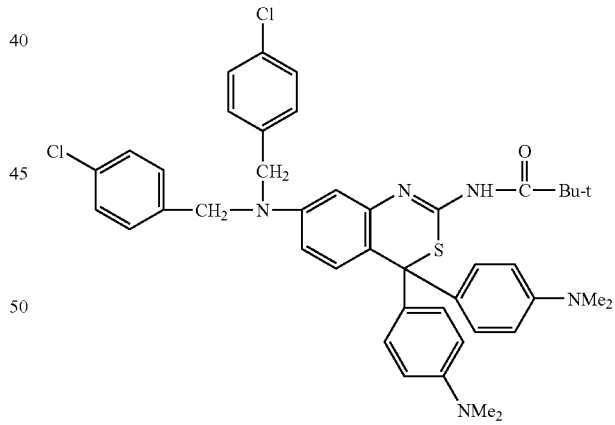
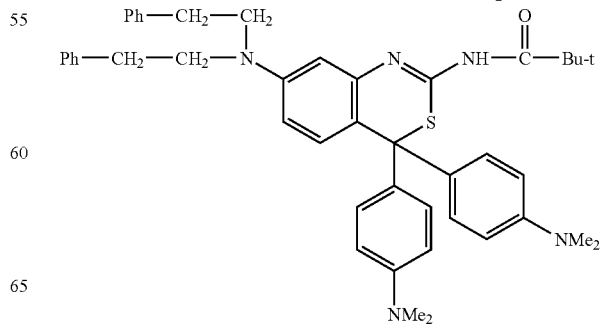

-continued
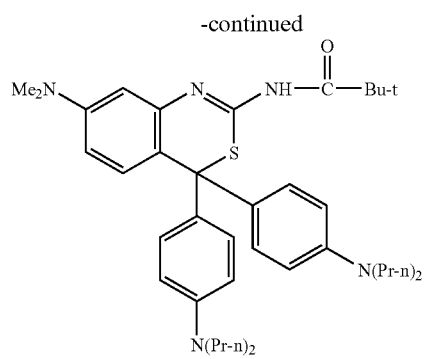
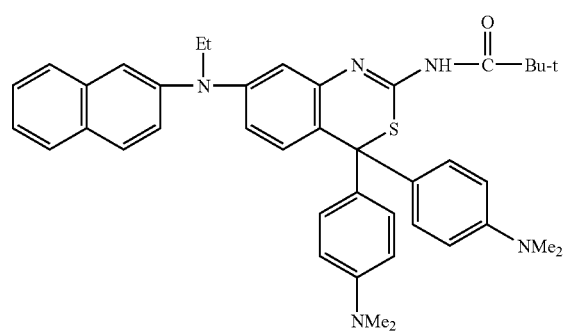
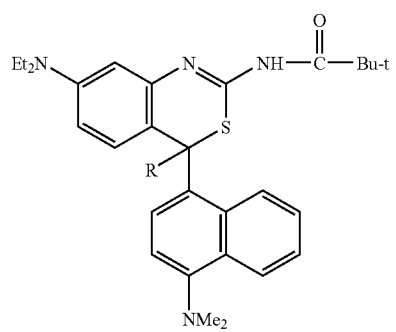
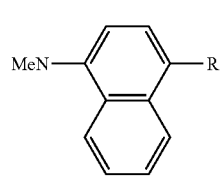
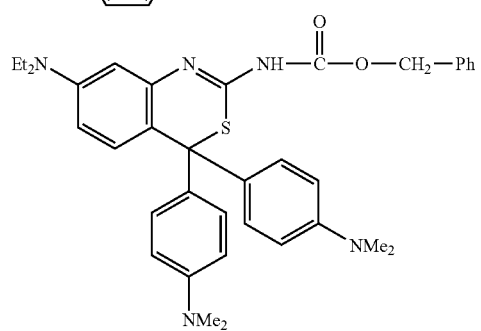
-continued
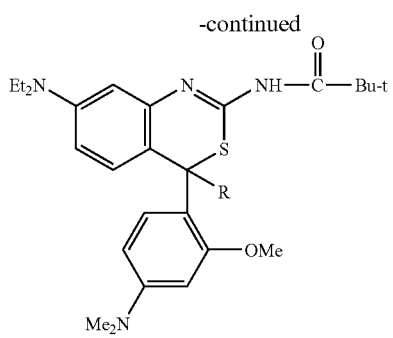
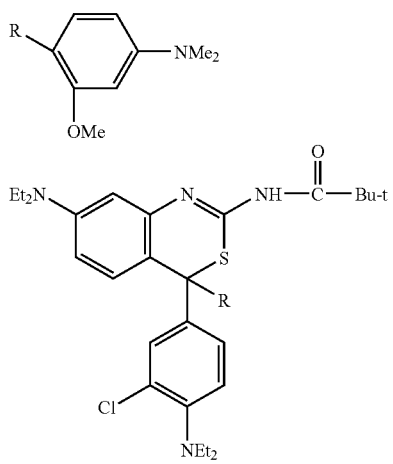
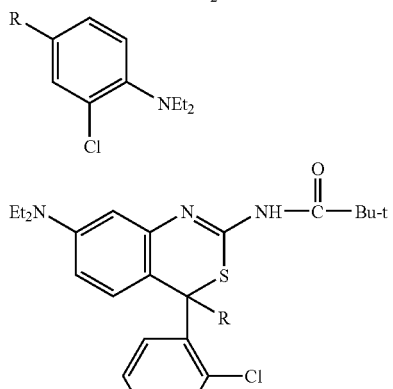
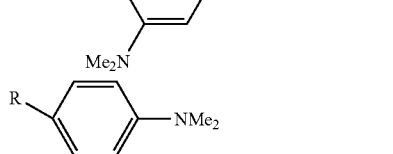
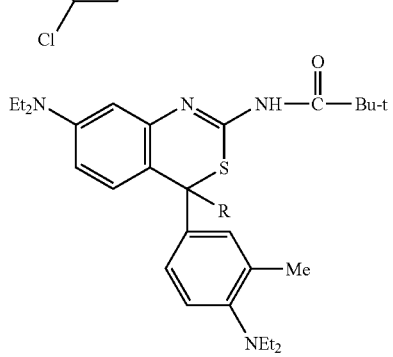

73
-continued
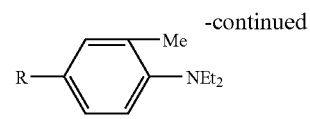
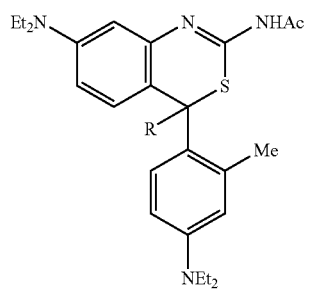
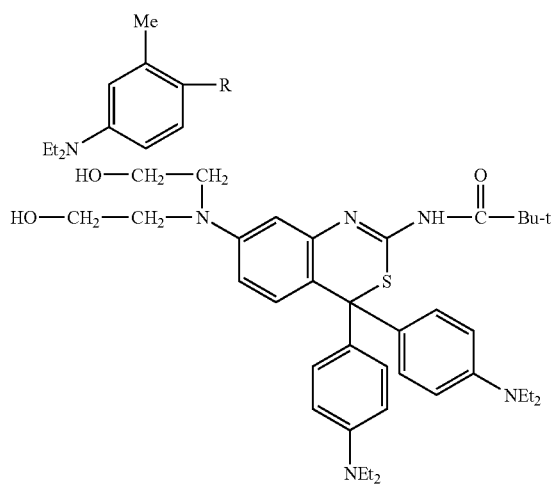
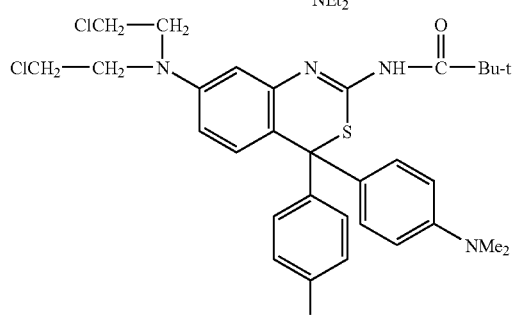
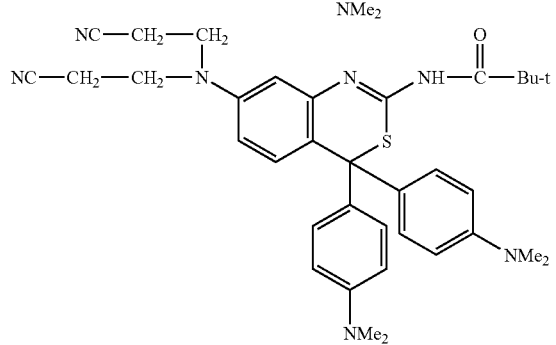
74
-continued
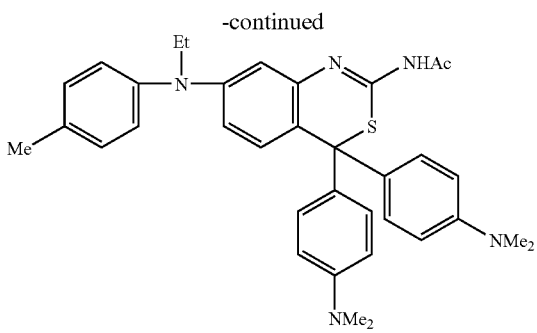
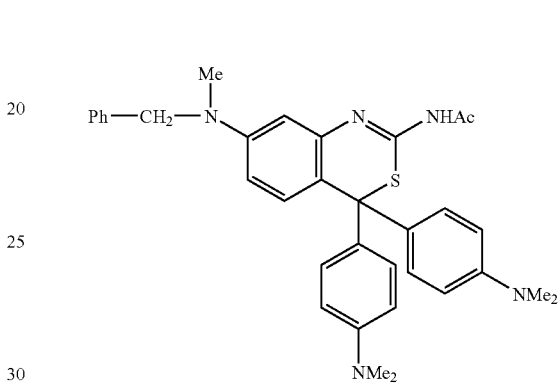
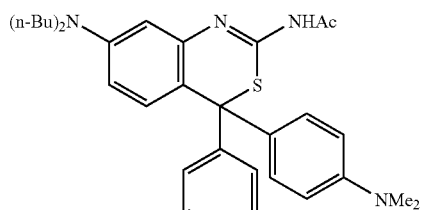
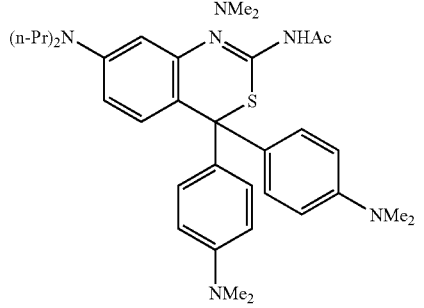
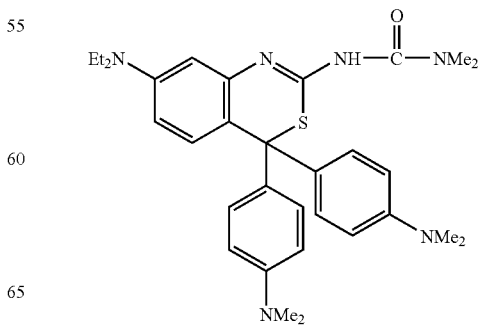

-continued
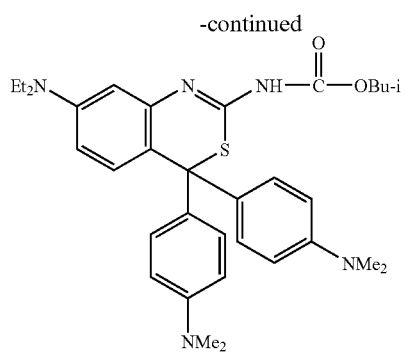
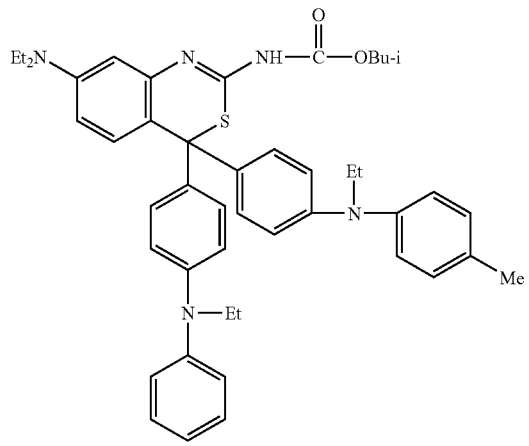
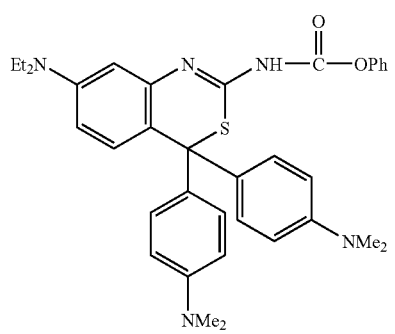
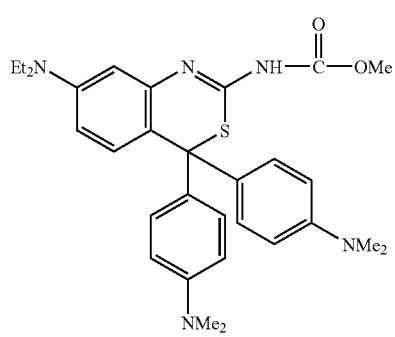
-continued
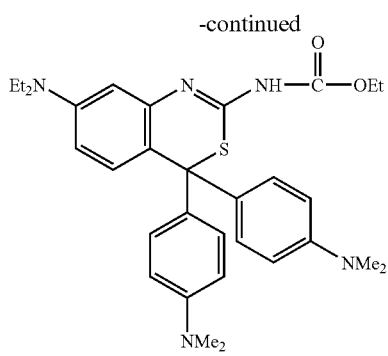
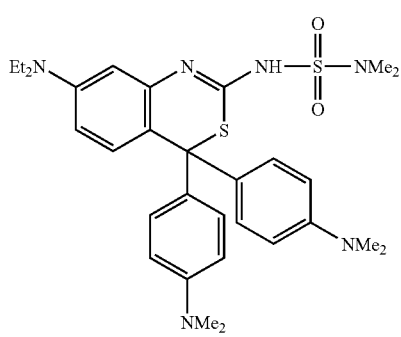
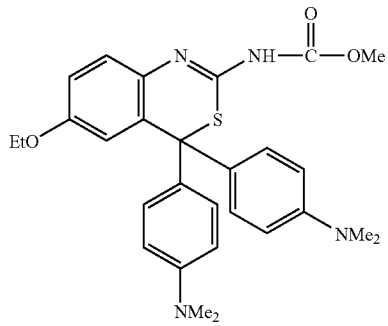
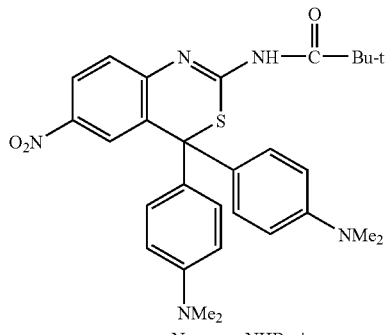
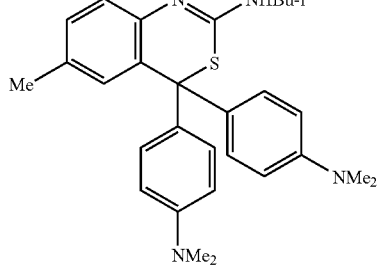

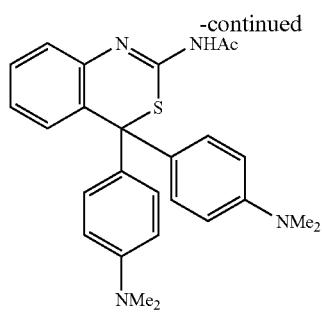
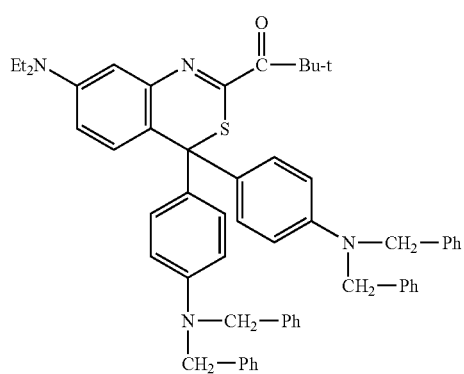
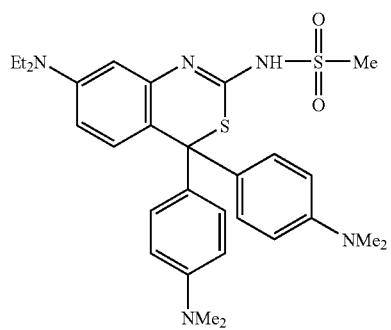
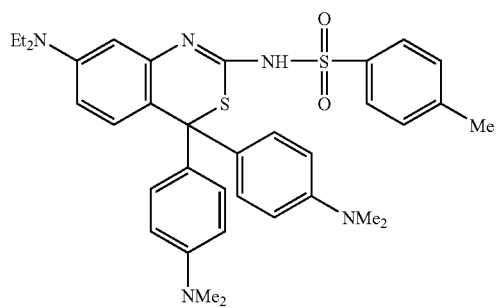
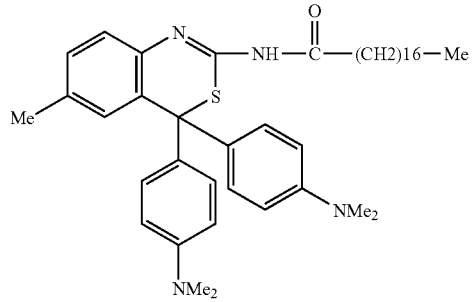
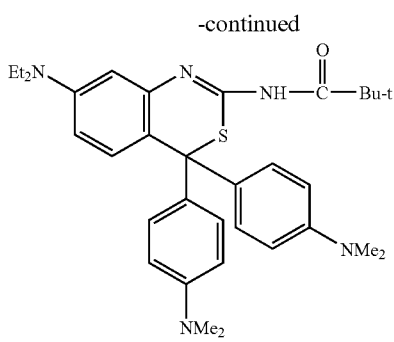
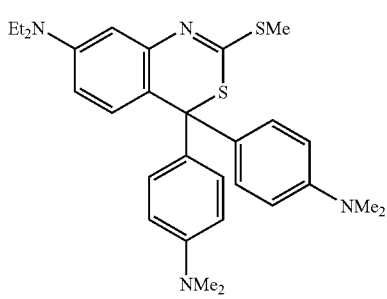
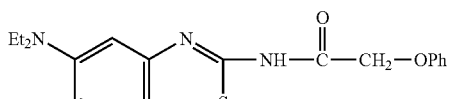
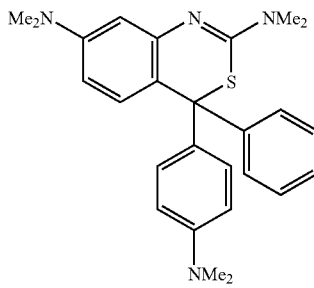
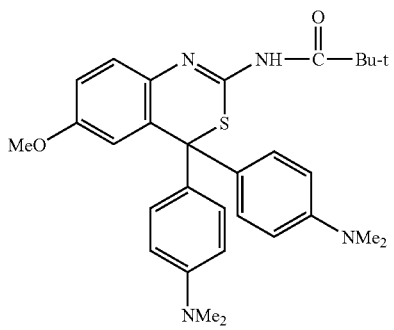

-continued
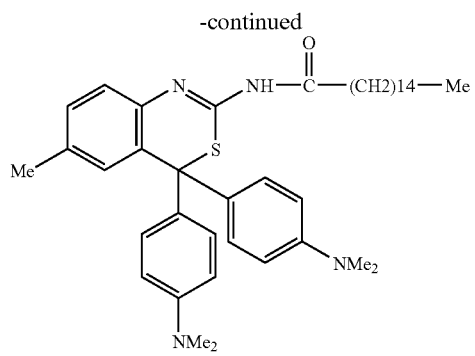
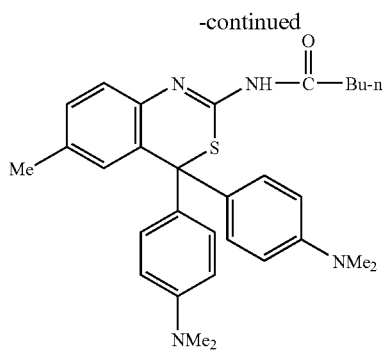
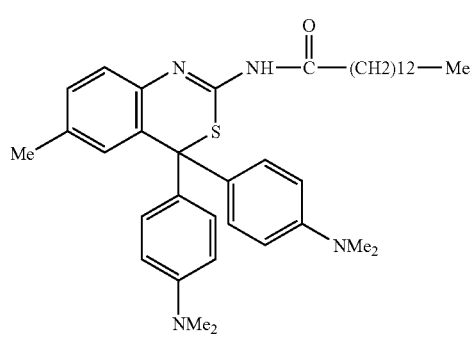
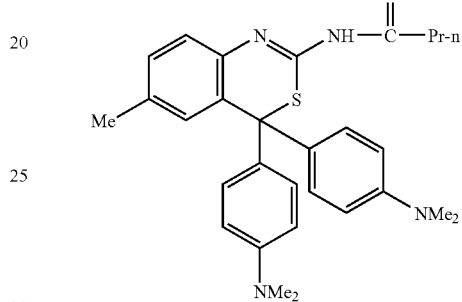
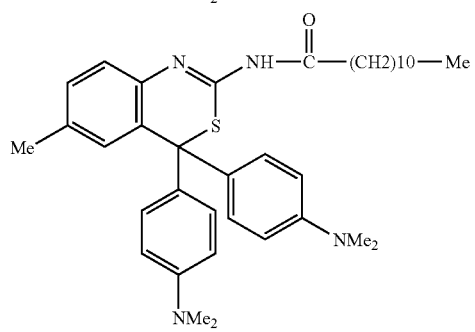
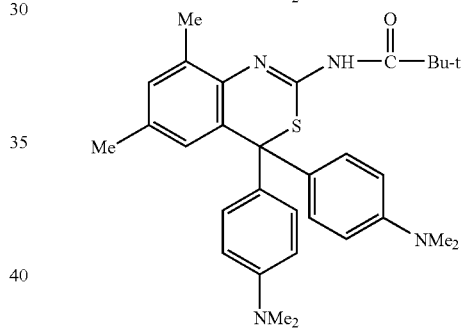
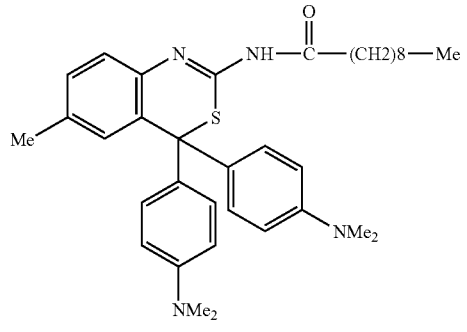
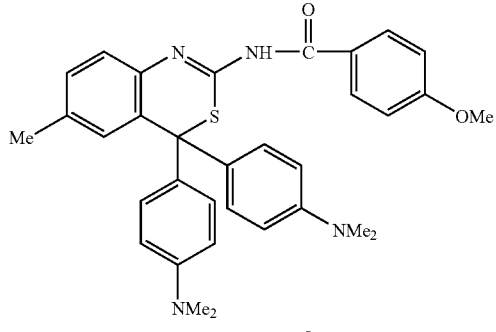
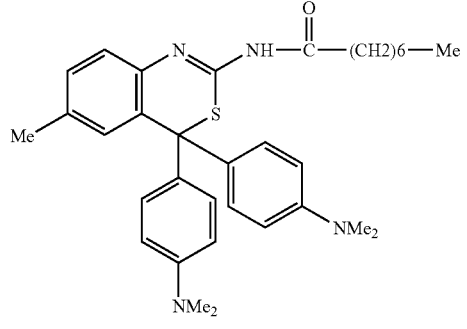
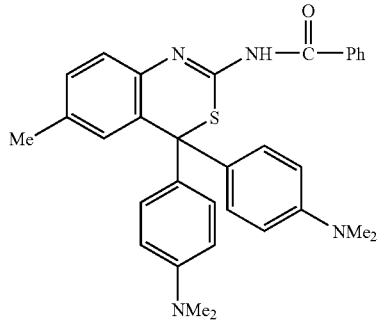

-continued
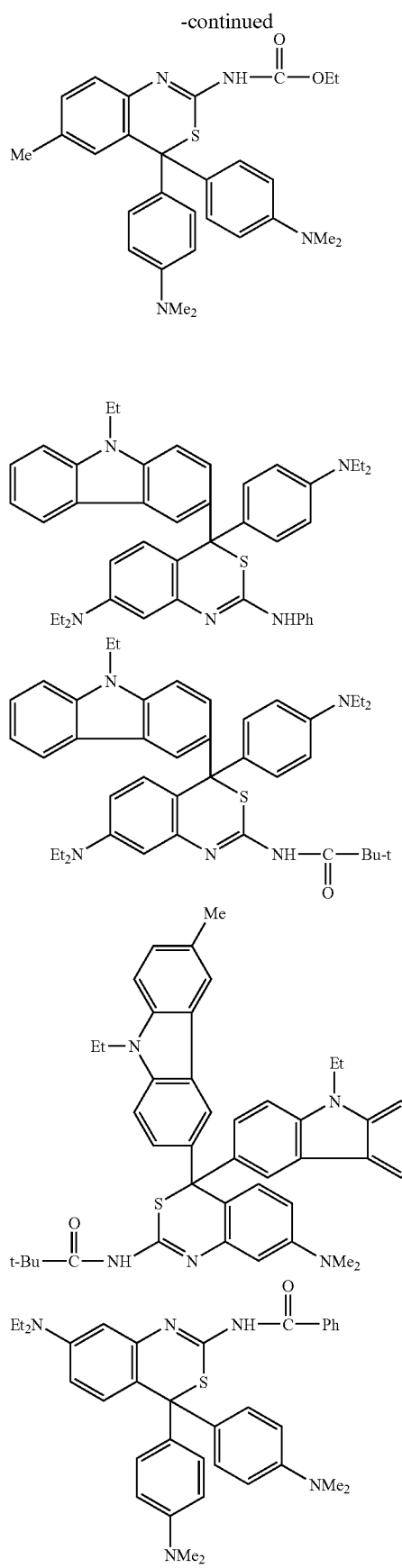
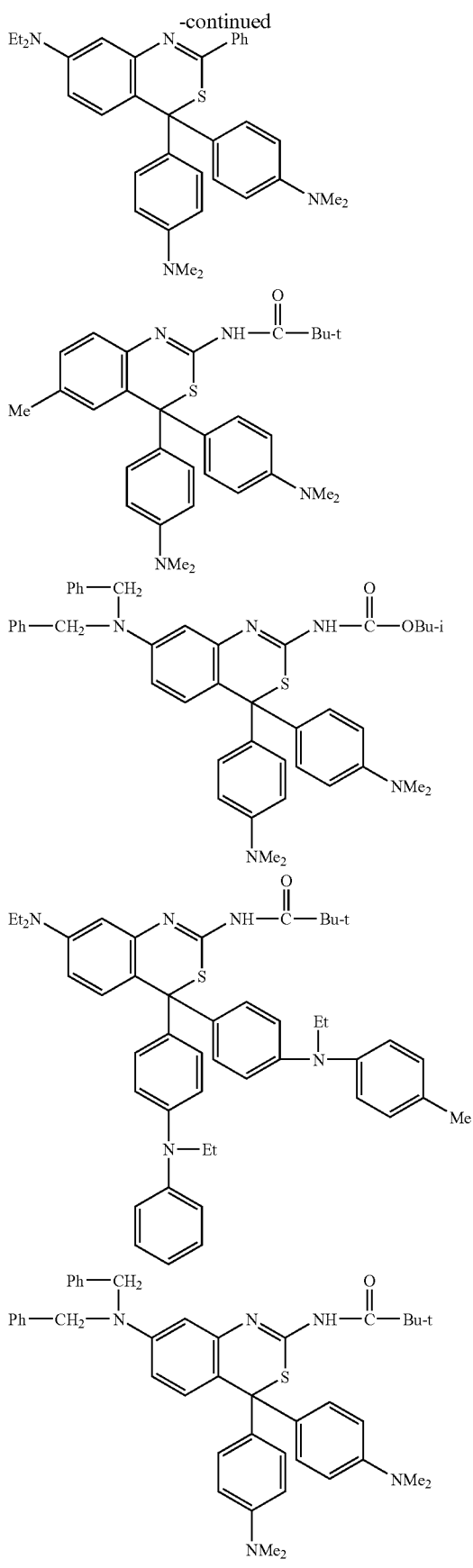

-continued
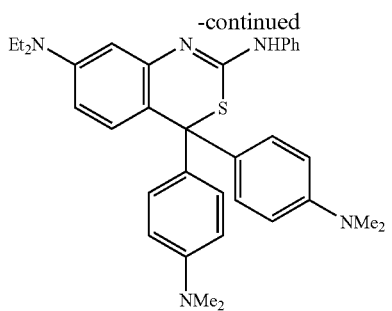
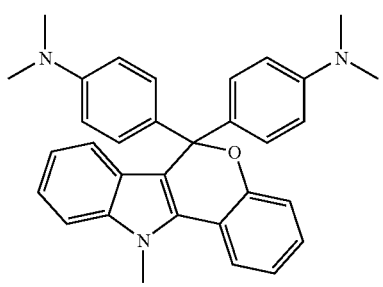
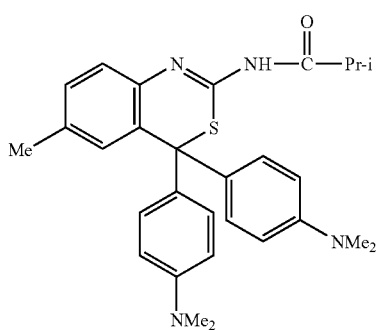
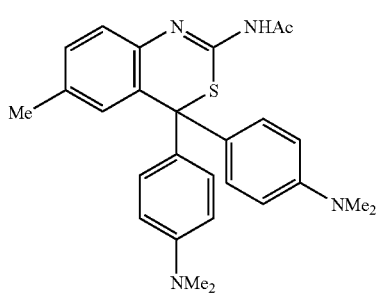
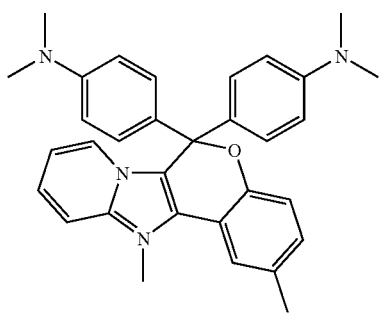
-continued
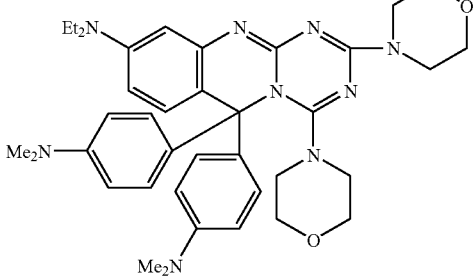
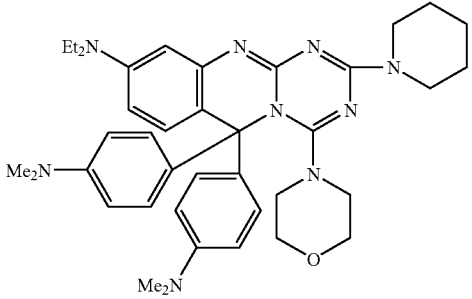
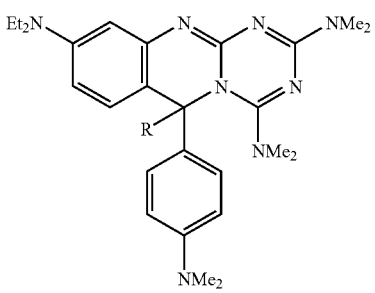
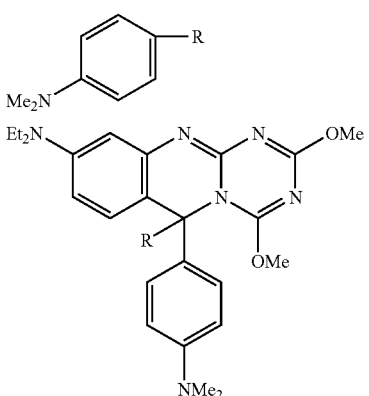
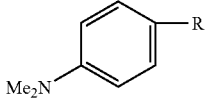

-continued
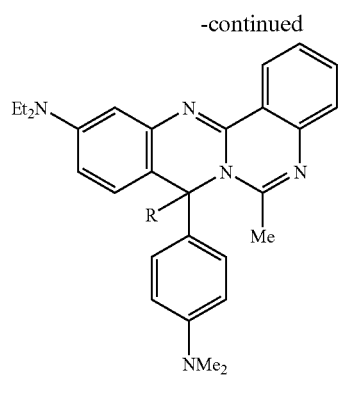
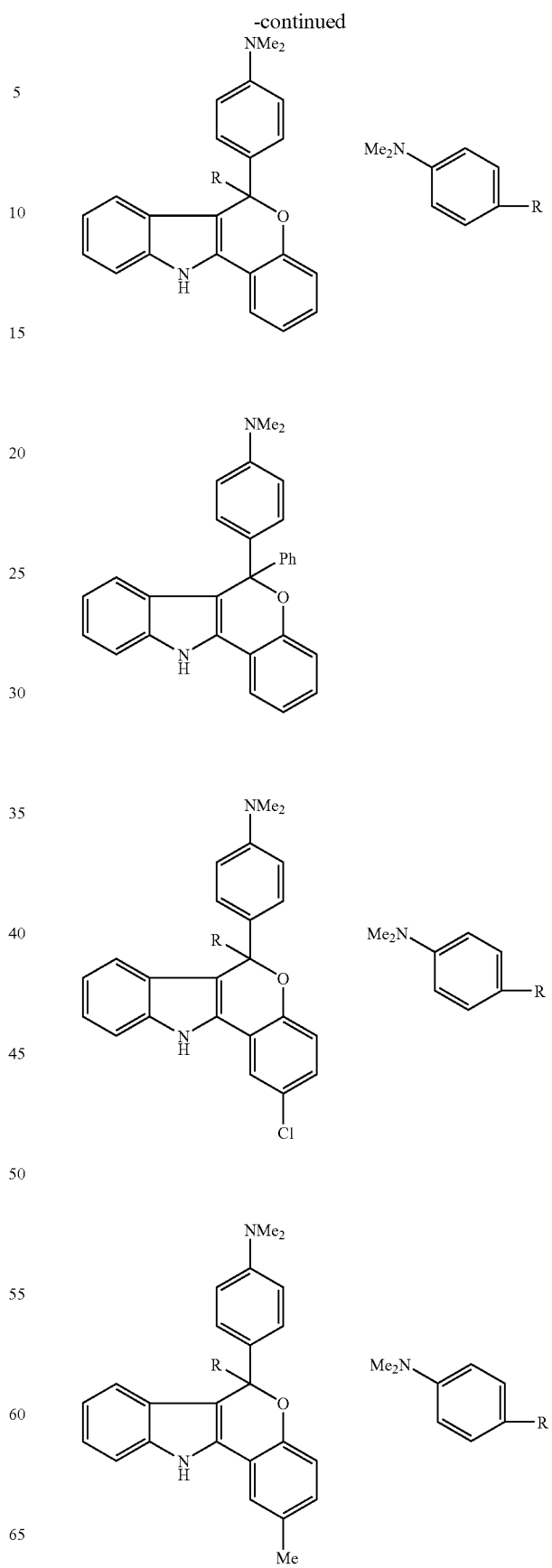

-continued
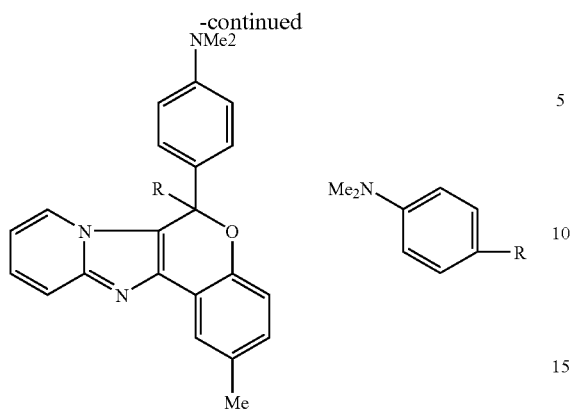
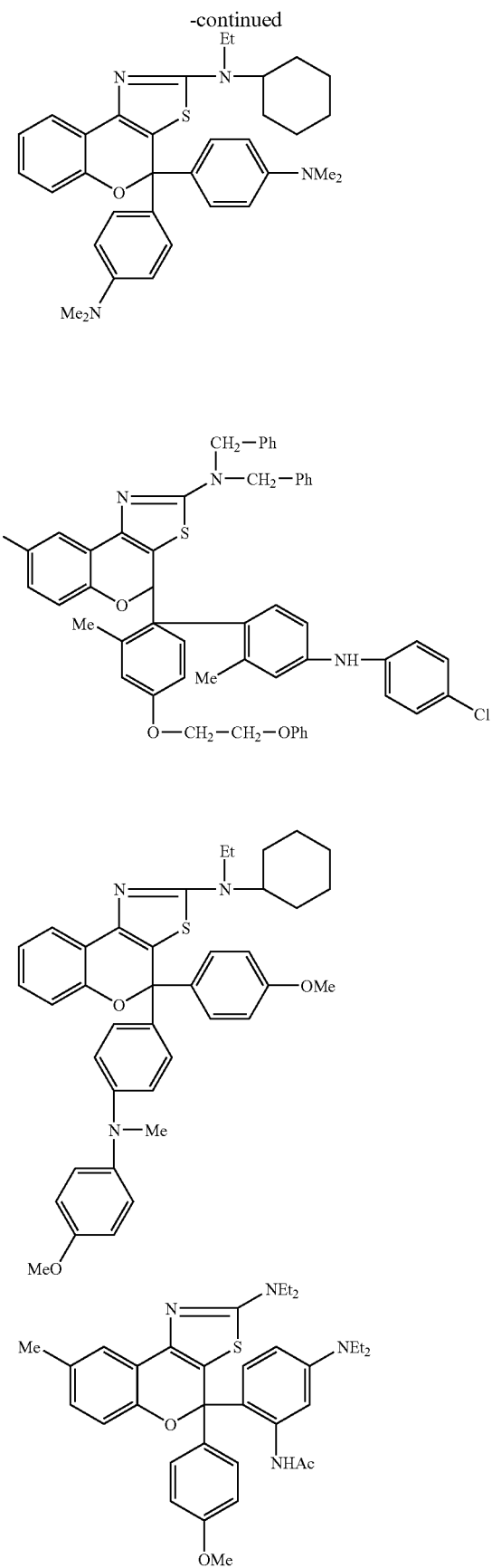

-continued
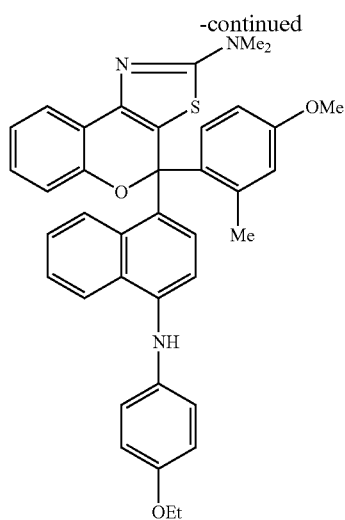
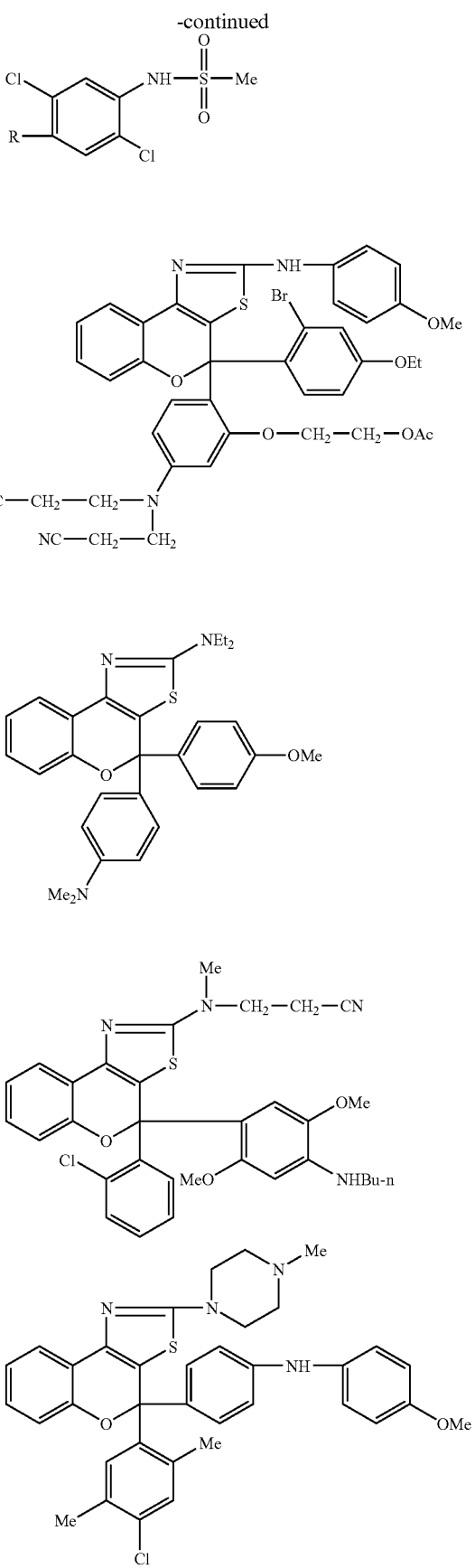

-continued
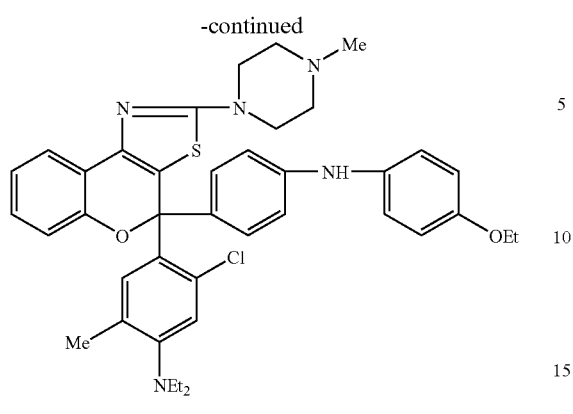
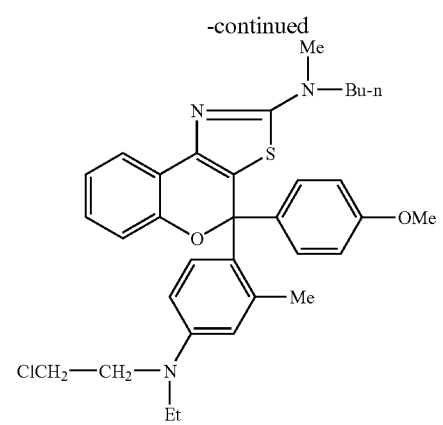
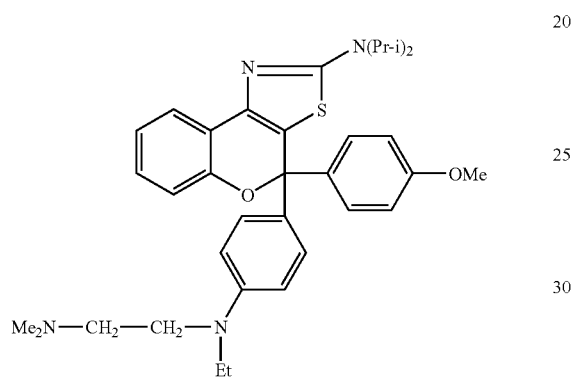
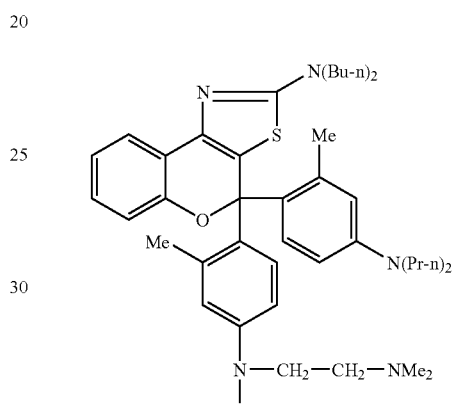
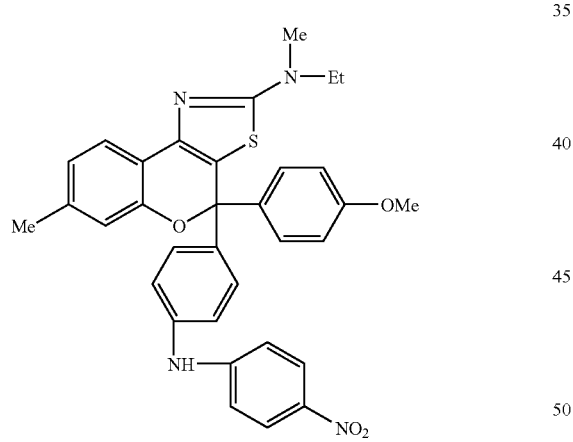
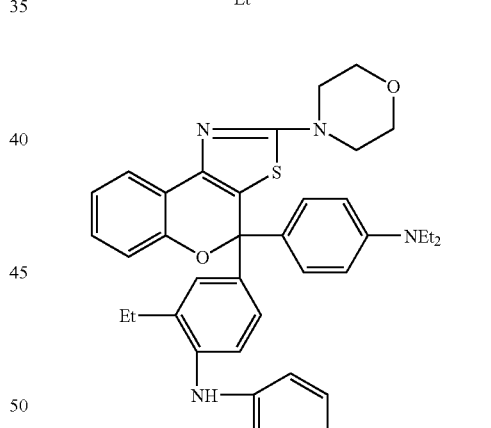
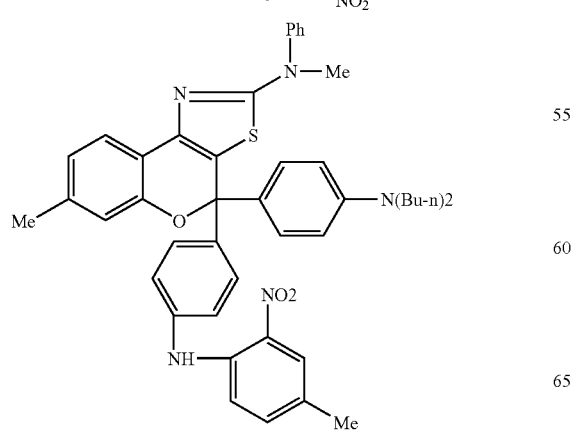
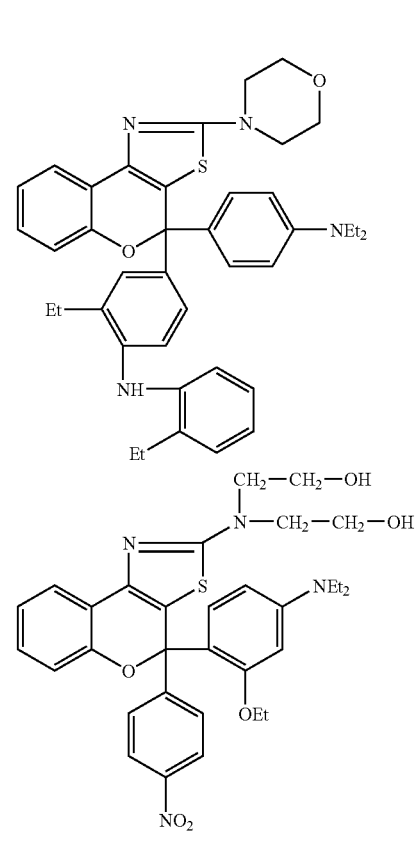

-continued
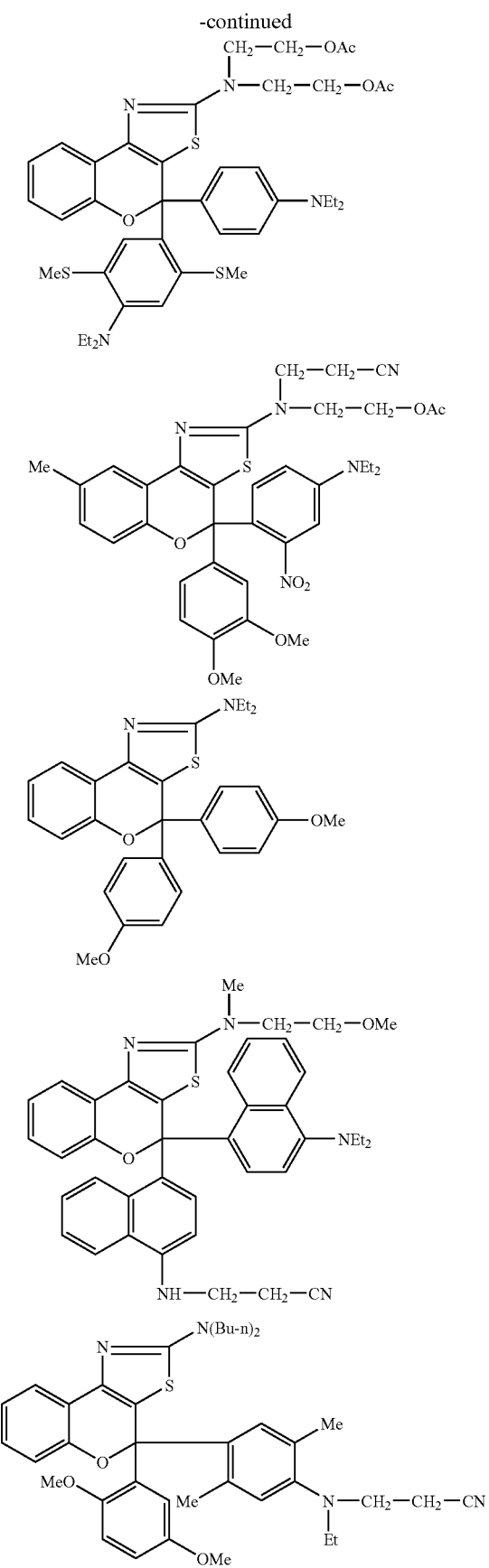
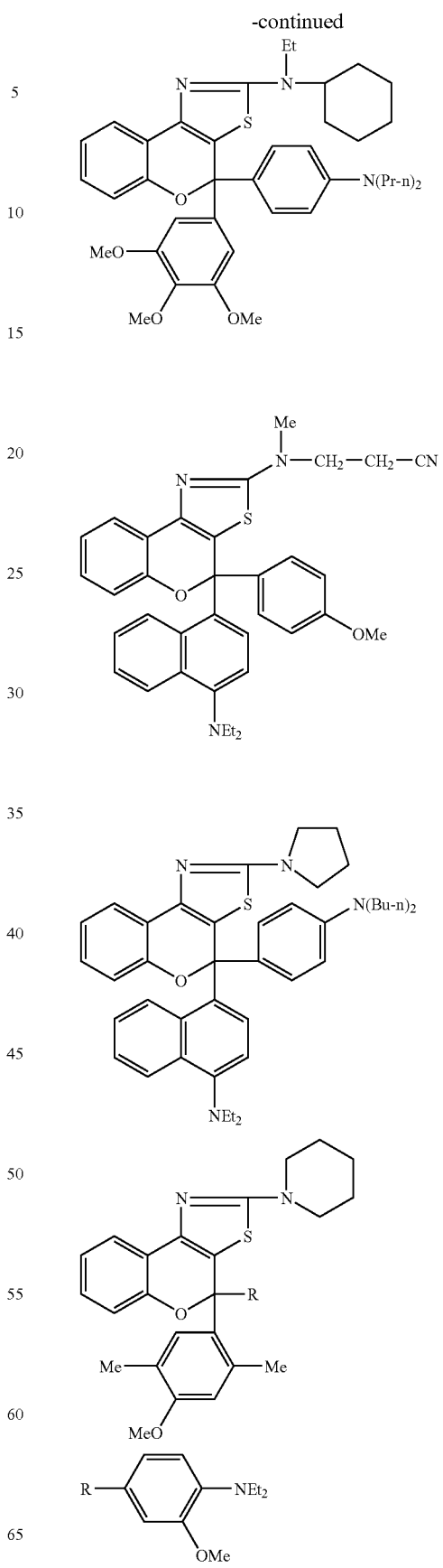

-continued
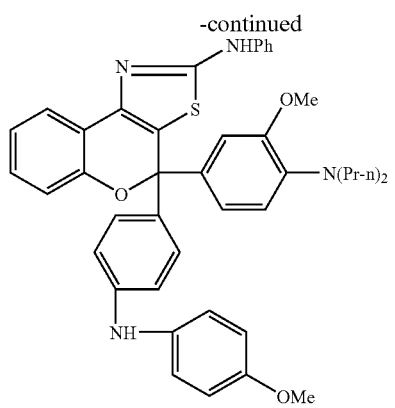
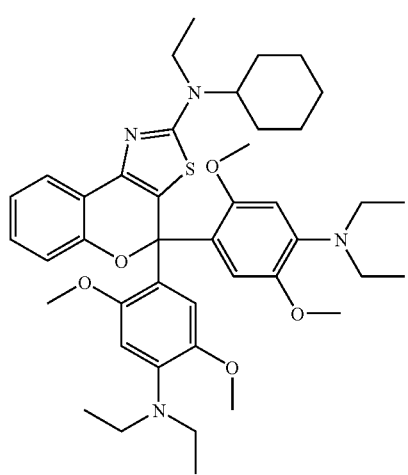
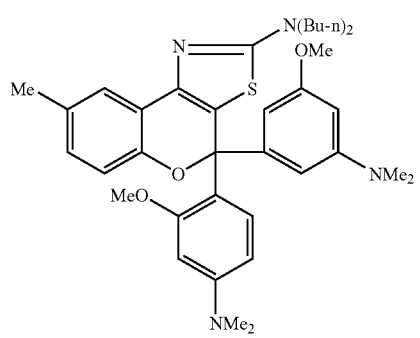
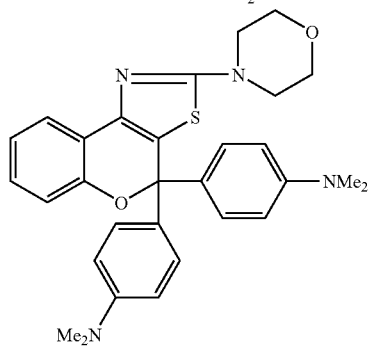
-continued
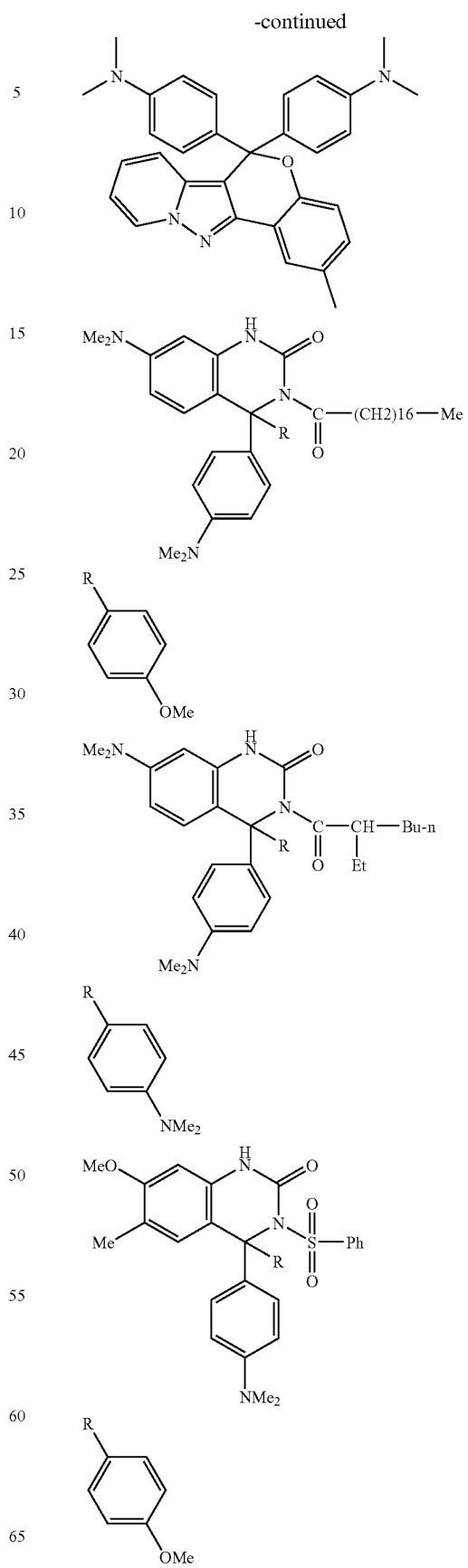

-continued
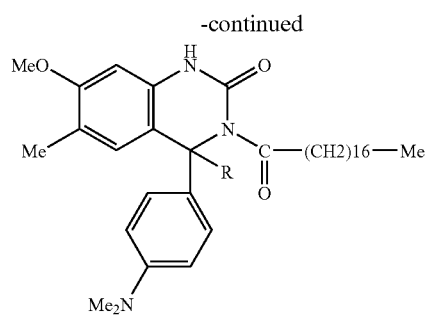
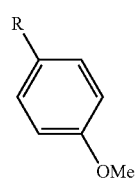
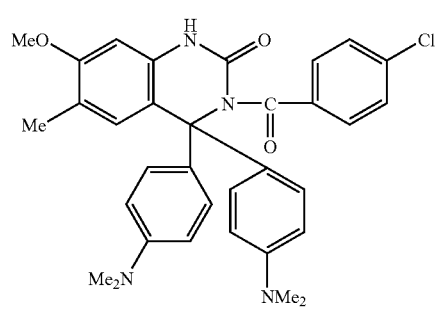
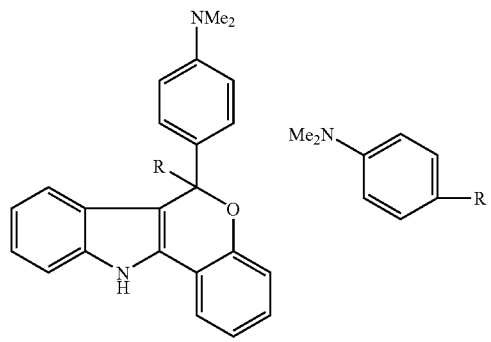
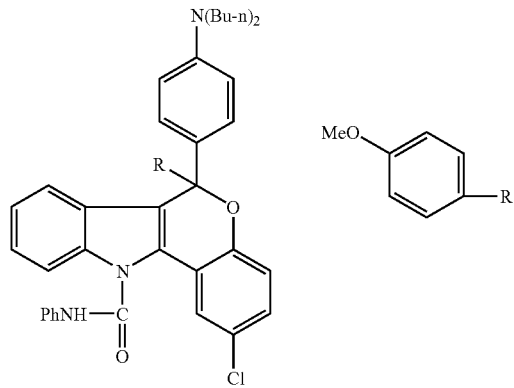
-continued
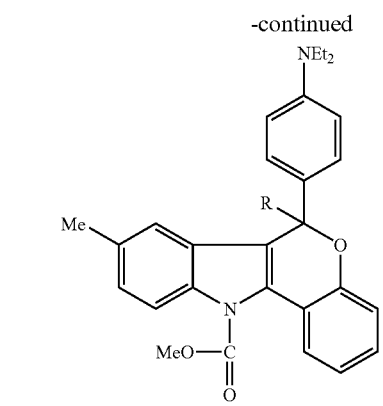
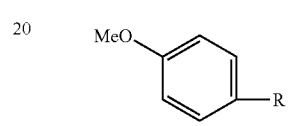
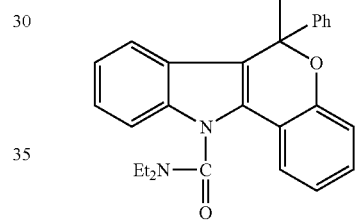
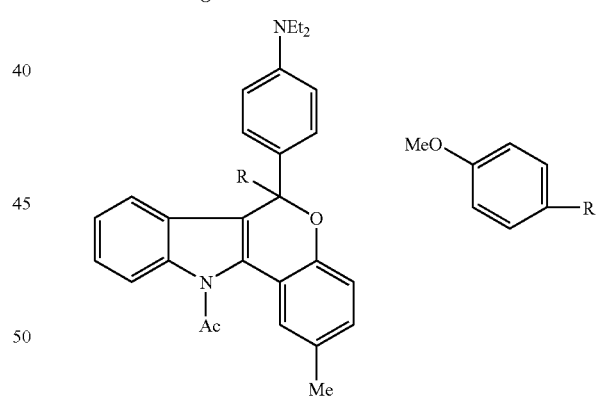
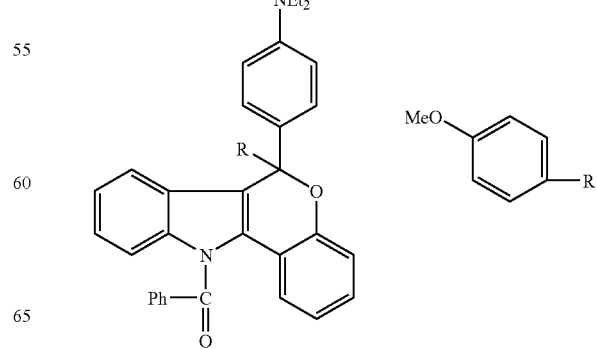

-continued
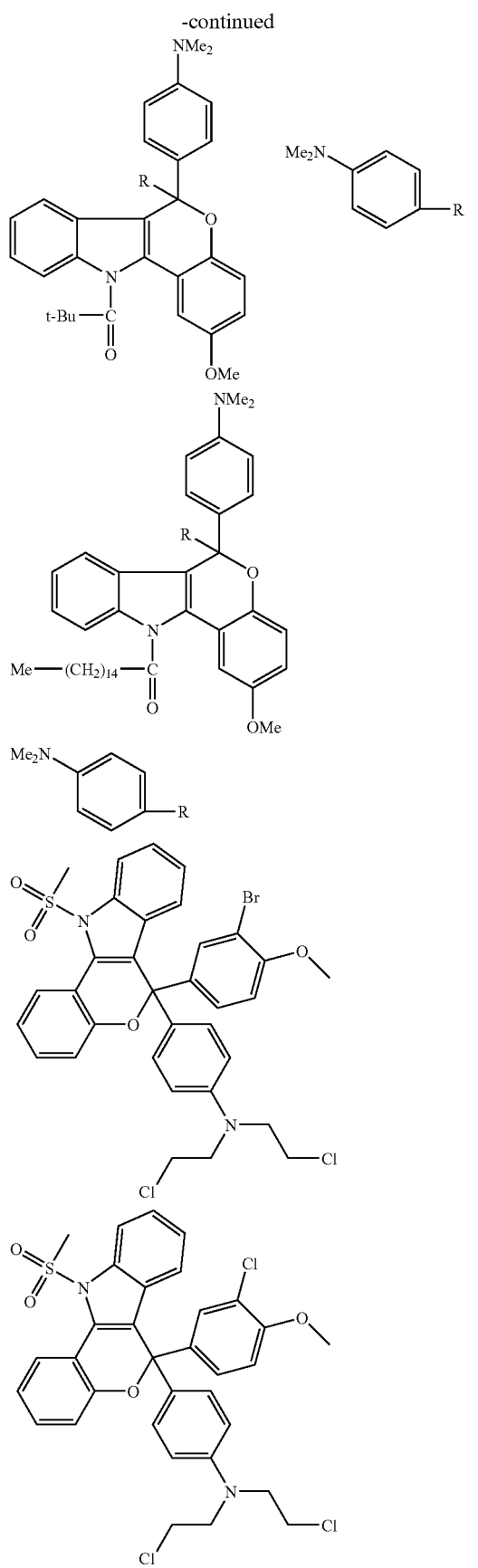
-continued
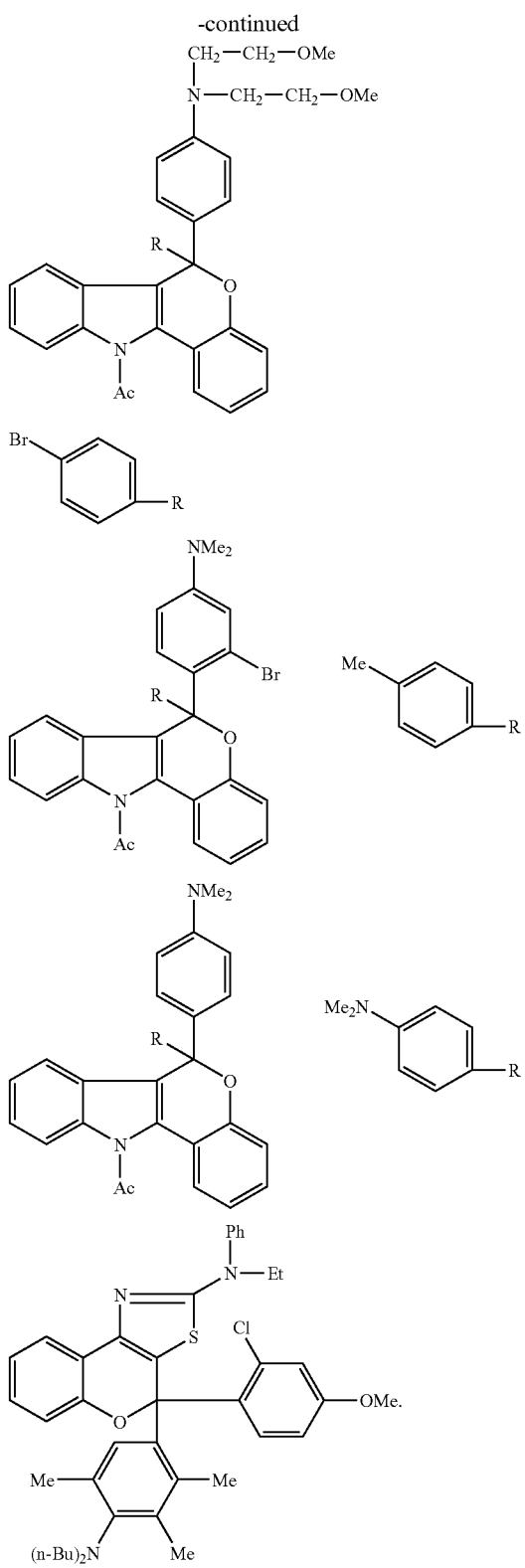
9. The composition according to claim 1, wherein the at least one compound is present in an amount ranging from 0.001 to 10% by weight, relative to the total weight of the composition.

10. The composition according to claim 1, wherein the pH ranges from 3 to 12.

11. A method for the treatment of keratinous fibers, comprising:
applying to the keratinous fibers, for a sufficient development time, a dyeing composition comprising, in a medium appropriate for dyeing comprising water and/or at least one organic solvent, at least one thickening agent, and, at least one compound chosen from the compounds of formula (I), the dyes corresponding to the compounds of formula (I) wherein the ring H is open, and the addition salts thereof:

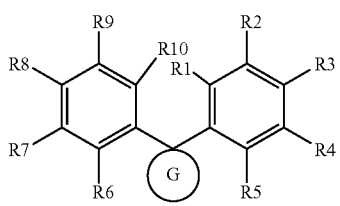
(I)

wherein:
$R_1$, $R_2$, $R_3$, $R_4$, $R_5$, $R_6$, $R_7$, $R_8$, $R_9$ and $R_{10}$ are each independently chosen from:
hydrogen atoms;
halogen atoms;
hydroxyl radicals;
nitro radicals;
amino radicals;
carboxyl radical;
aminocarbonyl radicals;
cyano radicals; and
radicals resulting from a hydrocarbon chain comprising from 1to 100 carbon atoms, which is linear or branched, saturated or unsaturated and acyclic or monocyclic, wherein the ring is aromatic or nonaromatic, or polycyclic, wherein the rings are fused or unfused and aromatic or nonaromatic, which can be interrupted or terminated at one of its ends by at least one heteroatom chosen from oxygen and sulfur atoms or by at least one group chosen from carbonyl, SO, $SO_2$ and NH groups and which can be terminated at its other end by a hydrocarbonyl group or by a group comprising at least one heteroatom chosen from nitrogen, oxygen and sulfur atoms, it being possible for the hydrocarbon chain to be substituted by at least one group chosen from the following radicals: hydroxyl, halo, carboxyl, carboxy($C_1$-$C_9$)alkyl, cyano, amino, amino substituted by one or two $C_1$-$C_4$ alkyl groups, $C_1$-$C_6$ alkoxy, $C_6$-$C_{18}$ aryl, aryloxy, the aryl group of which is a $C_6$-$C_{18}$ group, and $C_2$-$C_9$ acyloxy radicals;
it being possible for two of the $R_1$, $R_2$, $R_3$, $R_4$, $R_5$, $R_6$, $R_7$, $R_8$, $R_9$ and $R_{10}$ radicals carried by two adjacent carbon atoms to form together with the carbon atoms to which they are attached, a monocarbocyclic group wherein the ring is aromatic or nonaromatic or a polycarbocyclic group wherein the rings are fused or unfused and aromatic or nonaromatic, comprising from 5 to 20 ring members, it being possible for at least one carbon atom to be replaced by an entity chosen from oxygen, nitrogen, sulfur and phosphorus atoms, the mono- or polycarbocyclic group being unsubstituted or substituted by at least one substituent chosen from halogen atoms, hydroxyl radicals, amino radicals, carboxyl radicals, $C_6$-$C_{18}$ aryl radicals, cyano radicals, $C_1$-$C_9$ alkyl radicals, $C_1$-$C_9$ alkoxy radicals, ($C_1$-$C_9$)alkoxycarbonyl($C_1$-$C_9$)alkylamino radicals and α-naphthylalkylamino radicals;

G is a divalent radical chosen from those of formulae $G_2$ to $G_5$:

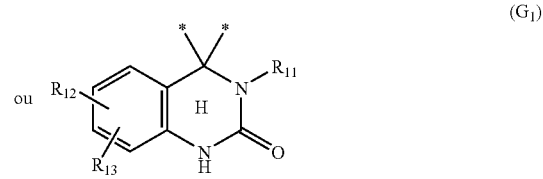
(G₁)

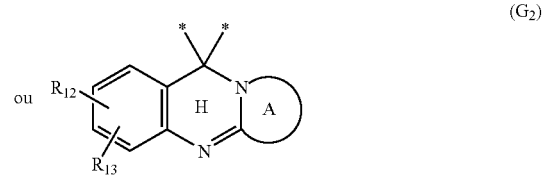
(G₂)

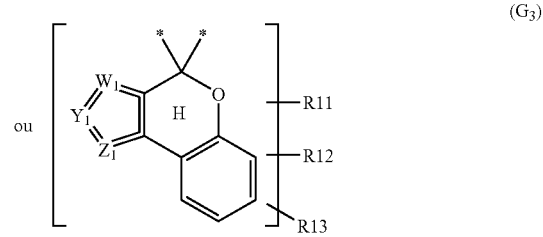
(G₃)

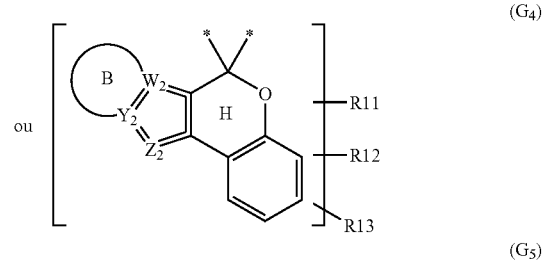
(G₄)

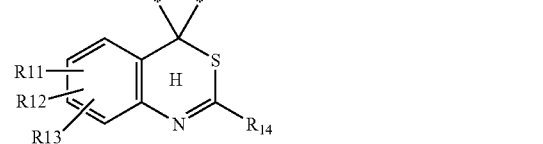
(G₅)

wherein:
$Y_1$, $W_1$ and $Z_1$, on the one hand, and $Y_2$, $W_2$ and $Z_2$, on the other hand, are each independently chosen from sulfur atoms, carbon atoms, nitrogen atoms and divalent groups $CR_{15}$ and $NR_{15}$;
$R_{11}$, $R_{12}$, $R_{13}$ and $R_{15}$ have, independently of one another, the same definitions as the $R_1$ to $R_{10}$ radicals;
$R_{14}$ is chosen from:
hydrogen atoms;
$C_1$-$C_9$ alkyl radicals;
amino radicals;
$C_1$-$C_9$ alkoxy radicals;
($C_1$-$C_9$)alkylthio radicals;
$C_6$-$C_{18}$ aryl radicals which are optionally substituted by at least one group chosen from hydroxyl, $C_1$-$C_9$ alkyl, halo, carboxyl, cyano and amino radicals;
furanyl radicals; and
thienyl radicals;

it being possible for two of the $R_{11}$, $R_{12}$ and $R_{13}$ radicals carried by two adjacent carbon atoms to form together with the carbon atoms to which they are attached, a monocarbocyclic group wherein the ring is aromatic or nonaromatic or a polycarbocyclic group wherein the rings are fused or unfused and aromatic or nonaromatic, comprising from 5 to 20 ring members, it being possible for at least one carbon atom to be replaced by an entity chosen from oxygen, nitrogen, sulfur and phosphorus atoms, the mono- or polycarbocyclic group being optionally substituted by at least one substituent chosen from halogen atoms, hydroxyl radicals, amino radicals, carboxyl radicals, $C_6$-$C_{18}$ aryl radicals, cyano radicals, $C_1$-$C_9$ alkyl radicals and $C_1$-$C_9$ alkoxy radicals;

A is a saturated or unsaturated, substituted or unsubstituted, heterocyclic group comprising from 5 to 12 ring members;

B is chosen from $C_6$-$C_{18}$ aryl groups and heterocyclic groups comprising from 5 to 12 ring members which are unsaturated or saturated and unsubstituted or substituted;

the amino radicals being optionally substituted by one or two identical or different radicals chosen from $C_1$-$C_9$ alkyl radicals; $C_1$-$C_9$ hydroxyalkyl radicals; $C_2$-$C_9$ alkenyl radicals; $C_5$-$C_{12}$ cycloalkyl radicals; ($C_6$-$C_{18}$)arylcarbonyl radicals; cyclo($C_5$-$C_{12}$)alkyl($C_1$-$C_9$)alkyl radicals; ($C_1$-$C_9$)alkylcarbonyl radicals; ($C_1$-$C_9$)alkoxycarbonyl($C_1$-$C_9$)alkyl radicals; α-naphthylalkyl radicals; $C_1$-$C_9$ haloalkyl radicals; ($C_1$-$C_9$)alkylcarbonyloxy($C_1$-$C_9$)alkyl radicals; $C_1$-$C_9$ cyanoalkyl radicals; $C_2$-$C_{15}$ acyl radicals; ($C_1$-$C_9$)alkoxycarbonyl radicals; ($C_6$-$C_{18}$)aryloxycarbonyl radicals; ($C_6$-$C_{18}$)aryloxy($C_1$-$C_9$)alkylcarbonyl radicals; ($C_6$-$C_{18}$)aryl($C_1$-$C_9$)alkoxycarbonyl radicals; ($C_1$-$C_9$)alkoxy($C_6$-$C_{18}$)arylcarbonyl radicals; di($C_1$-$C_9$)alkylaminocarbonyl radicals; di($C_1$-$C_9$)alkylaminosulfonyl radicals; ($C_1$-$C_9$)alkyl($C_6$-$C_{18}$) arylsulfonyl radicals; ($C_1$-$C_9$)alkylsulfonyl radicals; di($C_1$-$C_9$)alkyl-amino($C_1$-$C_9$)alkyl radicals; ($C_1$-$C_9$) alkoxy($C_1$-$C_9$)alkyl radicals; $C_6$-$C_{18}$ aryl radicals and ($C_6$-$C_{18}$)aryl($C_1$-$C_9$)alkyl radicals optionally substituted on the aryl nucleus by at least one substituent chosen from halogen atoms, $C_1$-$C_9$ alkyl radicals, nitro radicals, di($C_1$-$C_9$)alkylamino radicals and $C_1$-$C_9$ alkoxy radicals; it being possible for the two radicals to form together with the nitrogen atom of the amino group, a 5- to 12-membered ring optionally carrying another heteroatom, it being possible for the said ring to be substituted by a $C_1$-$C_9$ alkyl radical, wherein the pH is adjusted using at least one first acidifying agent or at least one first basifying agent according to the coloring desired; and optionally modifying the coloring of the keratinous fibers by applying at least one second acidifying agent or at least one second basifying agent to the keratinous fibers.

12. The method according to claim 11, wherein, the at least one first acidifying agent or the at least one first basifying agent is mixed with the dyeing composition before application to the keratinous fibers.

13. The method according to claim 11, wherein, the at least one first acidifying agent or the least one first basifying agent is applied to the keratinous fibers before or after the dyeing composition.

14. The method according to claim 11, wherein the at least one acidifying agent is chosen from inorganic acids and organic acids.

15. The method according to claim 14, wherein the at least one inorganic acid is chosen from hydrochloric acid, nitric acid and sulfuric acid.

16. The method according to claim 14, wherein the at least one organic acid is chosen from compounds comprising at least one carboxylic acid functional group, one sulfonic acid functional group, one phosphonic acid functional group and one phosphoric acid functional group.

17. The method according to claim 11, wherein the at least one basifying agent is chosen from:

basic amino acids;

alkali metal or alkaline earth metal carbonates or bicarbonates;

silicates or metasilicates; and compounds of formula (II):

$$X(OH)_n \quad (II)$$

wherein:

X is chosen from potassium, lithium, sodium, and ammonium $N^+R_{17}R_{18}R_{19}R_{20}$ ions wherein $R_{17}$, $R_{18}$, $R_{19}$ and $R_{20}$, which are identical or different, are $C_2$-$C_4$ alkyl radicals, when n is equal to 1;

X is chosen from magnesium and calcium atoms, when n is equal to 2;

compounds of formula (III):

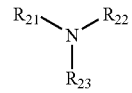

(III)

wherein:

$R_{21}$ is chosen from hydrogen atoms, $C_1$-$C_6$ alkyl radicals, $C_1$-$C_6$ monohydroxyalkyl radicals and $C_2$-$C_6$ polyhydroxyalkyl radicals;

$R_{22}$ and $R_{23}$, which are identical or different, are chosen from hydrogen atoms, $C_1$-$C_6$ alkyl radicals, $C_1$-$C_6$ monohydroxyalkyl radicals and $C_2$-$C_6$ polyhydroxyalkyl radicals;

compounds of formula (IV):

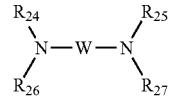

(IV)

wherein:

W is a propylene residue optionally substituted by a hydroxyl group or a $C_1$-$C_4$ alkyl radical;

$R_{24}$, $R_{25}$, $R_{26}$ and $R_{27}$, which are identical or different, are chosen from hydrogen atoms, $C_1$-$C_4$ alkyl radicals and $C_1$-$C_4$ hydroxyalkyl radicals.

18. A multi compartment kit comprising, at least one first compartment comprising a composition, in a medium appropriate for dyeing comprising water and/ or at least one organic solvent, at least one thickening agent, and comprising at least one compound chosen from the compounds of formula (I), the dyes corresponding to the compounds of formula (I) wherein the ring H is open, and the addition salts thereof:

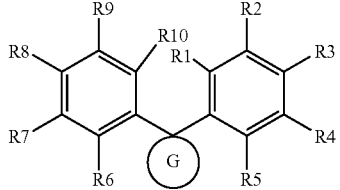
(I)

wherein:

$R_1$, $R_2$, $R_3$, $R_4$, $R_5$, $R_6$, $R_7$, $R_8$, $R_9$ and $R_{10}$ are each independently chosen from:
  hydrogen atoms;
  halogen atoms;
  hydroxyl radicals;
  nitro radicals;
  amino radicals;
  carboxyl radicals;
  aminocarbonyl radicals;
  cyano radicals; and
  radicals resulting from a hydrocarbon chain comprising from 1 to 100 carbon atoms, which is linear or branched, saturated or unsaturated and acyclic or monocyclic, wherein the ring is aromatic or nonaromatic, or polycyclic, wherein the rings are fused or unfused and aromatic or nonaromatic, which can be interrupted or terminated at one of its ends by at least one heteroatom chosen from oxygen and sulfur atoms or by at least one group chosen from carbonyl, SO, $SO_2$ and NH groups and which can be terminated at its other end by a hydrocarbonyl group or by a group comprising at least one heteroatom chosen from nitrogen, oxygen and sulfur atoms, it being possible for the hydrocarbon chain to be substituted by at least one group chosen from the following radicals: hydroxyl, halo, carboxyl, carboxy($C_1$-$C_9$)alkyl, cyano, amino, amino substituted by one or two $C_1$-$C_4$ alkyl groups, $C_1$-$C_6$ alkoxy, $C_6$-$C_{18}$ aryl, aryloxy, the aryl group of which is a $C_6$-$C_{18}$ group, and $C_2$-$C_9$ acyloxy radicals;

it being possible for two of the $R_1$, $R_2$, $R_3$, $R_4$, $R_5$, $R_6$, $R_7$, $R_8$, $R_9$ and $R_{10}$ radicals carried by two adjacent carbon atoms to form together with the carbon atoms to which they are attached, a monocarbocyclic group wherein the ring is aromatic or nonaromatic or a polycarbocyclic group wherein the rings are fused or unfused and aromatic or nonaromatic, comprising from 5 to 20 ring members, it being possible for at least one carbon atom to be replaced by an oxygen, nitrogen, sulfur or phosphorus atom, the mono- or polycarbocyclic group being unsubstituted or substituted by at least one substituent chosen from halogen atoms, hydroxyl radicals, amino radicals, carboxyl radicals, $C_6$-$C_{18}$ aryl radicals, cyano radicals, $C_1$-$C_9$ alkyl radicals, $C_1$-$C_9$ alkoxy radicals, ($C_1$-$C_9$)alkoxycarbonyl($C_1$-$C_9$)alkylamino radicals and αnaphthylalkylamino radicals;

G is a divalent radical chosen from the formulae $G_2$ to $G_5$:

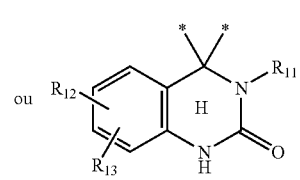
($G_1$)

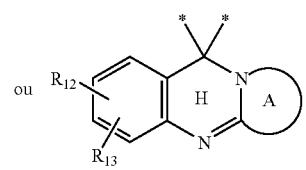
($G_2$)

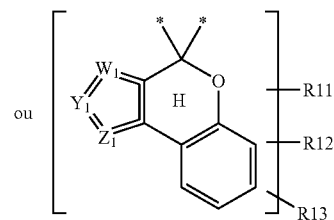
($G_3$)

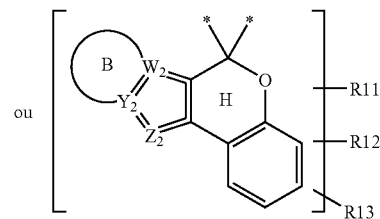
($G_4$)

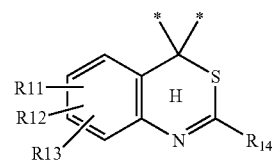
($G_5$)

wherein:

$Y_1$, $W_1$ and $Z_1$, on the one hand, and $Y_2$, $W_2$ and $Z_2$, on the other hand, are each independently chosen from sulfur atoms, carbon atoms, nitrogen atoms and divalent groups $CR_{15}$ and $NR_{15}$;

$R_{11}$, $R_{12}$, $R_{13}$ and $R_{15}$ have, independently of one another, the same definitions as the $R_1$ to $R_{10}$ radicals;

$R_{14}$ is chosen from:
  hydrogen atoms;
  $C_1$-$C_9$ alkyl radicals;
  amino radicals;
  $C_1$-$C_9$ alkoxy radicals;
  ($C_1$-$C_9$)alkylthio radicals;
  $C_6$-$C_{18}$ aryl radicals which are unsubstituted or substituted by at least one radical chosen from hydroxyl, $C_1$-$C_9$ alkyl, halo, carboxyl, cyano and amino radicals;
  furanyl radicals; and
  thienyl radicals;

it being possible for two of the $R_{11}$, $R_{12}$ and $R_{13}$ radicals carried by two adjacent carbon atoms to form together with the carbon atoms to which they are attached, a monocarbocyclic group wherein the ring is aromatic or nonaromatic or a polycarbocyclic group wherein the rings are fused or unfused and aromatic or nonaromatic, comprising from 5 to 20 ring members, it being possible for at least one carbon atom to be replaced by an entity chosen from oxygen, nitrogen, sulfur and phosphorus atoms, the mono- or polycarbocyclic group being unsubstituted or substituted by at least one substituent chosen from halogen atoms, hydroxyl radicals, amino radicals, carboxyl radicals, $C_6$-$C_{18}$ aryl radicals, cyano radicals, $C_1$-$C_9$ alkyl radicals and $C_1$-$C_9$ alkoxy radicals;

A is a saturated or unsaturated, substituted or unsubstituted, heterocyclic group comprising from 5 to 12 ring members;

B is chosen from $C_6$-$C_{18}$ aryl groups and heterocyclic groups comprising from 5 to 12 ring members which are saturated or unsaturated and substituted or unsubstituted;

the amino radicals being unsubstituted or substituted by one or two identical or different radicals chosen from $C_1$-$C_9$ alkyl radicals; $C_1$-$C_9$ hydroxyalkyl radicals; $C_2$-$C_9$ alkenyl radicals; $C_5$-$C_{12}$ cycloalkyl radicals; ($C_6$-$C_{18}$)arylcarbonyl radicals; cyclo($C_5$-$C_{12}$)alkyl($C_1$-$C_9$) alkyl radicals; ($C_1$-$C_9$)alkylcarbonyl radicals; ($C_1$-$C_9$)alkoxy-carbonyl($C_1$-$C_9$)alkyl radicals; α-naphthylalkyl radicals; $C_1$-$C_9$ haloalkyl radicals; ($C_1$-$C_9$)alkylcarbonyloxy($C_1$-$C_9$)alkyl radicals; $C_1$-$C_9$ cyanoalkyl radicals; $C_2$-$C_{15}$ acyl radicals; ($C_1$-$C_9$)alkoxycarbonyl radicals; ($C_6$-$C_{18}$)aryloxycarbonyl radicals; ($C_6$-$C_{18}$)aryloxy($C_1$-$C_9$)alkylcarbonyl radicals; ($C_6$-$C_{18}$)aryl($C_1$-$C_9$)alkoxycarbonyl radicals; ($C_1$-$C_9$)alkoxy($C_6$-$C_{18}$)arylcarbonyl radicals; di($C_6$-$C_{18}$)alkylaminocarbonyl radicals; di($C_1$-$C_9$)alkyl-aminosulfonyl radicals; ($C_1$-$C_9$)alkyl($C_6$-$C_{18}$) arylsulfonyl radicals; ($C_1$-$C_9$)alkylsulfonyl radicals; di($C_1$-$C_9$)alkylamino($C_1$-$C_9$)alkyl radicals; ($C_1$-$C_9$) alkoxy($C_1$-$C_9$)alkyl radicals; $C_6$-$C_{18}$ aryl radicals and ($C_6$-$C_{18}$)aryl($C_1$-$C_9$)alkyl radicals optionally substituted on the aryl nucleus by at least one substituent chosen from halogen atoms, $C_1$-$C_9$ alkyl radicals, nitro radicals, di($C_1$-$C_9$)alkylamino radicals and $C_1$-$C_9$ alkoxy radicals; it being possible for the two radicals to form together with the nitrogen atom of the amino group, a 5- to 12-membered ring optionally carrying another heteroatom, it being possible for the ring to be substituted by a $C_1$-$C_9$ alkyl radical; and at least one second compartment comprising at least one acidifying agent or at least one basifying agent.

19. The kit according to claim 18, comprising, in the at least one second compartment, at least one acidifying agent, and further comprising at least one third compartment comprising at least one basifying agent.

20. The composition according to claim 1, additionally comprising at least one surfactant.

21. The composition according to claim 20, wherein the at least one surfactant is chosen from anionic surfactants, cationic surfactants, non ionic surfactants, amphoteric surfactants, and zwitterionic surfactants.

22. The composition according to claim 1, wherein the at least one thickening agent is chosen from associative thickening polymers and non associative thickening polymers.

23. The composition according to claim 1, wherein the composition is appropriate for coloring human hair.

* * * * *

UNITED STATES PATENT AND TRADEMARK OFFICE
CERTIFICATE OF CORRECTION

PATENT NO. : 7,655,052 B2  Page 1 of 10
APPLICATION NO. : 12/076565
DATED : February 2, 2010
INVENTOR(S) : Alain Lagrange and Frédéric Guerin It is certified that error appears in the above-identified patent and that said Letters Patent is hereby corrected as shown below:

Claim 1, col. 58, lines 25-36, delete

" 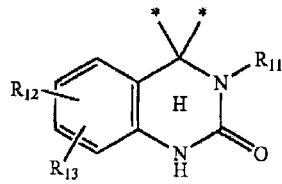 (G₁) "

ou

Claim 1, col. 58, lines 47 and 57, and col. 59, line 4, "ou" should read --or--.

Claim 4, col. 62, lines 5-67 and col. 63, lines 3-32, delete the formula

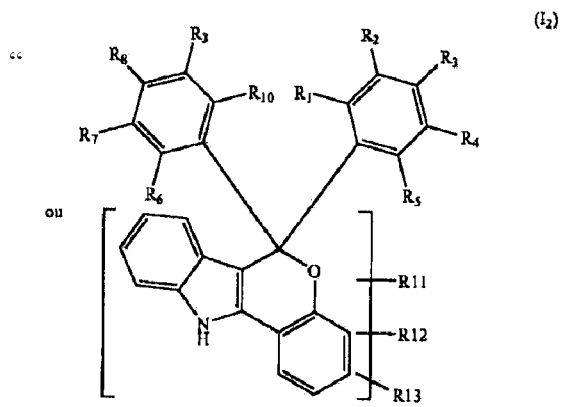
(I₂)
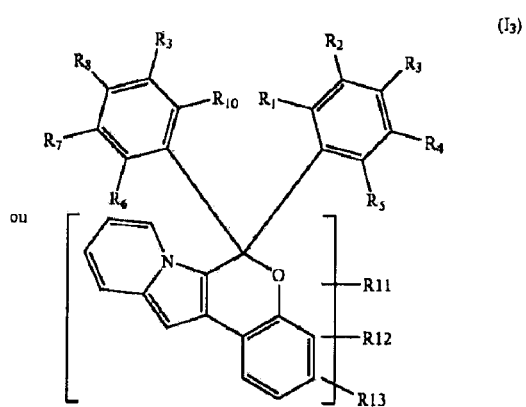
(I₃)
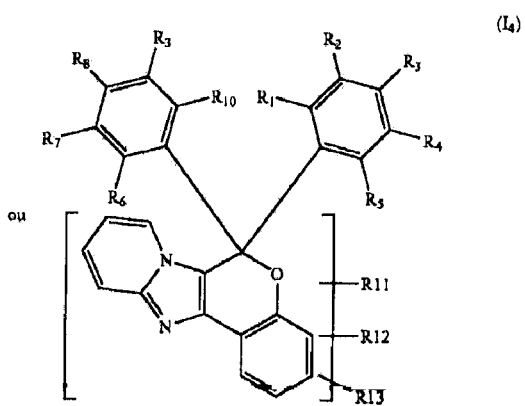
(I₄)

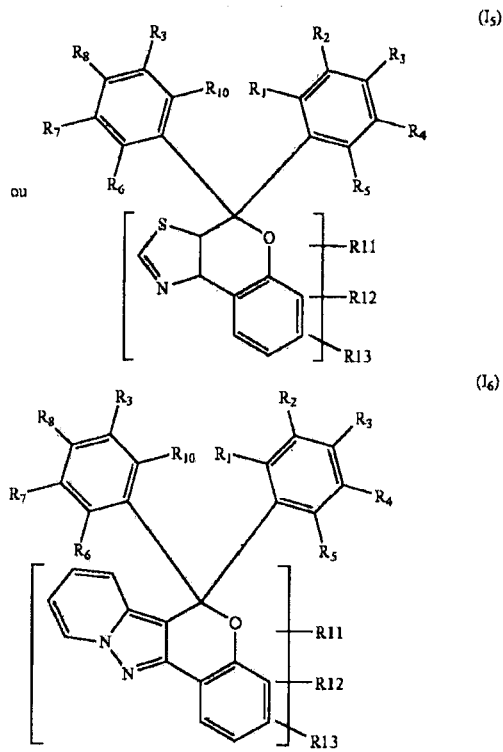
ou
and insert therefor
--
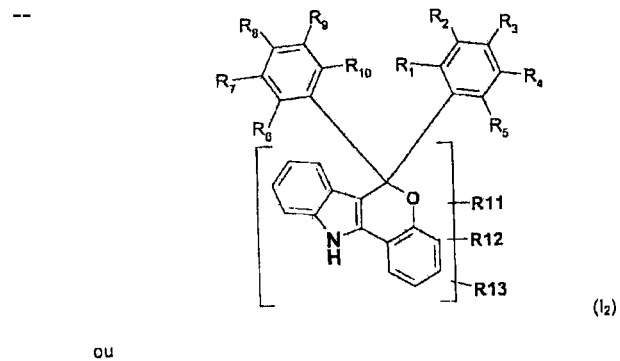
ou

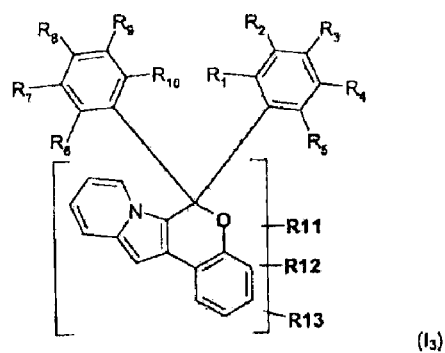
(I₃)
ou
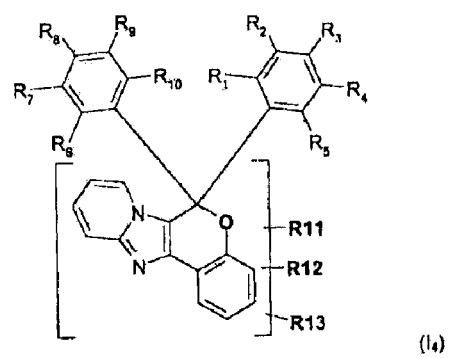
(I₄)
ou
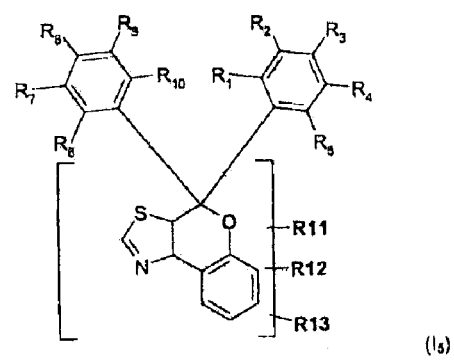
(I₅)
ou
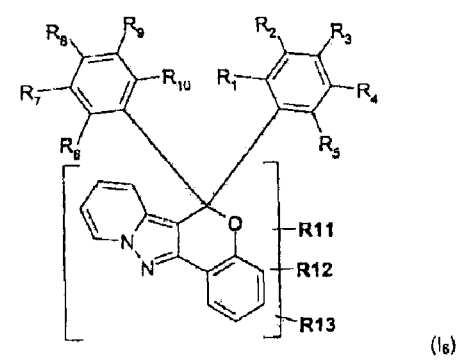
(I₆)
--.

Claim 8, col. 69, lines 55-67, delete the formula
" 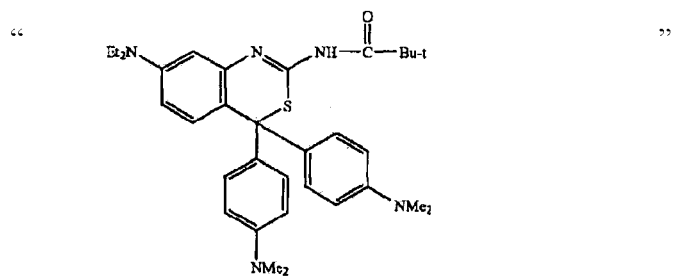 "
and insert therefor
-- 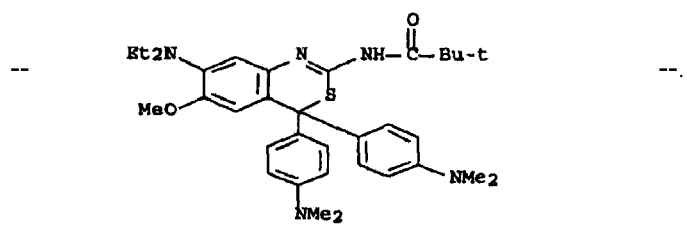 --.
Claim 8, col. 85, lines 1-25, delete the formula
" 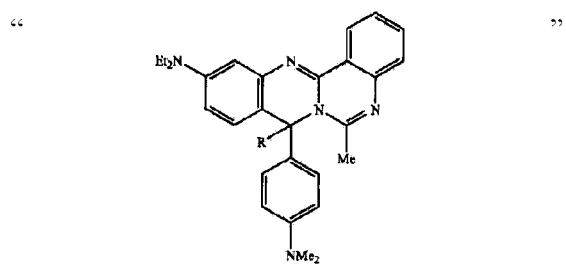
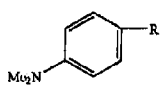 "
and insert therefor
-- 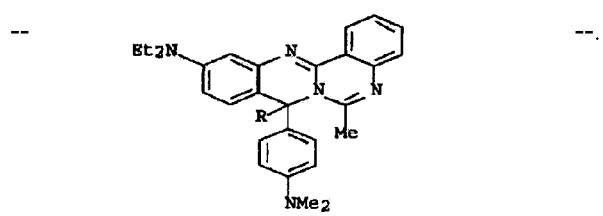 --.
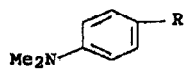

Claim 8, col. 85, lines 26-40, delete the formula
"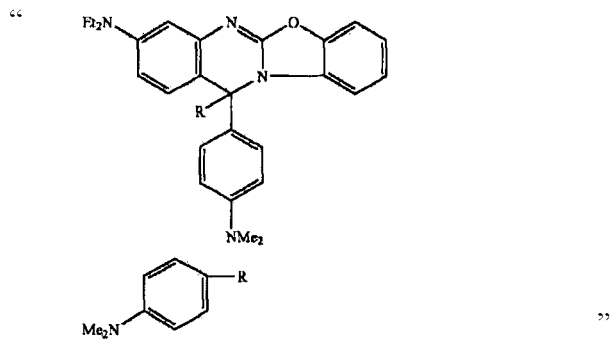"
and insert therefor
--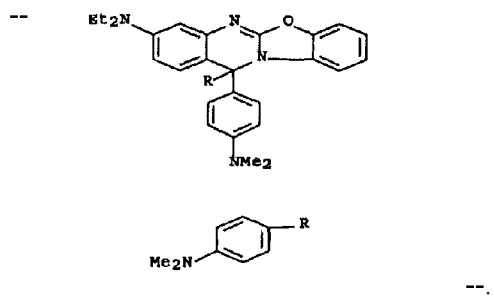--.
Claim 8, col. 91, lines 51-67, delete the formula
"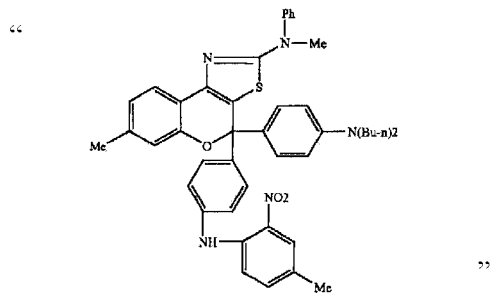"
and insert therefor
--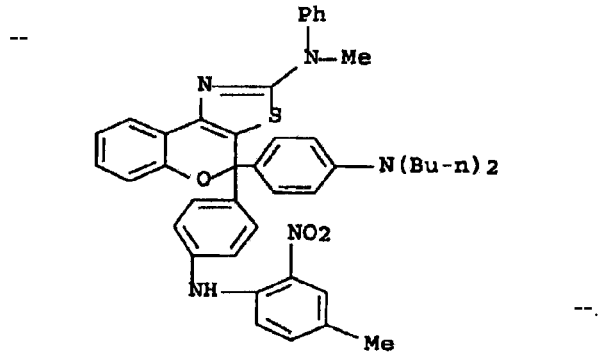--.

Claim 8, col. 93, lines 15-30, delete the formula
"
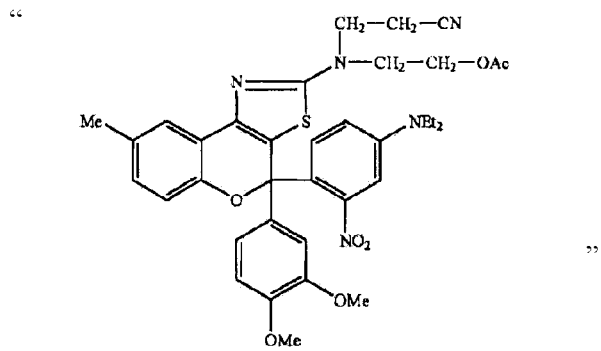
"
and insert therefor
--
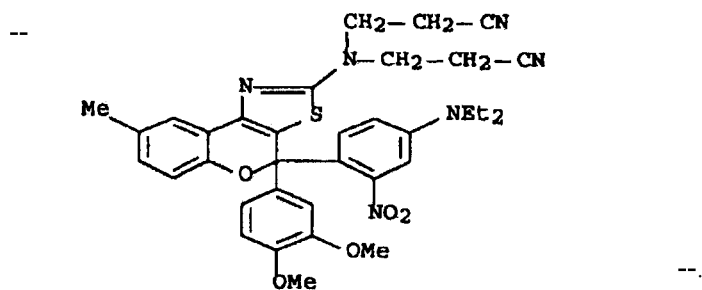
--.
Claim 8, col. 94, lines 35-49, delete the formula
"
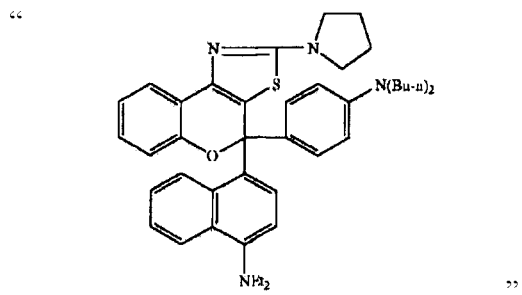
"
and insert therefor
--
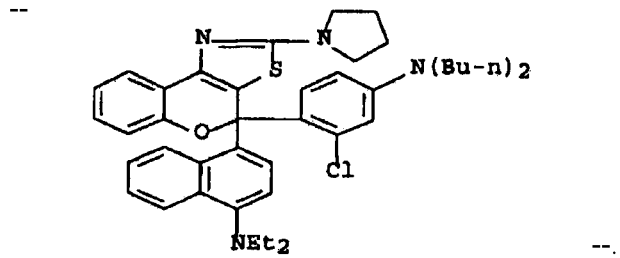
--.

CERTIFICATE OF CORRECTION (continued)
U.S. Pat. No. 7,655,052 B2

Claim 8, col. 96, lines 15-67 and col. 97, lines 1-40, delete the following formula in their entirety:

"
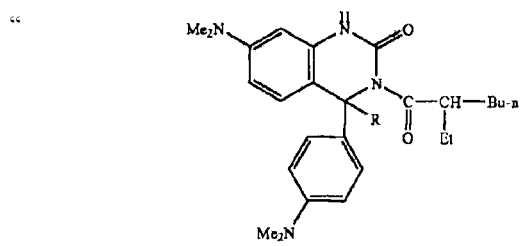
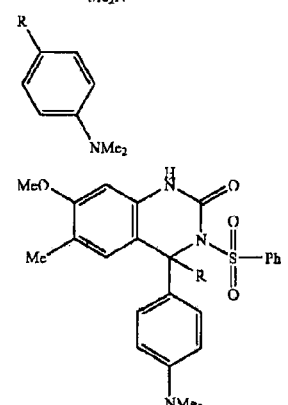
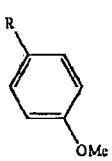
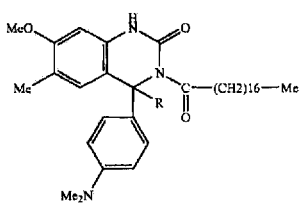
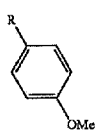
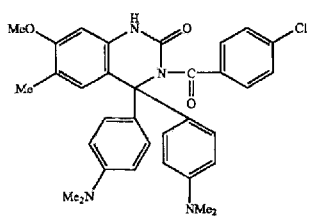
".

Claim 8, col. 99, lines 18-30, delete the formula
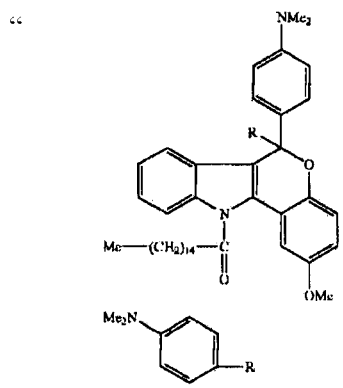
and insert therefor
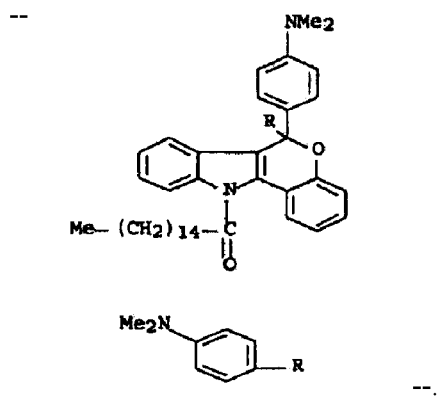
Claim 11, col. 102, lines 10-16, delete
" 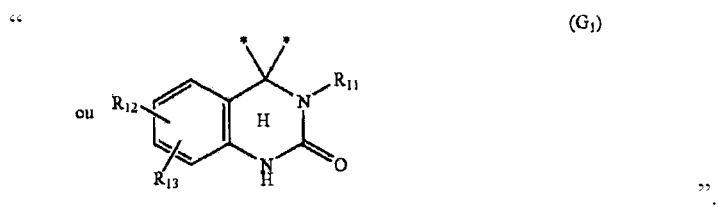 ".
Claim 11, col. 102, lines 19, 27, 36, "ou" should read --or--.

CERTIFICATE OF CORRECTION (continued)
U.S. Pat. No. 7,655,052 B2

Claim 18, col. 106, lines 2-11, delete

" 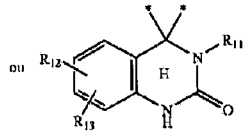 ".

Claim 18, col. 106, lines 14, 23, 31, "ou" should read --or--.